United States Patent [19]
Lee et al.

[11] Patent Number: 5,846,763
[45] Date of Patent: Dec. 8, 1998

[54] DNA ENCODING TUMOR NECROSIS FACTOR STIMULATED GENE 6 (TSG-6)

[75] Inventors: Tae Ho Lee, Daejeon, Rep. of Korea; Hans-Georg Wisniewski; Jan Vilcek, both of New York, N.Y.

[73] Assignee: New York University, New York, N.Y.

[21] Appl. No.: 242,097

[22] Filed: May 13, 1994

Related U.S. Application Data

[63] Continuation-in-part of Ser. No. 24,868, Mar. 1, 1993, Pat. No. 5,386,013, which is a continuation of Ser. No. 642,312, Jan. 14, 1991, abandoned.

[51] Int. Cl.[6] .............................. C12N 5/10; C12N 15/12; C12N 1/21
[52] U.S. Cl. ................. 435/69.1; 435/320.1; 435/172.3; 435/252.3; 536/23.5; 536/23.1
[58] Field of Search ................................. 536/23.5, 23.1; 435/320.1, 252.3, 69.1, 240.1

[56] References Cited

U.S. PATENT DOCUMENTS 5,386,013  1/1995  Lee et al. .................................. 530/350

OTHER PUBLICATIONS

Bowie et al. 1990. Science 247: 1306–1310.
Dayer, J.M. et al., *J. Exp. Med.*, 162:2163 (1985).
Hajjar, K.A. et al., *J. Exp. Med.*, 166:235 (1987).
Kohase, M. et al., *Cell*, 45:659 (1986).
Le, J. et al., *Lab. Invest.*, 56:234 (1987).
Lin, J.X. et al., *J. Biol. Chem.*, 262:11908 (1987).
Medcalfe, R.R. et al., *J. Exp. Med.*, 168:751 (1988).
Palombella, V.J. et al., *J. Biol. Chem.*, 262:1950 (1987).
Pfizenmaier, K. et al., *J. Immunol.*, 138:975 (1987).
Pober, J.S. et al., *J. Immunol.*, 136:1680 (1986).
Wong, G.H. et al., *Science*, 242:941 (1988).
Wong, G.H. et al., *Nature*, 323:819 (1986).
Lee, et al., *Mol. and Cell Biol.*, vol. 10, pp. 1982–1988, 1990.
Lee, et al., *J. Interferon Res. 9* (Suppl. 2), p. 5145, 1989 (abstract only).
Kirsten, et al., *JBC* 261:9565 (1986).
Lowenthal et al., *PNAS* 86, 1989, pp. 2331–2335.
Le, et al., *Lab. Invest.*, 56(3) 1987, pp. 234–248.
Shannon, et al., *Mol. Cell Biol.*, 10(6) 1990, pp. 2950–2959.
Lee, et al., *J. Interferon Res.*, 9(1) 1989, s145.
Lee, et al., *Mol. Cellular Biol*, 1990, pp. 1982–1989.
Breviaris, et al., *JBC*, 267(31) 1992, pp. 22170–22197.

*Primary Examiner*—Garnette D. Draper
*Assistant Examiner*—Elizabeth C. Kemmerer
*Attorney, Agent, or Firm*—Browdy and Neimark

[57] ABSTRACT

TSG-6 protein and functional derivatives thereof, DNA coding therefor, expression vehicles, such as a plasmids, and host cells transformed or transfected with the DNA molecule, and methods for producing the protein and the DNA are provided, as well as antibodies specific for the TSG-6 protein; a method for detecting the presence of TSG-6 protein in a biological sample; a method for detecting the presence of nucleic acid encoding a normal or mutant TSG-6 protein; a method for measuring induction of expression of TSG-6 in a cell using either nucleic acid hybridization or immunoassay; a method for identifying a compound capable of inducing the expression of TSG-6 in a cell; and a method for measuring the ability of a cell to respond to TNF.

14 Claims, 28 Drawing Sheets

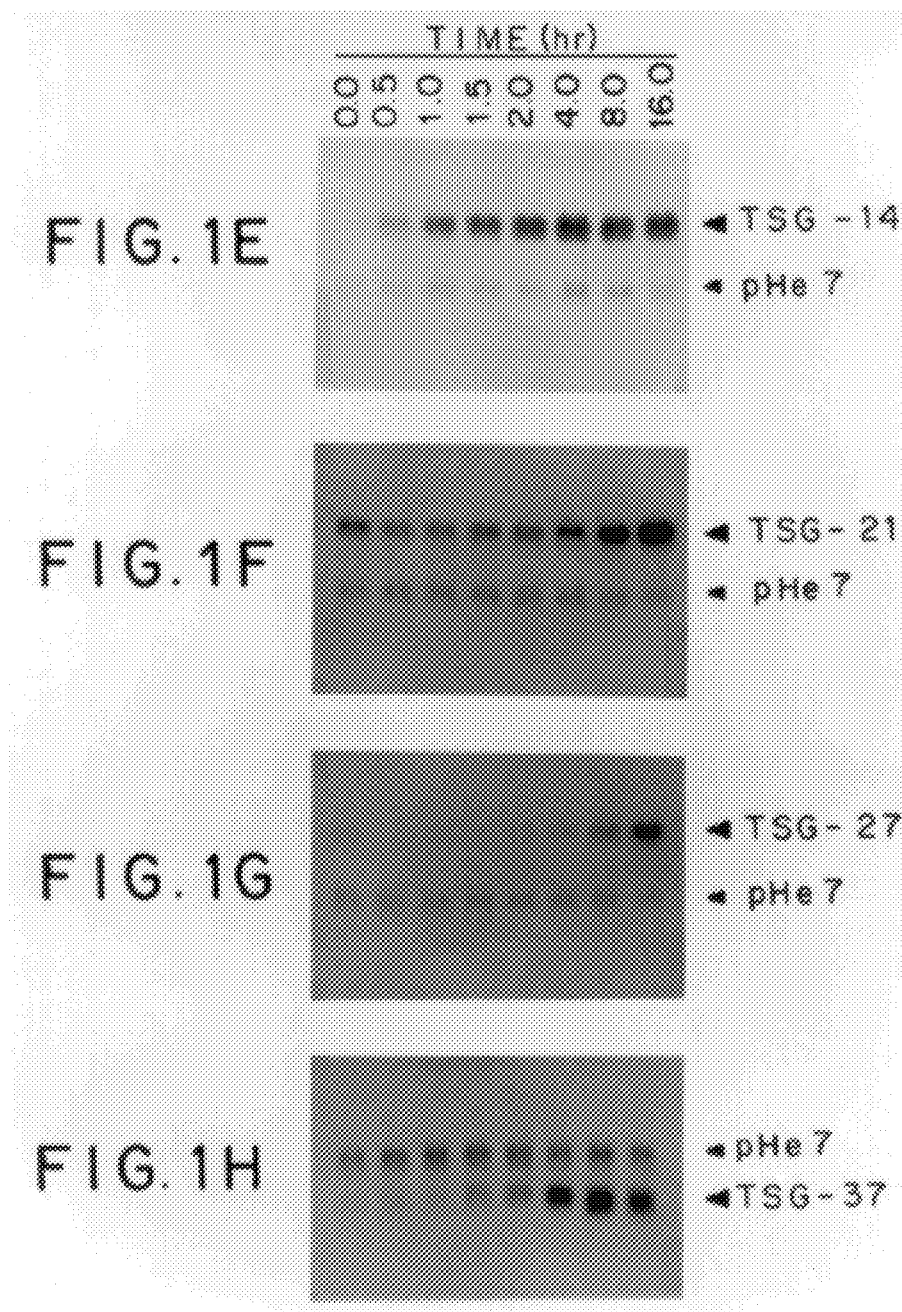

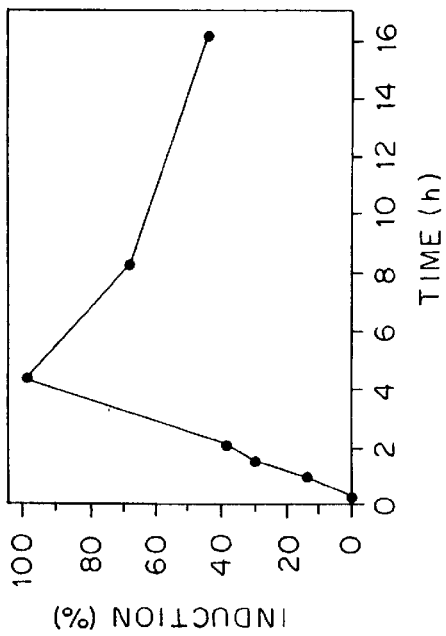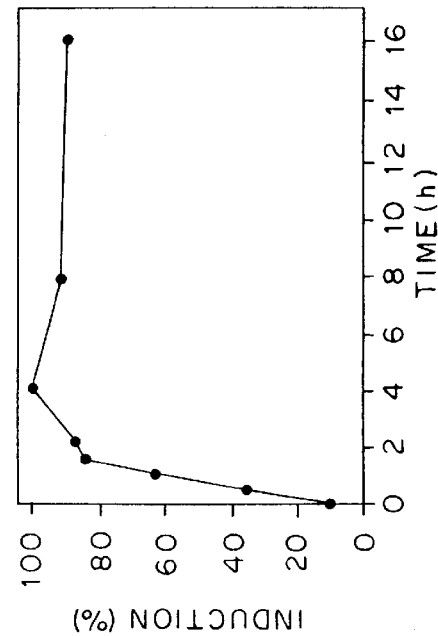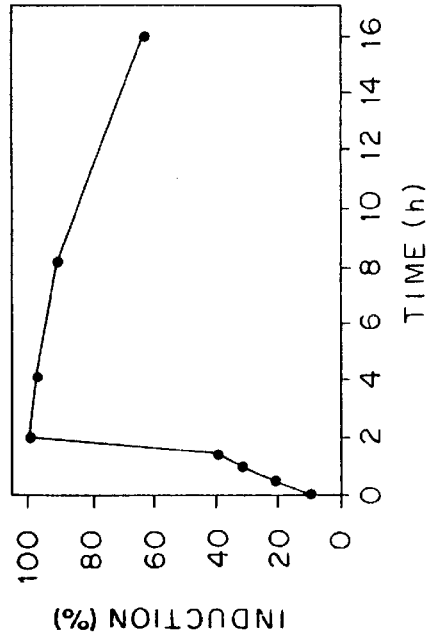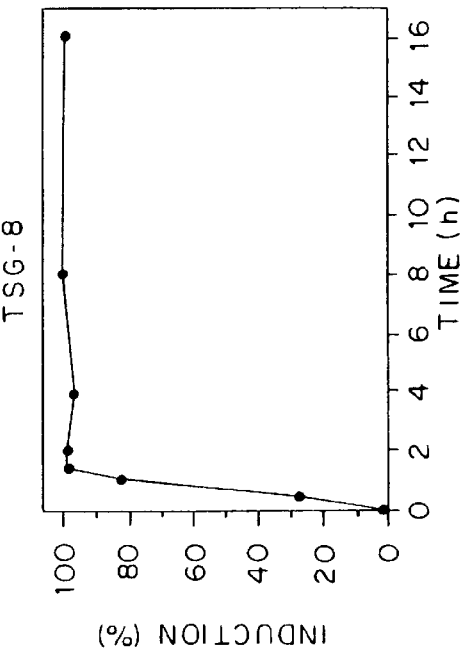
FIG. 2A TSG-1
FIG. 2B TSG-6
FIG. 2C TSG-8
FIG. 2D TSG-12

TSG-21

TSG-37

TSG-14

TSG-27

FIG. 3A

```
-68                                                                    ga att cgc    -61
-60   act gct ctg aga att tgt gag cag ccc cta aca ggc tgt tac ttc act aca act gac gat   -1

1   ATG ATC ATC TTA ATT TAC TTA TTT CTC TTG CTA TTT CTC TTG CTA GAA GAC ACT CAA GGA TCG CCA TTC    60
  1   Met Ile Ile Leu Ile Tyr Leu Phe Leu Leu Leu Phe Glu Asp Thr Gln Gly Trp Gly Phe    20

61   AAG GAT CGA ATT TTT CAT AAC TCC ATA TCG CTT GAA CGA GCA GCC CGT GTG TAC CAG AGA   120
 21   Lys Asp Arg Ile Phe His Asn Ser Ile Trp Leu Glu Arg Ala Ala Gly Val Tyr Gln Arg    40

121   GAA GCA CGG TCT CGC AAA TAC AAG CTC ACC TAC GCA GAA GCT AAG GCG GTG TGT GAA TTT   180
 41   Glu Ala Arg Ser Arg Lys Tyr Lys Leu Thr Tyr Ala Glu Ala Lys Ala Val Cys Glu Phe    60

181   GAA CGC GGC CAT CTC GCA ACT TAC AAG CAG CTA GAG GCA GCA GCG AGA AAA ATT GGA TTT CAT   240
 61   Glu Arg Gly His Leu Ala Thr Tyr Lys Gln Leu Glu Ala Ala Arg Lys Ile Gly Thr His    80

241   CTC TGT GCT GCT GCA TCG ATG GCT AAG GGG AGA GTT GGA TAC CCC ATT GTG AAG CCA CCG   300
 81   Val Cys Ala Ala Gly Trp Met Ala Lys Gly Arg Val Gly Tyr Pro Ile Val Lys Pro Gly   100

301   CCC AAC TGT GGA TTT GGA AAA ACT GCC ATT ATT GAT TAT GGA ATC CGT CTC AAT AGG ACT   360
101   Pro Asn Cys Gly Phe Gly Lys Thr Ala Ile Ile Asp Tyr Gly Ile Arg Leu Asn Arg Ser   120
```

FIG. 3B

```
361  GAA AGA TCG GAT CCC TAT TCC TAC AAC CCA CAC GCA AAG GAG TGT GGT GCC GTC TTT ACA  420
121  Glu Arg Trp Asp Pro Tyr Cys Tyr Asn Pro His Ala Lys Glu Cys Gly Gly Val Phe Thr  140

421  GAT CCA AAG CCA ATT TTT AAA TCT CCA AAT GCC TTC CCA AAT GAG TAC GAA GAT AAC CAA ATC  480
141  Asp Pro Lys Pro Ile Phe Lys Ser Pro Asn Gly Phe Pro Asn Glu Tyr Glu Asp Asn Gln Ile  160

481  TCC TAC TCG CAC ATT AGA CTC AAG TAT GGT CAG CCT ATT CAC CTG AGT TTT TTA GAT TTT  540
161  Cys Tyr Trp His Ile Arg Leu Lys Tyr Gly Gln Pro Ile His Leu Ser Phe Leu Asp Phe  180

541  GAC CTT CAA GAT GAC CCA GCT TCC TTG GCT CAT TAT CTT GAA ATA TAT GAC ACT TAC GAT  600
181  Asp Leu Gln Asp Asp Pro Ala Ser Leu Ala His Tyr Leu Glu Ile Tyr Asp Thr Tyr Asp  200

601  CAT GTC CAT CCC TTT GTG GGA AGA TAC TGT CGT GGA GAT GAG CTT CCA GAT GAC ATC ATC AGT  660
201  Asp Val His Pro Phe Val Gly Arg Tyr Cys Arg Gly Asp Glu Leu Pro Asp Asp Ile Ile Ser  220

661  ACA GGA AAT GTC ATG ACC TTG AAG TTT CTA AGT CAT CCT GCA TCA GTG ACA CCT GCA GGT TTC  720
221  Thr Gly Asn Val Met Thr Leu Lys Phe Leu Ser His Pro Ala Ser Val Thr Pro Ala Gly Phe  240

721  CAA ATC AAA TAT GTT GCA ATG GAT CCT GTA TCC AAA TCC ACT CAA GCA AAA AAT ACA AGT  780
241  Gln Ile Lys Tyr Val Ala Met Asp Pro Val Ser Lys Ser Thr Gln Ala Lys Asn Thr Ser  260

781  ACT ACT TCT ACT CCA AAT AAA AAC TTT TTA GCT CCA ACA TTT ACC CAC TTA taa aaa aaa  840
261  Thr Thr Ser Thr Pro Asn Lys Asn Phe Leu Ala Pro Thr Phe Thr His Leu ---         277
```

FIG. 3C

```
841   aaa agg atg atc aaa aca cac agt gtt tag gtt gga atc ttt tgg aac tcc ttt gat ctc   900
901   act gtt att att aac att tat tta ttt ttc taa atg tga aag caa tac ata act tag       960
1021  gca tag aaa taa caa gag tta aca ttt tca tat ttt ctg tca gtc att ttt gta ttt       1080
1081  gtg gta tat gta tat atg tac cta tat gta ttt gca ttt gaa att ttg gaa tcc tgc tct   1140
1141  atg tac agt ttt gta tta tac ttt tta aat ctt gaa ctt tat gaa cat ttt ctg aaa tca   1200
1201  ttg att att cta caa aaa cat gat ttt aaa cag ctg taa aat att cta tga tat gaa tgt   1260
1261  ttt atg cat tat tta agc ctg tct cta ttg ttg gaa ttt cag gtc att ttc ata aat att   1320
1321  gtt gca ata aat atc atc ggg aat tg                                                1346
```

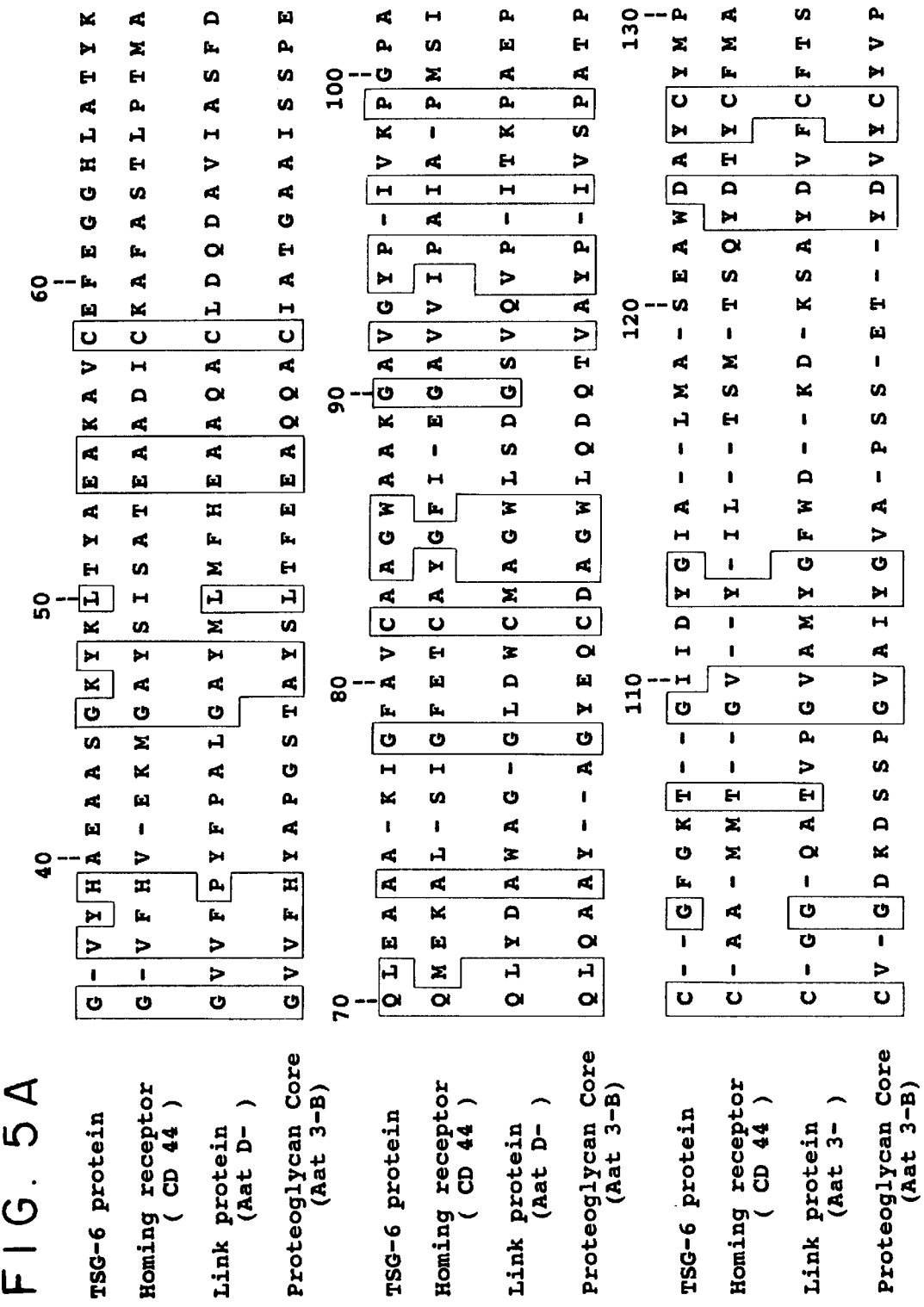

FIG. 5B

```
              140         150         160
TSG-6 protein        GGVFTDPKAIF---KSPGFPMEYEDMQICYWHIALK
Complement C1r       GGSIPIPQKLFGEVTSPLFPKPYPMMFETTVITVP
  A chain 170         180         190         200
TSG-6 protein        YGQAIHLSFLDFDLEDDPGCLADYVEIYDSYDDVHG
Complement C1r       TGYAVKLLVFQQFDLEPSEGCFYDYVKI--SADKK
  A chain 210         220         230         240
TSG-6 protein        FVGAVCGDELPDDIISTGHVMTLKFLSDASVTAGGF
Complement C1r       SLGAFCG-QLGSPLGMPPGKK--EFMSQGMKMLLTF
  A chain
```

DNA ENCODING TUMOR NECROSIS FACTOR STIMULATED GENE 6 (TSG-6)

CROSS-REFERENCE TO RELATED APPLICATIONS

The present application is a continuation-in-part of U.S. Ser. No. 08/024,868, filed Mar. 1, 1993, now Pat. No. 5,386,013, which is a continuation of U.S. Ser. No. 07/642,312, filed Jan. 14, 1991, now abandoned, the entire contents of said applications being entirely incorporated herein by reference.

BACKGROUND OF THE INVENTION

1. Field of the Invention

The invention relates to a protein, TSG-6, inducible in connective tissue cells by tumor necrosis factor or interleukin-1, DNA and mRNA encoding the TSG-6 protein, functional derivatives of the protein, antibodies specific to the protein, methods of producing the protein and DNA, and uses of the protein, DNA, mRNA, peptides and antibodies.

1. Description of the Background Art

Tumor necrosis factor (TNF) is a powerful pleiotropic cytokine important in host defenses against tumors and infectious agents. TNF has also been implicated in the pathology of some neoplastic diseases, infections and autoimmune disorders. Most biological actions of TNF can be attributed to the triggering of complex genetic programs in the target cells. Several genes activated by TNF have been identified but many more require characterization.

General Properties of TNF

TNF (also termed TNF-α and cachectin) is a protein produced by activated monocytes/macrophages which was originally detected in the serum of animals injected sequentially with a bacterial vaccine (bacillus Calmette-Guerin, BCG) and endotoxin (Carswell, E. A. et al., *Proc. Natl. Acad. Sci. USA* 72:3666 (1975)). TNF is structurally and functionally related to a cytokine produced by activated T lymphocytes which was originally termed lymphotoxin (LT) and is also known as TNF-β (Aggarwal, B. B. et al., *J. Biol. Chem.* 260:2334 (1985); Williams, T. W. et al., *Nature* 219:1076 (1968); Ruddle, N. H. et al., *J. Exp. Med.* 128:1267 (1968); Spies, T. et al., *Proc. Natl. Acad. Sci. USA* 83:8699 (1986); Gray, P. W. et al., *Nature* 312:721 (1984); Pennica, D. W. et al., *Nature* 312:724 (1984)). The genes encoding TNF and LT are linked, and are near the HLA-DR locus on the short arm of human chromosome 6 (Spies, T. et al., supra). TNF and LT bind to common cell surface receptors (Aggarwal, B. B. et al., *Nature* 318:665 (1985)).

Natural human TNF is a 157 amino acid, non-glycosylated protein with a molecular weight of approximately 17 kDa under denaturing conditions. The mature molecule is derived from a precursor (pre-TNF) which contains 76 additional amino acids at the N-terminus (Pennica, D. W. et al., supra). The expression of the gene encoding TNF is not limited to cells of the monocyte/macrophage family. Several human non-monocytic tumor cell lines were shown to produce TNF (Rubin, B. Y. et al., *J. Exp. Med.* 164:1350 (1986); Spriggs, D. et al., *Proc. Natl. Acad. Sci. USA* 84:6563 (1987)). TNF is also produced by CD4+ and CD8+ peripheral blood T lymphocytes, and by various cultured T and B cell lines (Cuturi, M. C., et al., *J. Exp. Med.* 165:1581 (1987); Sung, S.-S. J. et al., *J. Exp. Med.* 168:1539 (1988)).

Accumulating evidence indicates that TNF is a regulatory cytokine with pleiotropic biological activities. These activities include: inhibition of lipoprotein lipase synthesis ("cachectin" activity) (Beutler, B. et al., *Nature* 316:552 (1985)), activation of polymorphonuclear leukocytes (Klebanoff, S. J. et al., *J. Immunol.* 136:4220 (1986); Perussia, B., et al., *J. Immunol.* 138:765 (1987)), inhibition of cell growth or stimulation of cell growth (Vilcek, J. et al., *J. Exp. Med.* 163:632 (1986); Sugarman, B. J. et al., *Science* 230:943 (1985); Lachman, L. B. et al., *J. Immunol.* 138:2913 (1987)), cytotoxic action on certain transformed cell types (Lachman, L. B. et al., supra; Darzynkiewicz, Z. et al., *Canc. Res.* 44:83 (1984)), antiviral activity (Kohase, M. et al., *Cell* 45:659 (1986); Wong, G. H. W. et al., *Nature* 323:819 (1986)), stimulation of bone resorption (Bertolini, D. R. et al., *Nature* 319:516 (1986); Saklatvala, J., *Nature* 322:547 (1986)), stimulation of collagenase and prostaglandin E2 production (Dayer, J.-M. et al., *J. Exp. Med.* 162:2163 (1985)), and other actions. For reviews of TNF, see Beutler, B. et al., *Nature* 320:584 (1986), Old, L. J., *Science* 230:630 (1986), and Le, J. et al., *Lab. Invest.* 56:234 (1987).

TNF also has immunoregulatory actions, including activation of T cells (Yokota, S. et al., *J. Immunol.* 140:531 (1988)), B cells (Kehrl, J. H. et al., *J. Exp. Med.* 166:786 (1987)), monocytes (Philip, R. et al., *Nature* 323:86 (1986)), thymocytes (Ranges, G. E. et al., *J. Exp. Med.* 167:1472 (1988)), and stimulation of the cell-surface expression of major histocompatibility complex (MHC) class I and class II molecules (Collins, T. et al., *Proc. Natl. Acad. Sci. USA* 83:446 (1986); Pujol-Borrell, R. et al., *Nature* 326:304 (1987)).

TNF also has various pro-inflammatory actions which result in tissue injury, such as induction of procoagulant activity on vascular endothelial cells (Pober, J. S. et al., *J. Immunol.* 136, 1680, 1986)), increased adherence of neutrophils and lymphocytes (Pober, J. S. et al., *J. Immunol.* 138:3319 (1987)), and stimulation of the release of platelet activating factor (PAF) from macrophages, neutrophils and vascular endothelial cells (Camussi, G. et al., *J. Exp. Med.* 166:1390 (1987)). Recent evidence implicates TNF in the pathogenesis of many infections (Cerami, A. et al., *Immunol. Today* 9:28 (1988)), immune disorders (Piguet, P.-F. et al., *J. Exp. Med.* 166:1280 (1987)), and in cachexia accompanying some malignancies (Oliff, A. et al., *Cell* 50:555 (1987)). Michie, H. R. et al., *Br. J. Surg.* 76:670–671 (1989), reviewed evidence that TNF is the principal mediator associated with the pathological changes of severe sepsis.

TNF also has activity associated with growth and differentiation of hemopoietic precursor cells (Murphy, M. et al., *J. Exp. Med.* 164:263 (1986); Broxmeyer, H. E. et al., *J. Immunol.* 136:4487 (1986)); some of these actions may be indirect, and are thought to be mediated through the stimulation of production of granulocyte-macrophage colony stimulating factor (GM-CSF) (Munker, R. et al., *Nature* 323:79 (1986)) and other hemopoietic growth factors (Zucali, J. R. et al., *J. Immunol.* 140:840 (1988)).

Regulation of Gene Expression by TNF

It is, therefore, apparent that TNF is an extremely "versatile" and clinically significant cytokine. Most of its actions are likely to be mediated by the activation or inactivation of specific genes in the cells upon which it acts. One exception to this mode of action is the rapid cytotoxic effect of TNF on certain target cells; this effect is augmented by inhibitors of RNA or protein synthesis and does not appear to depend on the modulation of gene expression (Matthews, N., *Br. J. Cancer* 48:405 (1983)). Many specific gene products have been shown to be up-regulated in TNF-treated cells, some of which are discussed below.

Among the first examples of TNF-modulated gene expression was the demonstration that TNF treatment induced an increase in MHC class I mRNA levels and in surface expression of the MHC class I glycoproteins in human vascular endothelial cells (HUVEC) and normal skin fibroblasts (Collins, T. et al., supra). A partial list of other molecules (or genes) induced by TNF appears in Table 1, below. It is interesting to note that TNF is an autoregulatory cytokine, since exogenously added TNF increases TNF synthesis in monocytes and monocytic cell lines (Philip, R. et al., Nature 323:86 (1986); Schmid, J. et al., J. Immunol. 139:250 (1987)).

TABLE 1

GENES AND PROTEINS INDUCED BY TUMOR NECROSIS FACTOR

| Protein or Gene | Cell Type | |
|---|---|---|
| Leukocyte adhesion protein H4/18 | HUVEC | (1) |
| Platelet-derived growth factor (PDGF) | HUVEC and some tumor cell lines | (2) |
| IL-6 (IFN-β2 or BSF-2) | Human skin fibroblasts | (3) |
| HLA-DR | Human tumor cell lines | (4) |
| Collagenase | Synovial cells and skin fibroblasts | (5) |
| 2'-5' oligoadenylate synthetase | Tumor cell lines | (6) |
| c-myc and c-fos oncogenes | Human skin fibroblasts | (7) |
| Epidermal growth factor receptor | Human skin fibroblasts | (8) |
| Tissue factor | HUVEC | (9) |
| ICAM-1 and ELAM-1 | HUVEC | (10) |
| Plasminogen activator inhibitors 1 and 2 (PAI-1 and PAI-2) | HT1080 cell line | (11) |
| Synthesis of 36 kDa and 42 kDa (=PAI-2) proteins. | Human skin fibroblasts | (12) |
| Superoxide Dismutase (MnSOD) gene | Human tumor cell lines | (13) |
| IL-1α and IL-1β genes | Human skin fibroblasts | (14) |

REFERENCES: 1. Pober, J. S. et al., J. Immunol. 136, 1680, 1986. 2. Hajjar, K. A. et al., J. Exp. Med. 166, 235, 1987. 3. Kohase, M. et al., Cell 45:659 (1986). 4. Pfizenmaier, K. et al. J. Immunol. 138, 975, 1987. 5. Dayer, J. -M. et al., J. Exp. Med. 162:2163 (1985). 6. Wong, G. H. W. et al., Nature 323:819 (1986). 7. Lin, J. -X. et al., J. Biol. Chem. 262, 11908, 1987. 8. Palombella, V. J. et al., J. Biol. Chem. 262, 1950, 1987. 9. Edgington, T. S. et al., Abs. 2nd Internat. Conf. TNF, p. 4, 1989. 10. Bevilacqua, M. P. et al., Proc. Natl. Acad. Sci. USA 84, 9238, 1987. 11. Medcalfe, R. L. et al., J. Exp. Med. 168, 751, 1988. 12. Kirstein, M. et al., J. Biol. Chem. 261, 9565, 1986. 13. Wong, G. H. et al., Science 242, 941, 1988. 14. Le, J. et al. Lab. Invest. 56:234 (1987).

The inhibitory actions of TNF on gene expression are less well-characterized. TNF was shown to inhibit c-myc expression in cells whose growth it inhibited (Kronke, M. et al., Proc. Natl. Acad. Sci. USA 84:469 (1987)). Collagen synthesis was inhibited in human fibroblasts (Solis-Herruzo et al., J. Biol. Chem. 263:5841 (1988)), and thrombomodulin in HUVEC (Conway, E. M. et al., Molec. Cell. Biol. 8:5588 (1988)). All these inhibitory actions were expressed at the level of transcription, but the precise mechanisms are still unclear.

The mechanisms of signal transduction and gene activation by TNF are the subject of great interest. In many cell types, TNF activates a phospholipase (most likely PLA2), resulting in the liberation of arachidonic acid from cellular pools (Suffys, P. et al., Biochem. Biophys. Res. Comm. 149:735 (1987)) and increased eicosanoid synthesis (Dayer, J.-M. et al., supra). In human fibroblasts, TNF stimulated GTPase activity (Imamura, K. et al. J. Biol. Chem. 263:10247 (1989)), raised cAMP levels, enhanced cAMP-dependent protein kinase activity, and activated protein kinase C (PKC) (Zhang, Y. et al., Proc. Natl. Acad. Sci. USA 85:6802 (1988); Brenner, D. A. et al., Nature 337:661 (1989)). TNF can also activate the transcription factor NF-kB, which appears to be the mechanism by which TNF induces the IL-2 receptor a chain (Lowenthal, J. W. et al., Proc. Natl. Acad. Sci. USA 86:2231 (1989)) or cause activation of latent human immunodeficiency virus, HIV-1 (Griffin, G. E. et al., Nature 339:70 (1989)).

Interactions of TNF with other Cytokines

When the individual actions of TNF-α, TNF-β, IL-1α, IL-1β, IFN-α, IFN-β or IFN-τ are compared in various experimental systems, a great deal of apparent redundancy and ambiguity is noted. First, structurally related cytokines which utilize the same receptor (e.g., TNF-α and TNF-β; IL-1α and IL-1β; IFN-α and IFN-β) act similarly. More surprisingly, structurally unrelated cytokines which bind to different receptors also have similar physiological effects. For example, IL-1 and TNF have similar gene activating activities, and result in similar biological effects (Le, J. et al. Lab. Invest. 56:234 (1987)). IFNs and TNF also share biological activities (Kohase, M. et al., Cell 45:659 (1986); Wong, G. H. W. et al., Nature 323:819 (1986); Williamson, B. D. et al., Proc. Natl. Acad. Sci. USA 80:5397 (1983); Stone-Wolff, D. S. et al., J. Exp. Med. 159:828 (1984)). For example, IFNs and TNF activate some of the same genes, including MHC class I and class II genes, 2'–5' oligoadenylate synthetase, IL-6, the transcription factor IRF-1, and the TNF gene itself (Vilcek, J., Handbook of Experimental Pharmacology, Vol. 95/II, p. 3, Springer-Verlag, Berlin (1990)).

Under natural conditions, cells are rarely, if ever, exposed to a single cytokine. Rather, cytokine action in vivo is "contextual," as has been postulated for growth factors (Sporn, M. B. et al., Nature 332:217 (1988)). The biological effects produced by cytokines under natural conditions must therefore represent the sum of the synergistic and antagonistic interactions of all cytokines present simultaneously in a given microenvironment. In addition, cytokines appear to be arranged in "networks" and "cascades", such that the synthesis of one cytokine can be positively or negatively regulated by another. For these reasons, it is important to understand the molecular mechanisms of action of cytokines acting individually as well as in combination.

In contrast to the above, there are cases in which the actions of TNF and IFNs are antagonistic rather than similar or synergistic. For example, TNF is mitogenic for human diploid fibroblasts, whereas IFNs inhibit growth of these cells (Vilcek, J. et al., J. Exp. Med. 163:632 (1986)). The cellular response to a combination of TNF and an IFN can differ from the response to either one alone, both qualitatively and quantitatively (Leeuwenberg, J. F. M. et al., J. Exp. Med. 166:1180 (1987); Reis, L. F. L. et al., J. Biol. Chem. 264:16351 (1989); Feinman, R. et al., J. Immunol. 136:2441 (1986); Trinchieri, G. et al., Abstr. 2nd Int'l Conf. TNF, p. 7 (1989)). To make matters even more complicated, in some cells TNF can induce IFN-β synthesis (Reis et al., supra); the activation of some genes (e.g., HLA class I) by TNF requires the presence of IFN-β (Leeuwenberg et al., supra). Since IFNs and TNF-α and TNF-β are often produced in the same microenvironment in response to a similar set of stimuli (Murphy, M. et al., supra; Stone-Wolff et al., supra; Billiau, A., Immunol. Today 9:37 (1988)), it is clear that the interactions of TNF and IFNs are highly relevant to the outcome in vivo under either "normal" or pathophysiological conditions.

The association of cytokines, in particular TNF, with cancer and infectious diseases takes many forms often related to the host's catabolic state. One of the major and most characteristic problems seen in cancer patients is weight loss, usually associated with anorexia. The extensive wasting which results is known as "cachexia" (see, for review, Kern, K. A. et al. (J. Parent. Enter. Nutr. 12:286–298 (1988)). Cachexia includes progressive weight loss, anorexia, and persistent erosion of body mass in response to a malignant growth. The fundamental physiological derangement may be related to a decline in food intake relative to energy expenditure. The causes for this commonly observed and often life-limiting disturbance remain to be determined, even though many contributing factors have been identified (Braunwald, E. et al. (Eds.), Harrison's PRINCIPLES OF INTERNAL MEDICINE, 11th Ed., McGraw-Hill Book Co., New York, 1987, Chap. 78, pp. 421–431). The cachectic state is associated with significant morbidity and is responsible for the majority of cancer mortality. A number of studies have suggested that TNF is an important mediator of the cachexia in cancer, infectious disease, and in other catabolic states.

It has been known for some time that in bacterial infection, sepsis and critical illness, bacterial lipopolysaccharides (LPS), or endotoxins, are responsible for many of the pathophysiological manifestations, including fever, malaise, anorexia, and cachexia. More recently, it was observed that TNF can mimic many endotoxin effects, leading to the suggestion that TNF, and related cytokines derived from cells of the macrophage/monocyte family, in particular, IL-1, are central mediators responsible for the clinical manifestations of the illness. Endotoxin is a potent monocyte/macrophage activator which stimulates production and secretion of TNF (Kornbluth, S. K. et al., *J. Immunol.* 137:2585–2591 (1986)) and other cytokines including IL-1 (Dinarello, C. A., *Rev. Infec. Dis.* 6:51–94 (1984)), interleukin-6 (IL6), and colony stimulating factor (CSF) (Apte, R. N. et al. *J. Cell. Physiol.* 89:313 (1976)). Some of these cytokines further stimulate T lymphocytes to produce additional cytokines, for example, interleukin-2 (IL-2) (Robb, R. J., *Immunol. Today* 5:203–209 (1984)).

The monocyte-derived cytokines are thought to be important mediators of the metabolic and neurohormonal responses to endotoxin (Michie, H. R. et al., *N. Eng. J. Med.* 318:1481–1486 (1988)), and in cancer and other catabolic states (Norton, J. A. et al., *Nutrition* 5:131–135 (1989)). Interestingly, some changes induced by low-dose TNF closely resemble changes provoked by high dose IL2 (Remick, D. G. et al., *Lab. Invest.* 56:583–590 (1987)).

Endotoxin administration to human volunteers produced acute illness with flu-like symptoms including fever, tachycardia, increased metabolic rate and stress hormone release (Revhaug, A. et al., *Arch. Surg.* 123:162–170 (1988)). Treatment of cancer patients (having normal kidney and liver function) with escalating doses of TNF (4–636 $\mu g/m^2$/24 hr) indicated that doses greater than 545 $\mu g/m^2$/24 hr caused alterations similar to those induced by injection of endotoxin (4 ng/kg) into healthy humans (Michie, H. R. et al., *Surgery* 104:280–286 (1988)), leading the authors to conclude that TNF is the principal host mediator of septic and endotoxemic responses. More recently, it was shown that five days of chronic intravenous TNF infusion into humans or rats was associated with anorexia, fluid retention, acute phase responses, and negative nitrogen balance (i.e., classic catabolic effects), leading to the conclusion that TNF may be responsible for many of the changes noted during critical illness (Michie, H. R. et al., *Ann. Surg.* 209:19–24 (1989)). Administration of rTNF to cancer patients also led to a rise in C-reactive protein (CRP) and a fall in serum zinc, a large increase in forearm efflux of total amino acids, and amino acid uptake by other tissues (Warren, R. S. et al., *Arch. Surg.* 122:1396–1400 (1987)), considered further evidence for a role of TNF in cancer cachexia.

Citation of any document herein is not intended as an admission that such document is pertinent prior art, or considered material to the patentabilty of any claim of the present application. Any statement as to content or a date of any document is based on the information available to applicant at the time of filing and does not constitute an admission as to the correctness of such a statement.

SUMMARY OF THE INVENTION

Cytokines such as TNF and IL-1 play a major role in the mediation of inflammatory responses as well as in host responses to infections and cancer. The mode of action of these cytokines is only beginning to be understood. The present inventors have discovered and studied a series of proteins and glycoproteins induced in connective tissue cells by such cytokines. As a result of these studies, the present inventors have conceived of the use of such cytokine-induced proteins or glycoproteins, termed TSG proteins, or functional derivatives such as peptides derived therefrom, and antibodies specific for these TSG proteins/glycoproteins, for a number of diagnostic and therapeutic procedures. These proteins, the DNA coding therefor, and the functional derivatives thereof, are useful in a number of diseases associated with action of the above types of cytokines, including chronic inflammatory conditions, in particular rheumatoid arthritis, in infections and sepsis, and in cancer.

Specifically, the present invention provides a cytokine-induced protein or glycoprotein molecule, termed TSG-6, or a functional derivative thereof, wherein, when the protein molecule is one which naturally occurs, it is substantially free of other proteins or glycoproteins with which it is natively associated. The full length protein molecule has an apparent molecular weight of about 32 kDa or 35 kDa and has the amino acid sequence SEQ ID NO:2 or as presented in Table 2. In a glycosylated form, the glycoprotein may have molecular weights in the range of about 35 kDa or 38–41 kDa.

The present invention is further directed to a DNA molecule encoding TSG-6 or a functional derivative thereof, wherein, when the DNA molecule occurs naturally, it is substantially free of other nucleotide sequences with which it is natively associated, in particular its adjoining sequences. In a preferred embodiment, the DNA molecule has the nucleotide sequence SEQ ID NO:1. The DNA molecule of the present invention may be genomic DNA or cDNA and it may be single stranded or double stranded.

The present invention provides the DNA molecule as an expression vehicle, such as a plasmid, and provides host cells transformed or transfected with the DNA molecule. Hosts may be bacteria or eukaryotic cells, including yeast and mammalian cells.

Also included in the present invention is a process for preparing the TSG-6 protein or glycoprotein molecule substantially free of other proteins or glycoproteins with which it is natively associated, or a functional derivative thereof, comprising: (a) culturing a host cell capable of expressing the protein under culturing conditions, (b) expressing the protein or functional derivative; and (c) recovering the protein or functional derivative from the culture.

The present invention is further directed to an antibody specific for the TSG-6 protein or an epitope thereof. A preferred antibody is a monoclonal antibody.

Also provided is a method for detecting the presence of TSG-6 protein in a biological sample, comprising: (a) contacting the biological sample that is suspected of containing TSG-6 protein with a molecule capable of binding to the protein; and (b) detecting any of this molecule bound to the protein. For this method, a preferred molecule is an antibody or antibody fragment, most preferably a monoclonal antibody, and the preferred detection method is an immunoassay.

The present invention further includes a method for detecting the presence of nucleic acid encoding a normal or mutant TSG-6 protein in a subject comprising: (a) contacting a cell obtained from the subject, an extract thereof, or a culture supernatant thereof, with an oligonucleotide probe encoding at least a portion of the normal or mutant TSG-6 under hybridizing conditions; and (b) measuring the hybridization of this probe to the nucleic acid of the cell, thereby detecting the presence of the nucleic acid. This method may additionally include, before step (a), selectively amplifying the amount of DNA of the cell encoding the TSG-6 protein.

The present invention is still further directed to a method for measuring induction of expression of TSG-6 in a cell, comprising: (a) contacting the cell with a substance capable of inducing expression of TSG-6; (b) measuring the amount of mRNA encoding TSG-6 in the cell by hybridization with an oligonucleotide probe encoding at least a portion of TSG-6, under hybridizing conditions; and (c) comparing the amount of TSG-6 mRNA in the cell with the amount of TSG-6 mRNA in the cell, not contacted with the inducing substance, wherein an increase in the amount of the TSG-6 mRNA indicates that the induction has occurred.

An alternative method for measuring induction of expression of TSG-6, according to the present invention, comprises: (a) contacting the cell with a substance capable of inducing expression of TSG-6; (b) measuring the amount of TSG-6 protein in an extract or supernatant of the cell using the method described above for measuring the TSG-6 protein, preferably, an immunoassay; (c) comparing the amount of TSG-6 protein in the cell extract or supernatant with the amount of TSG-6 protein in the extract or supernatant of a cell not contacted with the inducing substance, wherein an increase in the amount of the TSG-6 protein indicates that the induction has occurred.

The present invention may also be used in a method for identifying a compound capable of inducing the expression of TSG-6 in a cell, comprising: (a) contacting the cell with the compound being tested; and (b) measuring the induction of TSG-6 mRNA according to one of the two methods described above, thereby identifying the compound.

The present invention provides a method for measuring the ability of a cell to respond to TNF or to IL-1, comprising: (a) contacting the cell with an amount of TNF capable of inducing expression of the TSG-6 gene in FS-4 cells; and (b) determining the induction of expression of TSG-6 mRNA or protein using either of the methods described above, thereby measuring the ability of the cell to respond to TNF.

BRIEF DESCRIPTION OF THE DRAWINGS

FIGS. 1A–1H depict Northern blots showing induction of mRNAs corresponding to eight TSG cDNAs in FS-4 cells treated with TNF. Growth-arrested FS-4 cells were exposed to TNF (20 ng/ml) at 0 h. At different intervals thereafter, total cell RNA was isolated, fractionated on formaldehyde-agarose gels, transferred to Zeta-probe blotting membranes, and hybridized separately to each of the $^{32}$P-labeled TSG cDNA inserts. To ascertain whether equal amounts of RNA were loaded in each lane, most blots were also probed with a $^{32}$P-labeled pHe7 internal reference cDNA insert specific for an invariant mRNA species of about 1.0 kb.

FIGS. 2A–2H are a series of graphs showing the kinetics of induction of eight TSG mRNAs by TNF. Autoradiograms of the Northern blots shown in FIGS. 1A–1H were scanned by laser densitometry. For each individual mRNA, the highest-density band was normalized to represent 100% induction.

FIGS. 3A–3C show the nucleotide sequence (SEQ ID NO:1) and deduced amino acid sequence (SEQ ID NO:2) of TSG-6 cDNA. Nucleotide and amino acid residues are numbered from the first methionine of the major open reading frame. The putative signal sequence is underlined (thick line). Potential glycosylation sites for N-linked glycans are shown by double broken lines. Potential chondroitin sulfate linkage site and consensus sequence are shown by star with single broken line. Also marked are the mRNA decay consensus sequence motifs ATTTA (thin line) (Shaw, G. et al., Cell 46:659 (1986)) and the polyadenylation signal (^^^^) are underscored.

FIGS. 5A–5B show, in FIG. 5A, the alignment of the putative amino acid sequence of TSG-6 corresponding to amino acid residues 36–130 of SEQ ID NO:2 with the published sequences of human lymphocyte homing receptor CD44/Hermes, (SEQ ID NO:3) rat cartilage link protein (SEQ ID NO:4) and rat proteoglycan core protein (SEQ ID NO:5). The numbering of amino acid residues corresponds to the putative TSG-6 protein sequence. Note that cysteines in positions 58, 82, 103 and 127 are conserved in all four sequences. FIG. 5B shows the alignment of the C-terminal portion of TSG-6 (amino acids 136 to 240 of SEQ ID NO:2) with the α-fragment of complement component, C1r (SEQ ID NO:6).

FIG. 6A represents the TrpE/TSG-6 fusion protein expression vector, pATH-TSG-6. FIG. 6B represents the MS2/TSG-6 fusion protein expression vector, pEX-TSG-6.

FIG. 10A shows blots of cells transfected with pSV-TSG-6. FIG. 10B shows blots of cells transfected with pMAMneo-TSG-6.

FS-4: normal human diploid foreskin fibroblasts;

GM-637: SV40-transformed diploid fibroblast cell line;

U937: human macrophage-like cell line from histiocytic lymphoma;

A673: human rhabdomyosarcoma cell line;

HUVEC: human umbilical vein endothelial cells;

A549: human lung carcinoma cell line;

Colo205: human colon adenocarcinoma cell line;

HT29: human colon adenocarcinoma cell line;

MEL: SK-MEL-19, cutaneous malignant melanoma cell line.

Figure 12A:
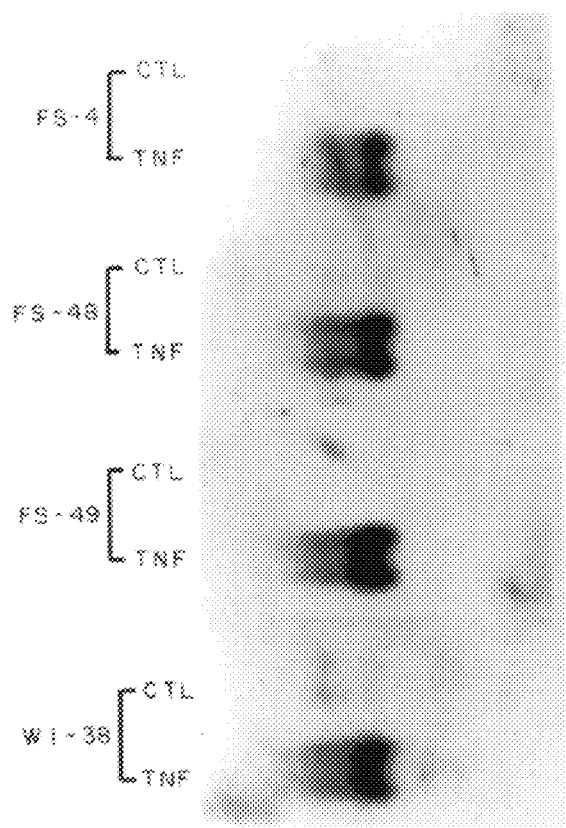
Figure 12B:
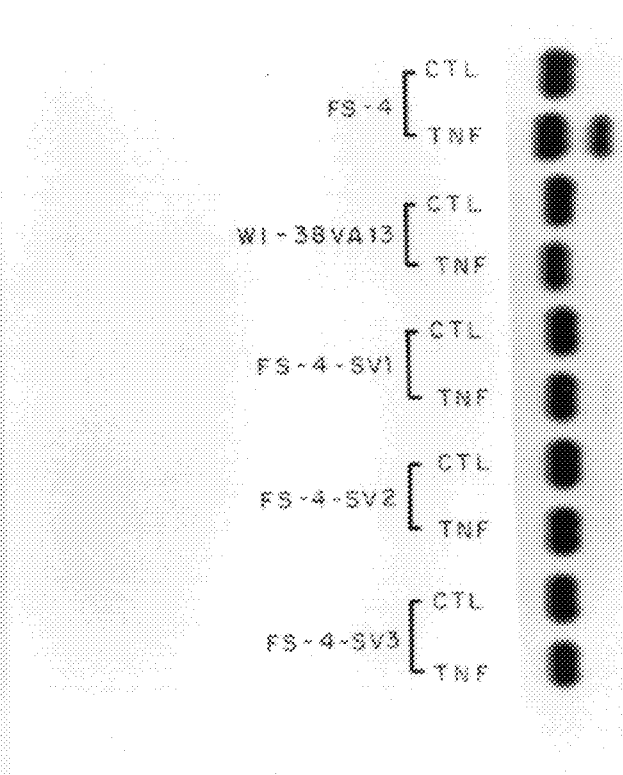

FIGS. 12A–12B show a Northern blot analysis of TNF induction of TSG-6 mRNA in fibroblasts and transformed fibroblast lines. TNF (20 ng/ml) was added to confluent cells. Total RNA was extracted and subjected to Northern blot analysis. FS-48 and FS-49 are normal human diploid foreskin fibroblasts from different donors. WI-38 is a normal human diploid fetal lung fibroblast line. WI-38 VA13 is SV40-transformed WI-38 cell line. FS-4(SV1), FS-4(SV2) and FS-4(SV3) are FS-4 cells immortalized by lipofection with a pSV3-neo plasmid containing DNA encoding the SV40 large T antigen.

Figure 13A:
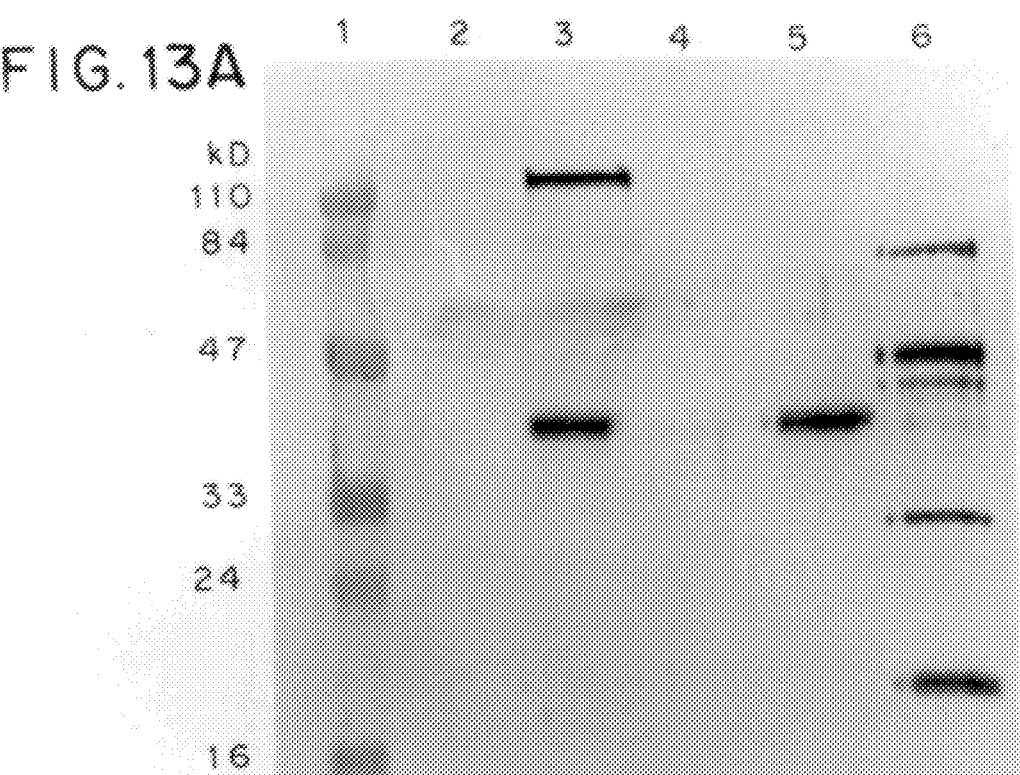
Figure 13B:
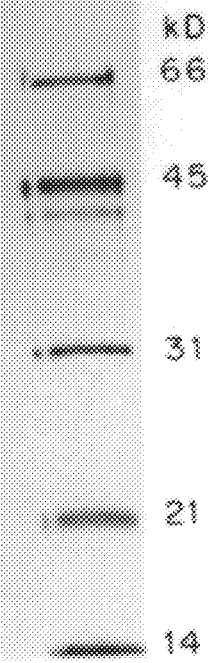

FIGS. 13A–13B show a Western blot of concentrated supernatants of serum-free cultures of FS-4 cells or transfected GM-637 cells. In FIG. 13A, bands were developed using anti-TSG-6 antibody purified by immunoaffinity chromatography. In FIG. 13B, bands were developed with similarly purified pre-immune serum from the same rabbit.

Lane 1: prestained molecular weight standards;

Lane 2: supernatant of GM-637 cells transfected with pRSVneo (GN4);

Lane 3: supernatant of GM-637 cells transfected with TSG-6 cDNA (GSV-L5);

Lane 4: supernatant of untreated FS-4 cells;

Lane 5: supernatant of FS-4 cells after 24 hr induction with TNF (20 ng/ml);

Lane 6: biotinylated molecular weight standards.

Figure 14:
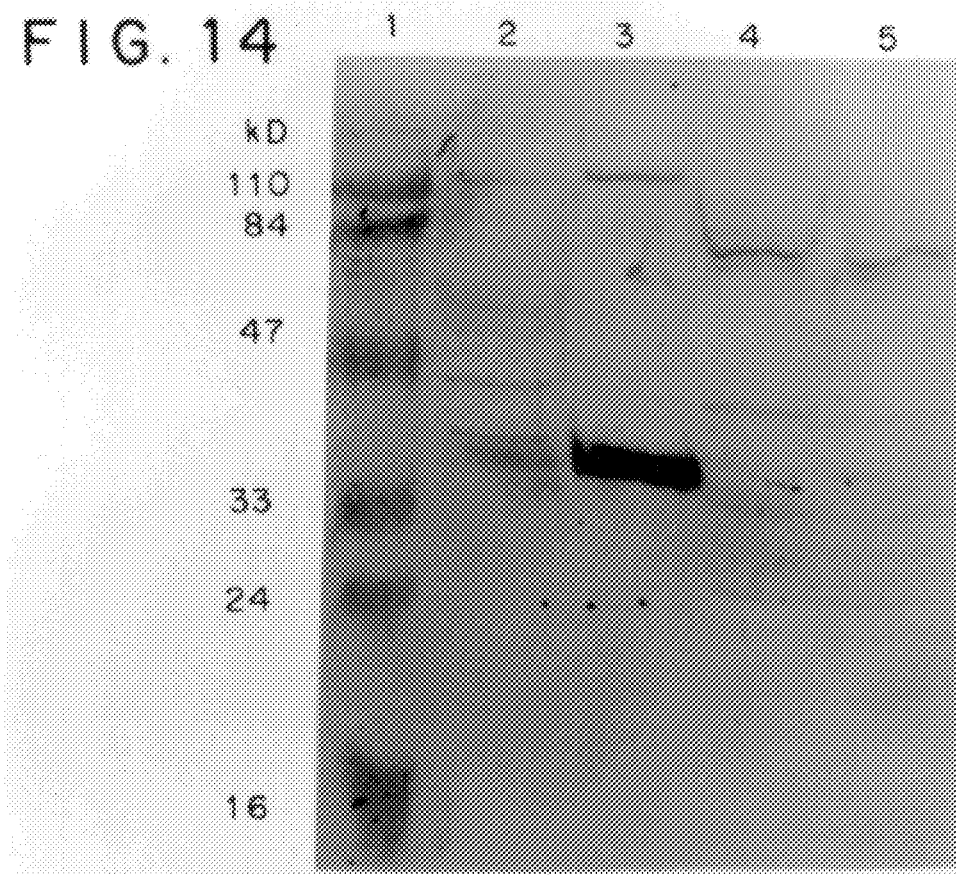

FIG. 14 is a Western blot pattern showing that TSG-6 protein is detectable in culture supernatants of GSV-15 cells, but not in cell lysates. Supernatants of serum-free cultures of TSG-6 cDNA-transfected GM-637 cells (GSV-L5 cells) and control-transfected GSV-neo cells were concentrated about 100-fold. To prepare lysates, cells were directly lysed in SDS-PAGE sample buffer. The samples were then subjected to Western blot analysis using affinity-purified anti-TSG-6 antibody. Lane 1: prestained molecular weight standards; lane 2: concentrated supernatant of GSV-neo cells; lane 3: concentrated supernatant of GSV-L5 cells; lane 4: lysate of GSV-neo cells; lane 5: lysate of GSV-L5 cells.

Figure 15:
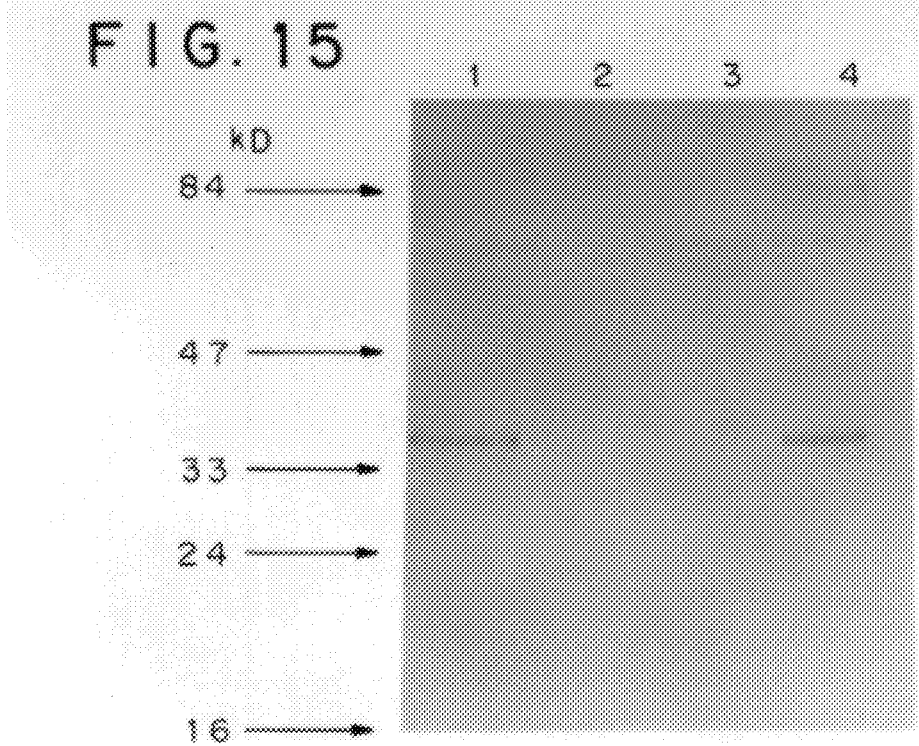

FIG. 15 is a Western blot pattern showing the binding of TSG-6 protein to hyaluronic acid (HA) coupled to Sepharose. The concentrated supernatant of GSV-L5 cells (serum-free) was incubated either with control Sepharose (DEC-activated, acetic acid-blocked) (lanes 1, 2) or HA-Sepharose (lanes 3, 4) in a batch procedure. The supernatants (lanes 1, 3) as well as the eluates (lanes 2, 4) were analyzed by Western blot with anti-TSG-6 antibody. Lane 1: supernatant after absorption on control Sepharose; lane 2: eluate from the control Sepharose; lane 3: supernatant after absorption on HA-Sepharose; lane 4: eluate from HA-Sepharose.

Figure 16:
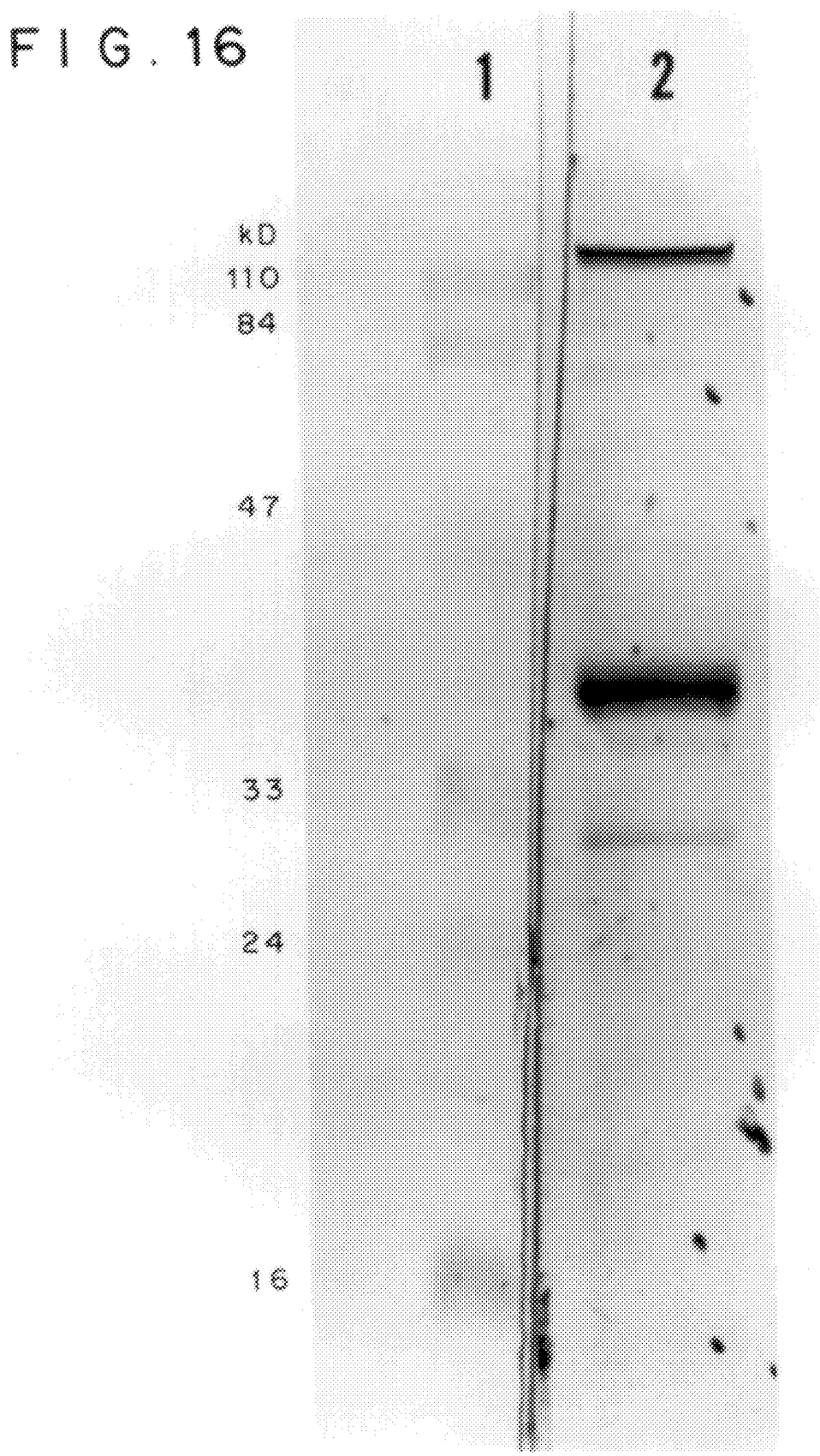

FIG. 16 shows a Western blot analysis of TSG-6 protein eluted from a hyaluronic acid (HA)-Sepharose column. Unconcentrated supernatants of GSV-L5 cells cultured in medium with 10% fetal calf serum was absorbed to a column of HA-Sepharose and eluted with Tris-HCl, pH 8.5, high salt buffer. The eluate was analyzed by Western blot with affinity-purified anti-TSG-6 antibody.

Figure 17:
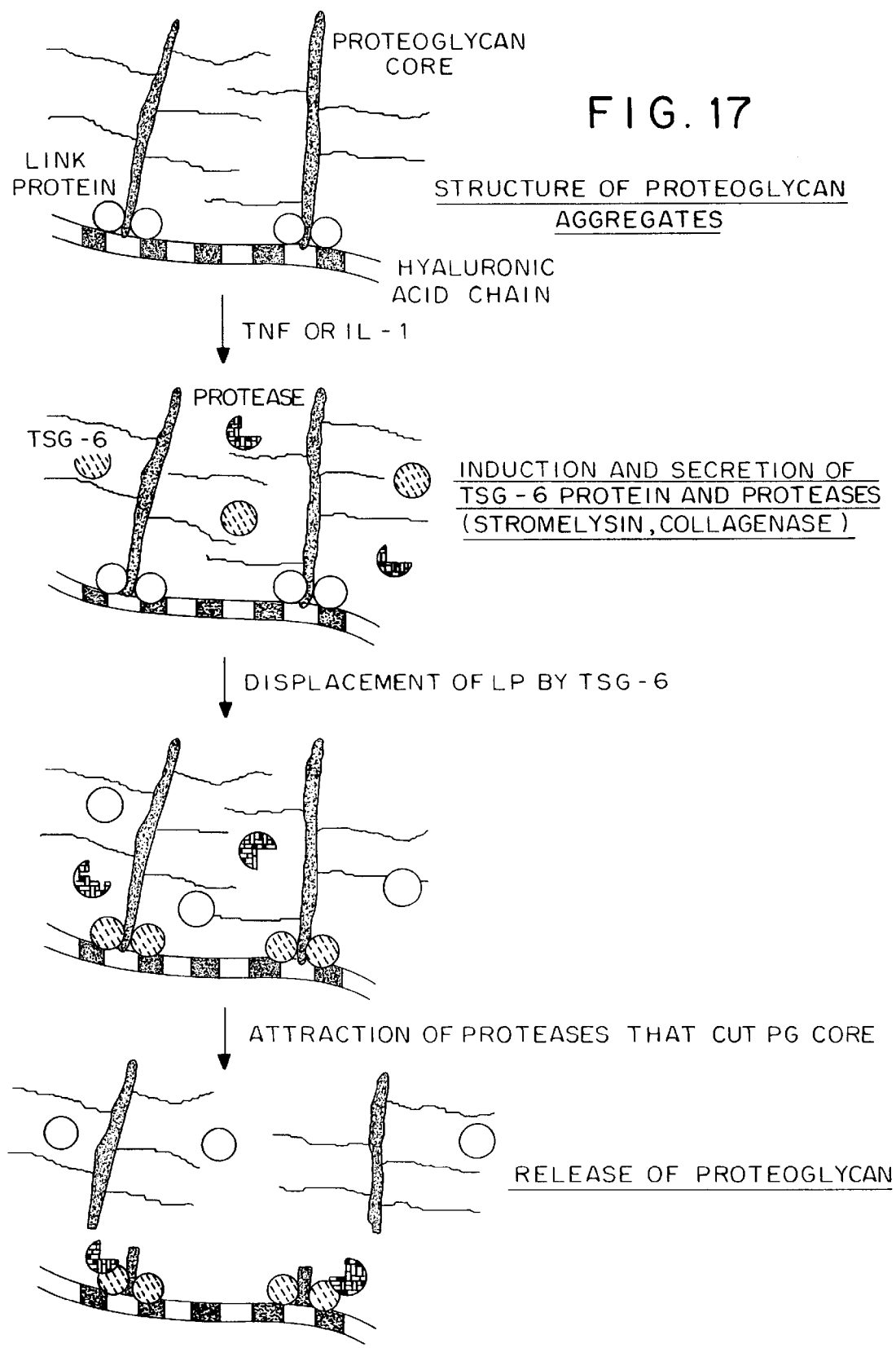

FIG. 17 depicts a hypothetical model for the involvement of TSG-6 in the release of proteoglycan in cartilage chondrocytes.

Figure 18:
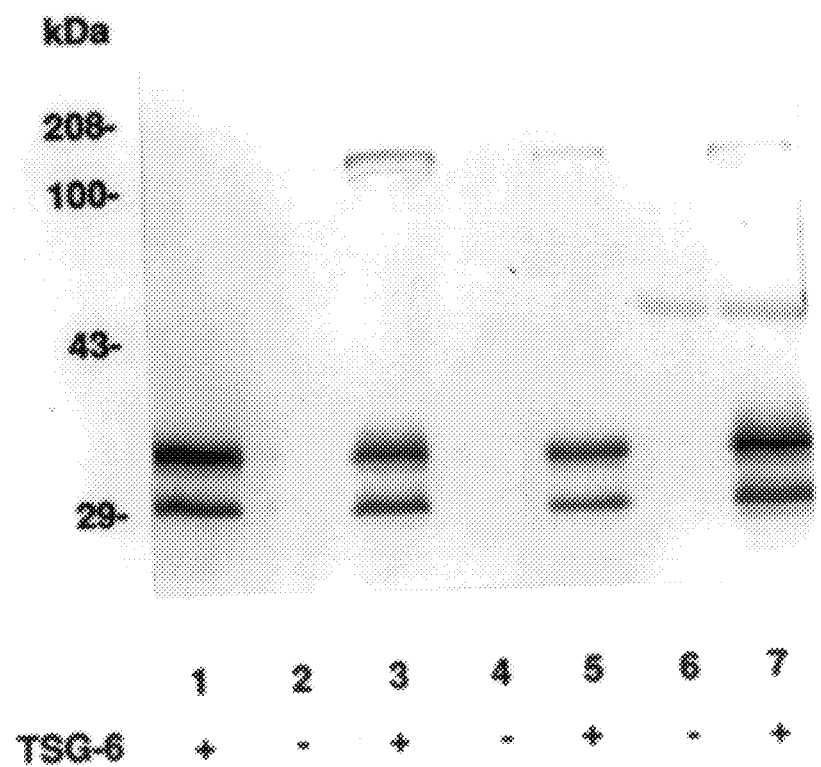

FIG. 18 shows that TSG-6 forms a stable complex with a serum protein. Fetal bovine serum (lanes 2, 3), serum-free supernatants of human HepG2 cells (lanes 4, 5), or mouse serum (lanes 6, 7) was incubated in the absence (lanes 2, 4, 6) or presence (lanes 3, 5, 7) of recombinant human TSG-6 for 1 hr. at 37° C. All samples were then subjected to Western blot analysis with rabbit antiserum to TSG-6. Lane 1 is a TSG-6 control. The lower (29 kDa) TSG-6 band represents nonglycosylated protein present in variable amounts in preparations of TSG-6 protein form insect cells infected with recombinant Baculovirus.

Figure 19:
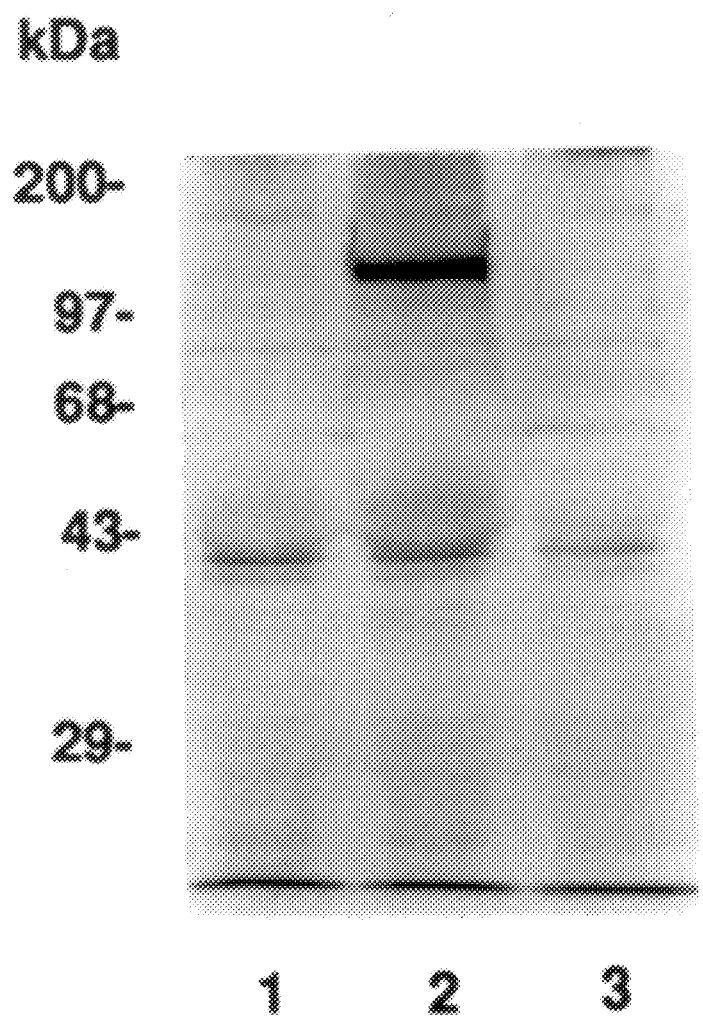

FIG. 19 shows immunoprecipitation of a $^{35}$S-labeled 120-kDa protein complex by anti-TSG-6 antiserum. $^{35}$S-labeled HepG2 culture supernatant was preincubated for 1 hr. at 37° C. with (lanes 2, 3) or without (lane 1) unlabeled purified recombinant TSG-6 protein and precipitated with rabbit anti-TSG-6 immune serum (lanes 1, 2) or preimmune serum (lane 3) from the same rabbit. The samples were then analyzed by SDS-PAGE in a 10% PAA gel and fluorography.

Figure 20:
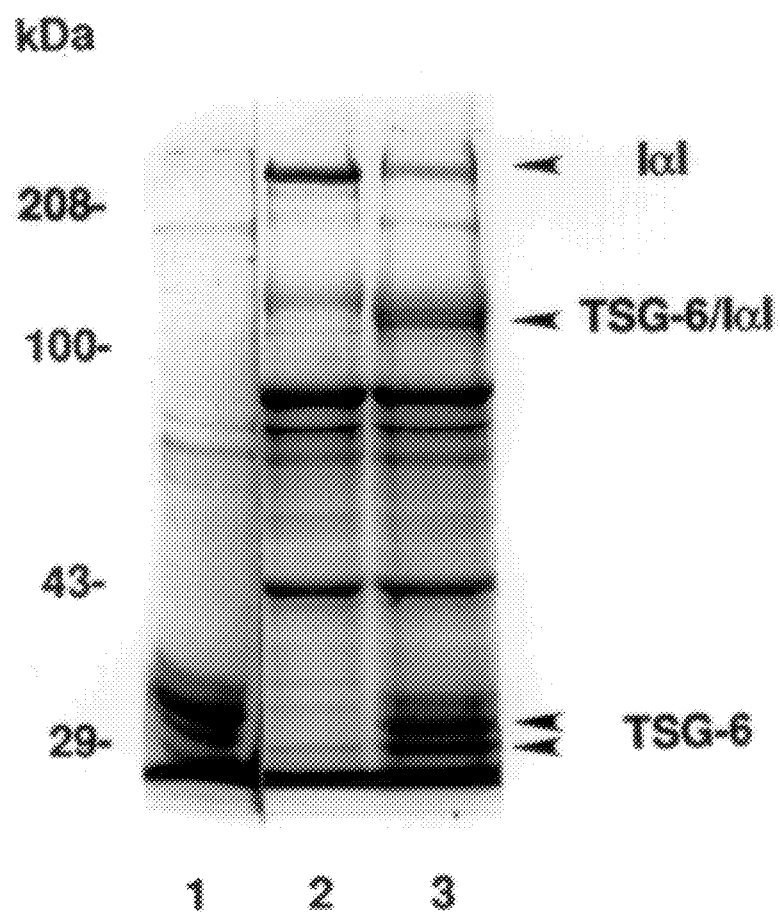
Figure 21:
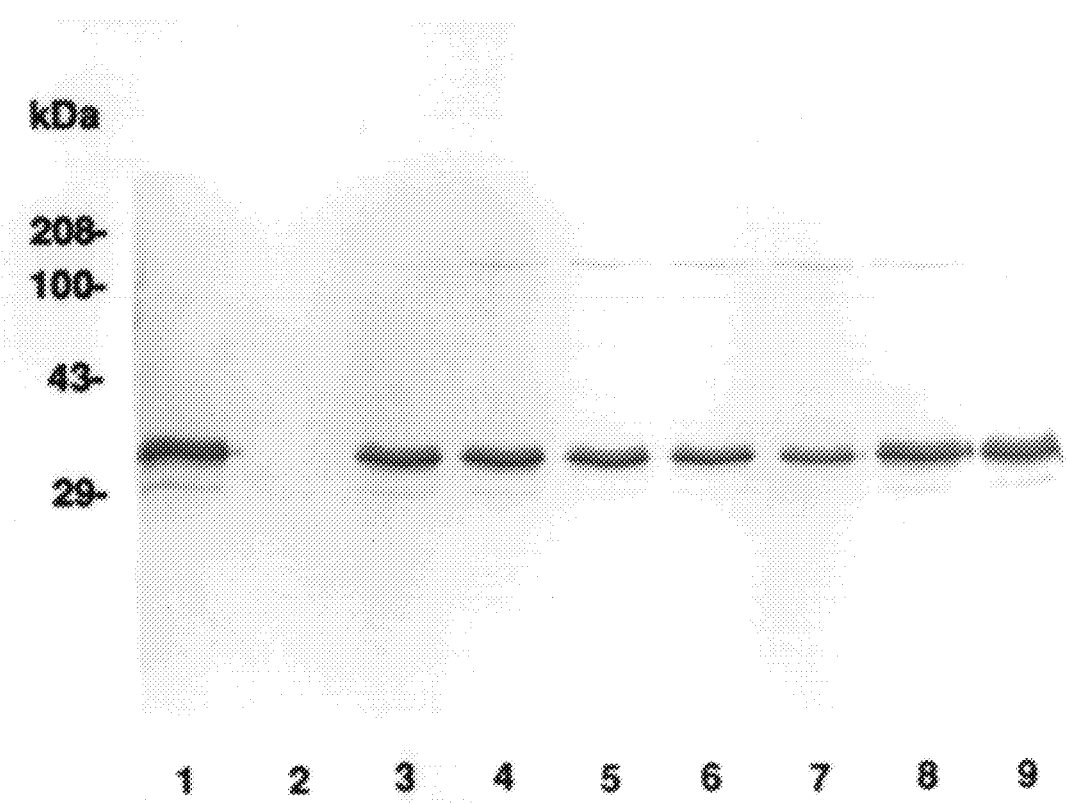

FIG. 20 shows changes in the band pattern of a fraction of human serum proteins after incubation with purified TSG-6 protein. A partially purified preparation of TSG-6 binding protein from human serum (after fractioned ammonium sulfate precipitation, Affini-filter chromatography, and FPLC on MonoQ) was incubated in the absence (lane 2) or presence (lane 3) of purified TSG-6 protein at 37° C. for 1 hr. Lane 1 is a TSG-6 control. The samples were separated by SDS-PAGE in a 10% PAA gel under reducing conditions and silver-stained FIG. 21 shows time course and temperature dependence of the formation of the TSG-6/IαI complex. Purified recombinant TSG-6 protein (lane 1) and IαI purified from human serum (lane 2) were mixed and incubated for 2 min. (lane 3), 5 min. (lane 4), 10 min. (lane 5), 15 min. (lane 6), 30 min. (lane 7), or for 60 min. (lane 8) at 37° C. or for 60 min. at 0° C. (lane 9). The reaction mixtures were then separated by SDS-PAGE and subjected to Western blot analysis with rabbit anti-TSG-6 serum.

Figure 22:
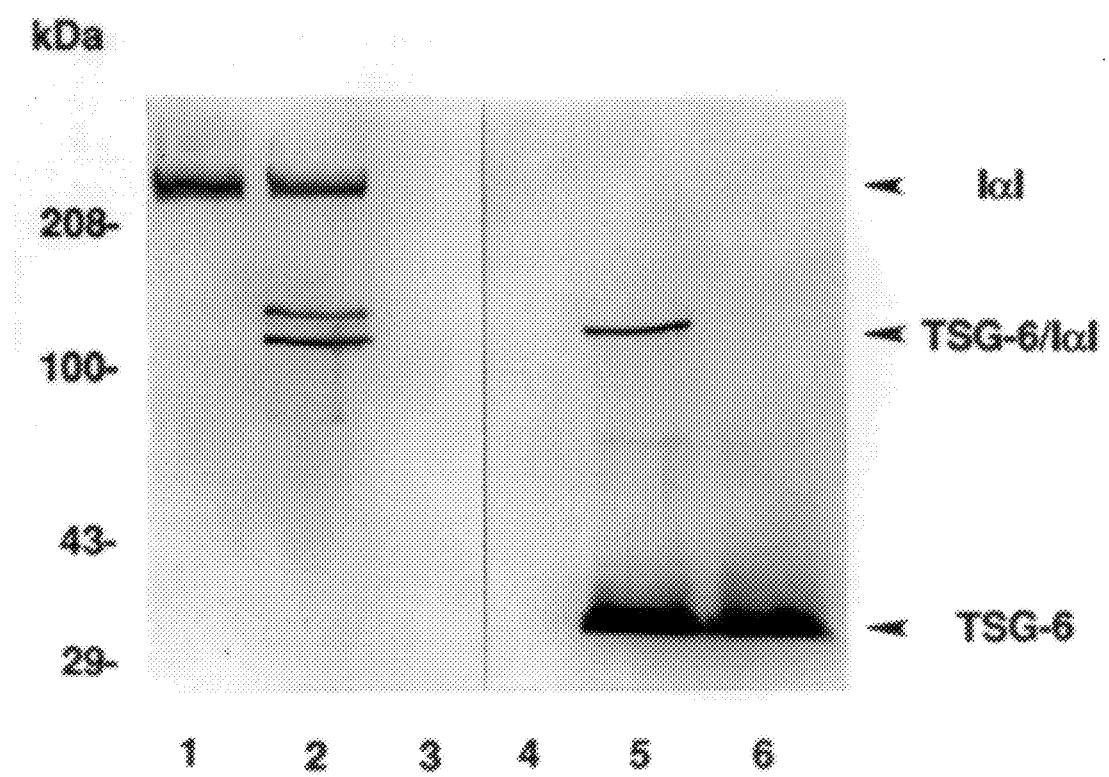

FIG. 22 shows binding of antibodies to IαI or TSG-6 protein recognize a 120-kDa complex formed after incubation of purified IαI and TSG-6 protein. Purified IαI was incubated in the absence (lanes 1, 4) or presence (lanes 2, 5) or purified TSG-6 protein at 37° C. for 10 min. Lanes 3 and 6 contain purified TSG-6 protein without IαI. All samples were separated by SDS-PAGE on 8% PAA under reducing conditions. For Western blot analysis, lanes 1–3 were developed with anti-IαI, and lanes 4–6 were developed with anti-TSG-6 antibody.

Figure 23:
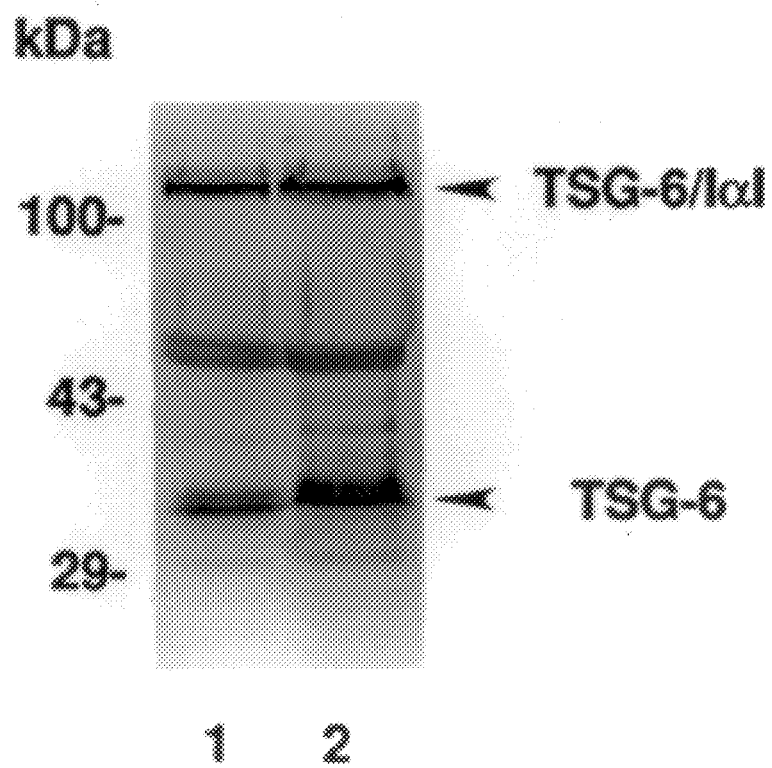

FIG. 23 shows treatment of the TSG-6/IαI complex with 8M urea. 100 μL of a TN-5B insect cell culture supernatant containing TSG-6 protein was incubated with 100 μL of a 1:50 dilution of human serum for 1 hr. at 37° C. Thereafter, one 100-μL aliquot was mixed with 2 mL of 8M urea and concentrated in a Centricon-10 unit to 100 μL (lane 2); the other aliquot was left untreated (lane 1). The reaction mixtures were then separated by SDS-PAGE and subjected to Western blot analysis with anti=TSG-6 antibody.

Figure 24:
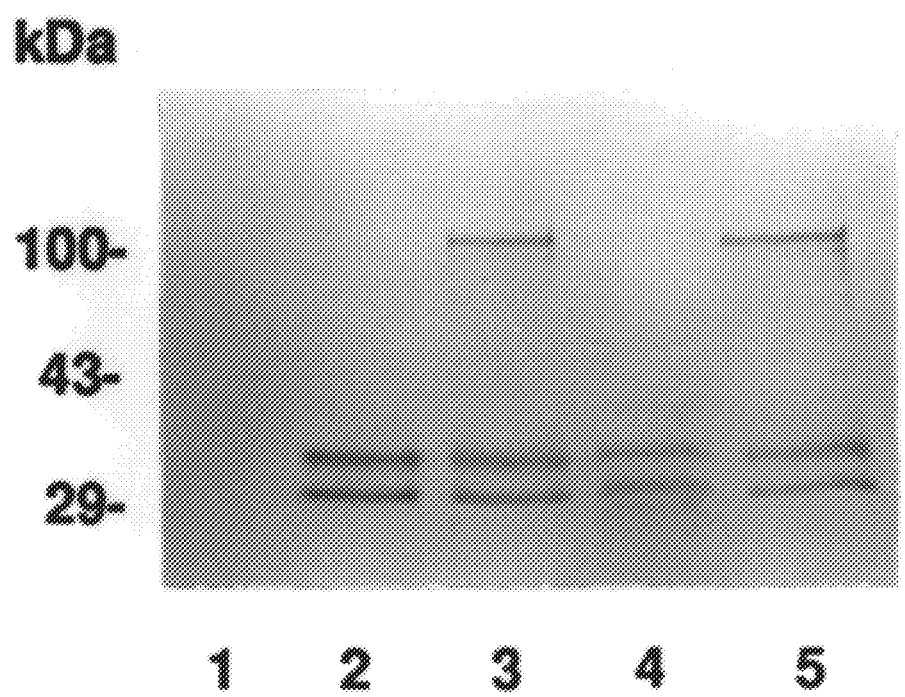

FIG. 24 shows treatment of the TSG-6/IαI complex with chondroitin sulfate ABC lyase or hyaluronidase. Partially purified IαI was incubated in the absence (lane 1) or presence of purified TSG-6 protein (lanes 3–5) at 37° C. for 1 hr. The sample ;containing both IαI and TSG-6 protein was divided into aliquots and further incubated without enzyme (lane 3), with 800 milliunits of chondroitin sulfate ABC lyase (lane 4), or with 1.6 units of hyaluronidase (lane 5). Lane 2 is a TSG-6 control without IαI. The reaction mixtures were separated by SDS-PAGE and analyzed by Western blotting with anti-TSG-6 antibody.

Figure 25:
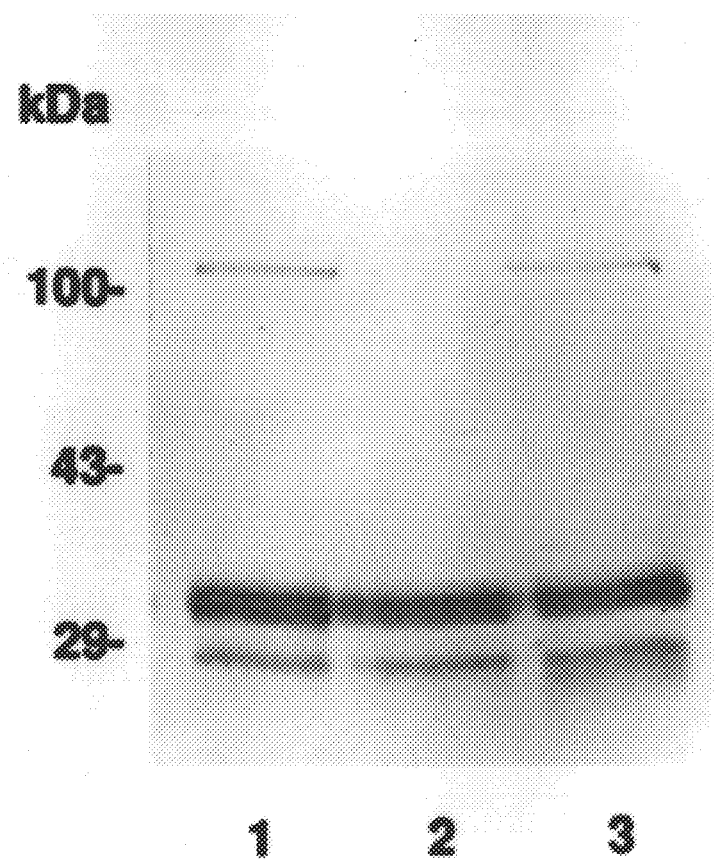

FIG. 25 shows TSG-6/IαI complex formation by IαI and TSG-6 proteins with chondroitin sulfate ABC lyase. Four micrograms of purified IαI and 3 μg of purified TSG-6 protein were incubated separately for 16 hrs. at 37° C. in the absence or presence of 30 millunits of chondroitin sulfate ABC lyase. Thereafter, control IαI was mixed with control TSG-6 protein (lane 1), shonroitinase-pretreated IαI was mixed with control TSG-6 (lane 2), and control IαI was reaction mixtured with chondroitinase-pretreated TSG-6 protein (lane 3). The reaction mixtures were incubated for 1 hr. at 37° C. before SDS-PAGE and Western blot analysis with anti-TSG-6 antibody.

DETAILED DESCRIPTION OF PREFERRED EMBODIMENTS

A number of genes activated in human FS-4 fibroblasts by tumor necrosis factor (TNF) were termed by the present inventors "TNF-stimulated genes" ((abbreviated TSG). It should be appreciated that such genes, and the proteins and glycoproteins they encode, are induced by cytokines more generally, including TNF, IL-1, and, in some case, interferons. The proteins, functional derivatives, such as peptide fragments, and antibodies to the proteins are useful in a number of methods of importance to the diagnosis and treatment of diseases and conditions in which the activity, or inactivity, of such cytokines is associated with the pathophysiology. Such diseases include chronic inflammation, such as rheumatoid arthritis, cancer, and infections, in particular with gram-negative bacteria.

Inflammatory conditions also detectable or treatable with a TSG-protein antibody, binding molecule or inhibiting molecule of the present invention can also include, but is not limited to, the following, which can include TNF related pathologies:

(A) acute and chronic immune and autoimmune pathologies, such as systemic lupus erythematosus (SLE) rheumatoid arthritis, thyroidosis, graft versus host disease, scleroderma, diabetes mellitus, Graves' disease, and the like;

(B) infections, including, but not limited to, sepsis syndrome, cachexia, circulatory collapse and shock resulting from acute or chronic bacterial infection, acute and chronic parasitic and/or infectious diseases, bacterial, viral or fungal, such as a HIV, AIDS (including symptoms of cachexia, autoimmune disorders, AIDS dementia complex and infections);

(C) inflammatory diseases, such as chronic inflammatory pathologies and vacsular inflammatory pathologies, including chronic inflammatory pathologies such as sarcoidosis, chronic inflammatory bowel disease, ulcerative colitis, and Crohn's pathology and vascular inflammatory pathologies, such as, but not limited to, disseminated intravascular coagulation, atherosclerosis, and Kawasaki's pathology:

(D) neurodegenerative diseases, including, but are not limited to, demyelinating diseases, such as multiple sclerosis and acute transverse myelitis;

extrapyramidal and cerebellar disorders' such as lesions of the corticospinal system;

disorders of the basal ganglia or cerebellar disorders;

hyperkinetic movement disorders such as Huntington's Chorea and senile chorea;

drug-induced movement disorders, such as those induced by drugs which block CNS dopamine receptors;

hypokinetic movement disorders, such as Parkinson's disease;

Progressive supranucleo palsy;

Cerebellar and Spinocerebellar Disorders, such as astructural lesions of the cerebellum; spinocerebellar degenerations (spinal ataxia, Friedreich's ataxia, cerebellar cortical degenerations, multiple systems degenerations (Mencel, Dejerine-Thomas, Shi-Drager, and Machado-Joseph); and systemic disorders (Refsum's disease, abetalipoprotemia, ataxia, telangiectasia, and mitochondrial multi.system disorder);

demyelinating core disorders, such as multiple sclerosis, acute transverse myelitis;

disorders of the motor unit, such as neurogenic muscular atrophies (anterior horn cell degeneration, such as amyotrophic lateral sclerosis, infantile spinal muscular atrophy and juvenile spinal muscular atrophy); Alzheimer's disease; Down's Syndrome in middle age; Diffuse Lewy body disease; Senile Dementia of Lewy body type; Wernicke-Korsakoff syndrome;

chronic alcoholism; Creutzfeldt-Jakob disease;

Subacute sclerosing panencephalitis, Hallerrorden Spatz disease; and Dementia pugilistica, or any subset thereof;

(E) malignant pathologies involving TNF-secreting tumors or other malignancies involving TNF, such as, but not limited to leukemias (acute, chronic myelocytic, chronic lymphocytic and/or myelodyspastic syndrome); lymphomas (Hodgkin's and non-Hodgkin's lymphomas, such as malignant lymphomas (Burkitt's lymphoma or Mycosis fungoides)); and (F) alcohol-induced hepatitis.

See, e.g., Berkow et al, eds., The Merck Manual, 16th edition, chapter 11, pp 1380–1529, Merck and Co., Rahway, N.J., 1992, which reference, and references cited therein, are entirely incorporated herein by reference.

The present invention is directed to one of these genes and its protein product, both termed TSG-6. The present invention provides TSG-6 DNA, mRNA and protein in substantially pure form, functional derivatives of the protein such as peptide fragments, antibodies specific for the protein, methods of producing the DNA, mRNA and protein, methods of using these molecules in diagnosis, therapy, and study of the abovementioned disease states.

By "substantially pure" is meant any protein or peptide of the present invention, or any DNA or mRNA sequence encoding any such protein or peptide, which is essentially free of other proteins, DNA sequences or mRNA sequences, respectively, or of other contaminants with which it might normally be found in nature, and, as such, exists in a form not found in nature.

"Substantially free of other proteins" indicates that the protein has been purified away from at least 90 per cent (on a weight basis), and from even at least 99 per cent, if desired, of other proteins and glycoproteins with which it is natively associated, and is therefore substantially free of them. That can be achieved by subjecting the cells, tissue or fluids expressing or containing the TSG-6 protein to protein purification techniques such as immunoabsorbent columns bearing antibodies, such as monoclonal antibodies (mAb) reactive against the protein. Because of the fact that TSG-6 binds to hyaluronic acid, the TSG-6 protein or glycoprotein may be purified using an affinity column to which hyaluronic acid is bound. Alternatively, the purification can be achieved by a combination of standard methods, such as ammonium sulfate precipitation, molecular sieve chromatography, and ion exchange chromatography.

The methods of the present invention are used to identify normal or mutant TSG-6 genes or measure the presence or amount of TSG-6 protein associated with a cell or tissue, or secreted by a cell; such methods can be used to identify susceptibility to, or presence of (a) inflammatory conditions, in particular proteoglycan breakdown such as that associated with rheumatoid arthritis, (b) sepsis following gram-negative bacterial infections, and (c) disorders associated with leukocyte adhesion.

An amino acid or nucleic acid sequence of a TSG-6 polypeptide of the present invention is said to "substantially correspond" to another amino acid or nucleic acid sequence, respectively, if the sequence of amino acids or nucleic acid in both molecules provides polypeptides having biological activity that is substantially similar, qualitatively or quantitatively, to the corresponding fragment of at least one hyaluron binding domain, an inter-α-inhibitor binding domain, a TNF binding domain, or which may be synergistic when two or more of these domains, consensus sequences or homologs thereof are present.

Additionally or alternatively, such "substantially corresponding" sequences of TSG-6 polypeptides include conservative amino acid or nucleotide substitutions, or degenerate nucleotide codon substitutions wherein individual amino acid or nucleotide substitutions are well known in the art.

Alternatively or additionally, substantially corresponding refers to TSG-6 polypeptides having amino acid sequences having at least 80% homology or identity to an amino acid sequence of SEQ ID NO:1 or 2, such as 80, 81, 82, 83, 84, 85, 86, 87, 88, 89, 90, 91, 92, 93, 94, 95, 96, 97, 98, 99 or 100% homology or identity, e.g., using known modeling algorithms, such as, but not limited to, ECEPP, INSIGHT, DISCOVER, CHEM-DRAW, AMBER, FRODO and CHEM-X. Such algorithms compare bniding domains between related TSG-6 polypeptides, and alternative consensus polypeptide fragments are thus determined.

Accordingly, TSG-6 polypeptides of the present invention, or nucleic acid encoding therefor, include a finite set of substantially corresponding sequences as substitution peptides or polynucleotides which can be routinely obtained by one of ordinary skill in the art, without undue experimentation, based on the teachings and guidance presented herein. For a detailed description of protein chemistry and structure, see Schulz, G. E. et al., *Principles of Protein Structure,* Springer-Verlag, New York, 1978, and Creighton, T. E., *Proteins: Structure and Molecular Properties,* W. H. Freeman & Co., San Francisco, 1983, which are hereby incorporated by reference. For a presentation of nucleotide sequence substitutions, such as codon preferences, see Ausubel et al, supra, at §§ A.1.1–A.1.24, and Sambrook et al, supra, at Appendices C and D.

Conservative substitutions of a TSG-6 polypeptide of the present invention includes a variant wherein at least one amino acid residue in the polypeptide has been conservatively replaced by a different amino acid. Such substitutions preferably are made in accordance with the following list as presented in Table IA which substitutions may be determined by routine experimentation to provide modified structural and functional properties of a synthesized polypeptide molecule, while maintaining the receptor binding, inhibiting or mimicking biological activity, as determined by TSG-6 binding receptor activity assays.

TABLE IA

| Original Residue | Exemplary Substitution |
| --- | --- |
| Ala | Gly;Ser |
| Arg | Lys |
| Asn | Gln;His |
| Asp | Glu |
| Cys | Ser |
| Gln | Asn |
| Glu | Asp |
| Gly | Ala;Pro |
| His | Asn;Gln |
| Ile | Leu;Val |
| Leu | Ile;Val |
| Lys | Arg;Gln;Glu |
| Met | Leu;Tyr;Ile |
| Phe | Met;Leu;Tyr |
| Ser | Thr |
| Thr | Ser |
| Trp | Tyr |
| Tyr | Trp;Phe |
| Val | Ile;Leu |

Alternatively, another group of substitutions of TSG-6 polypeptides of the present invention are those in which at least one amino acid residue in the protein molecule has been removed and a different residue inserted in its place according to the following Table IB. The types of substitutions which may be made in the protein or peptide molecule of the present invention may be based on analysis of the frequencies of amino acid changes between a homologous protein of different species, such as those presented in Table 1-2 of Schulz et al., supra and FIGS. 3–9 of Creighton, supra. Based on such an analysis, alternative conservative substitutions are defined herein as exchanges within one of the following five groups:

TABLE IB

1. Small aliphatic, nonpolar or slightly polar residues: Ala, Ser, Thr (Pro, Gly);
2. Polar, negatively charged residues and their amides: Asp, Asn, Glu, Gln;
3. Polar, positively charged residues: His, Arg, Lys;
4. Large aliphatic, nonpolar residues: Met, Leu, Ile, Val (Cys); and
5. Large aromatic residues: Phe, Tyr, Trp.

The three amino acid residues in parentheses above have special roles in protein architecture. Gly is the only residue lacking any side chain and thus imparts flexibility to the chain. This however tends to promote the formation of secondary structure other than α-helical. Pro, because of its unusual geometry, tightly constrains the chain. It generally tends to promote β-turn-like structures, although in some cases Cys can be capable of participating in disulfide bond formation which is important in protein folding. Note the Schulz et al. would merge Groups 1 and 2, above. Note also that Tyr, because of its hydrogen bonding potential, has significant kinship with Ser, and Thr, etc.

Conservative amino acid substitutions according to the present invention, e.g., as presented above, are known in the art and would be expected to maintain biological and structural properties of the polypeptide after amino acid substitution. Most deletions and insertions, and substitutions according to the present invention are those which do not produce radical changes in the characteristics of the protein or peptide molecule. "Characteristics" is defined in a non-inclusive manner to define both changes in secondary structure, e.g. α-helix or β-sheet, as well as changes in physiological activity, e.g. in receptor binding assays.

However, when the exact effect of the substitution, deletion, or insertion is to be confirmed one skilled in the art will appreciate that the effect of the substitution or substitutions will be evaluated by routine screening assays, either immunoassays or bioassays to confirm biological activity, such as receptor binding or modulation of ligand binding to the corresponding TSG-6 receptor. See, e.g., Maranges et al., eds., for example, a substituted polypeptide typically is made by site-specific mutagenesis of the peptide molecule-encoding nucleic acid, expression of the mutant nucleic acid in recombinant cell culture, and, optionally, purification from the cell culture, for example, by immunoaffinity chromatography using a specific antibody on a chemically derivatized column or immobilized membranes or hollow fibers (to absorb the mutant by binding to at least one epitope).

In one embodiment, the invention is directed to a naturally occurring TSG-6 protein or glycoprotein substantially free from impurities of human origin with which it is natively associated. In another embodiment, the invention is directed to a recombinant TSG-6 encoded protein or glycoprotein.

It will be understood that the TSG-6 protein of the present invention can be purified biochemically or physicochemically from a variety of cell or tissue sources. For preparation of naturally occurring TSG-6 protein, connective tissue cells such as human fibroblasts are preferred. Alternatively, methods are well known for the synthesis of polypeptides of desired sequence on solid phase supports and their subsequent separation from the support.

Because the TSG-6 gene can be isolated or synthesized, the TSG-6 polypeptide, or a functional derivative thereof, can be synthesized substantially free of other proteins or glycoproteins of mammalian origin in a prokaryotic organism or in a non-mammalian eukaryotic organism, if desired. As intended by the present invention, a TSG-6 protein or glycoprotein molecule produced by recombinant means in mammalian cells, such as transfected GM-637 cells, for example, is either a naturally occurring protein sequence or a functional derivative thereof. Where a naturally occurring protein or glycoprotein is produced by recombinant means, it is provided substantially free of the other proteins and glycoproteins with which it is natively associated.

A preferred use of this invention is the production by chemical synthesis or recombinant DNA technology of fragments of the TSG-6 molecule, which still retain biological activity such as binding to antibodies, binding to hyaluronic acid, and the like. Among the advantages of shorter peptides for some of the methods of the present invention are (1) greater stability and diffusibility, and (2) less immunogenicity. As discussed herein, the TSG-6 proteins or peptides of the present invention may be further modified for purposes of drug design, such as, for example, to reduce immunogenicity, to promote solubility or enhance delivery, or to prevent clearance or degradation.

Also included within the scope of the resent invention are soluble forms of the TSG-6 protein, and functional derivatives of the TSG-6 protein having similar bioactivity for all the uses described herein. Also intended are all active forms of TSG-6 derived from the TSG-6 transcript, and all muteins with TSG-6 activity.

By "functional derivative" is meant a "fragment," "variant," "analog," or "chemical derivative" of the TSG-6 protein. A functional derivative retains at least a portion of the function of the TSG-6 protein which permits its utility in accordance with the present invention.

A "fragment" of the TSG-6 protein is any subset of the molecule, that is, a shorter peptide.

A "variant" of the TSG-6 refers to a molecule substantially similar to either the entire peptide or a fragment thereof. Variant peptides may be conveniently prepared by direct chemical synthesis of the variant peptide, using methods well-known in the art.

Alternatively, amino acid sequence variants of the peptide can be prepared by mutations in the DNA which encodes the synthesized peptide. Such variants include, for example, deletions from, or insertions or substitutions of, residues within the amino acid sequence. Any combination of deletion, insertion, and substitution may also be made to arrive at the final construct, provided that the final construct possesses the desired activity. Obviously, the mutations that will be made in the DNA encoding the variant peptide must not alter the reading frame and preferably will not create complementary regions that could produce secondary mRNA structure (see European Patent Publication No. EP 75,444).

At the genetic level, these variants ordinarily are prepared by site-directed mutagenesis (as exemplified by Adelman et al., DNA 2:183 (1983)) of nucleotides in the DNA encoding the peptide molecule, thereby producing DNA encoding the variant, and thereafter expressing the DNA in recombinant cell culture. The variants typically exhibit the same qualitative biological activity as the nonvariant peptide.

In general, site-directed mutagenesis in accordance herewith is performed by first obtaining a single-stranded vector that includes within its sequence a DNA sequence that encodes the relevant peptide. An oligonucleotide primer bearing the desired mutated sequence is prepared, generally synthetically, for example, by the method of Crea et al., Proc. Natl. Acad. Sci. (USA) 75:5765 (1978). This primer is then annealed with the single-stranded protein-sequence-containing vector, and subjected to DNA polymerizing enzymes such as E. coli polymerase I Klenow fragment, to complete the synthesis of the mutation-bearing strand. Thus, a mutated sequence in the second strand bears the desired mutation. This heteroduplex vector is then used to transform appropriate cells and clones are selected that include recombinant vectors bearing the mutated sequence arrangement. The mutated protein region may be removed and placed in an appropriate vector for protein production, generally an expression vector of the type that may be employed for transformation of an appropriate host.

Alternatively, the DNA encoding a normal or variant TSG-6 protein can be altered by homologous recombination, a technique developed within the past few years for targeting genes to induce or correct mutations in transcriptionally active genes (Kucherlapati, *Prog. in Nucl. Acid Res. and Mol. Biol.* 36:301 (1989)). The technique of homologous recombination was developed as a method for introduction of specific mutations into specific regions of the mammalian genome (Thomas et al., *Cell,* 44:419–428, 1986; Thomas and Capecchi, *Cell* 51:503–512 (1987); Doetschman et al., *Proc. Natl. Acad. Sci.* USA 85:8583–8587 (1988)) or to correct specific mutations within defective genes (Doetschman et al., *Nature* 330:576–578 (1987)). The above references to homologous recombination are hereby incorporated by reference.

An example of a terminal insertion includes a fusion of a signal sequence, whether heterologous or homologous to the host cell, to the N-terminus of the peptide molecule to facilitate the secretion of mature peptide molecule from recombinant hosts.

Another group of variants are those in which at least one amino acid residue in the peptide molecule, and preferably, only one, has been removed and a different residue inserted in its place. Such substitutions preferably are made in accordance with the following list when it is desired to modulate finely the characteristics of a peptide molecule.

| Original Residue | Exemplary Substitutions | Original Residue | Exemplary Substitutions |
| --- | --- | --- | --- |
| Ala | gly; ser | Leu | ile; val |
| Arg | lys | Lys | arg; gln; glu |
| Asn | gln; his | Met | leu; tyr; ile |
| Asp | glu | Phe | met; leu; tyr |
| Cys | ser | Ser | thr |
| Gln | asn | Thr | ser |
| Glu | asp | Trp | tyr |
| Gly | ala; pro | Tyr | trp; phe |
| His | asn; gln | Val | ile; leu |
| Ile | leu; val | | |

Substantial changes in functional or immunological properties are made by selecting substitutions that are less conservative than those in the above list, that is, by selecting residues that differ more significantly in their effect on maintaining (a) the structure of the peptide backbone in the area of the substitution, for example, as a sheet or helical conformation, (b) the charge or hydrophobicity of the molecule at the target site, or (c) the bulk of the side chain. The substitutions that in general are expected to produce substantial changes are those in which (a) glycine and/or proline is substituted by another amino acid or is deleted or inserted; (b) a hydrophilic residue, e.g., seryl or threonyl, is substituted for (or by) a hydrophobic residue, e.g., leucyl, isoleucyl, phenylalanyl, valyl, or alanyl; (c) a cysteine residue is substituted for (or by) any other residue; (d) a residue having an electropositive side chain, e.g., lysyl, arginyl, or histidyl, is substituted for (or by) a residue having an electronegative charge, e.g., glutamyl or aspartyl; or (e) a residue having a bulky side chain, e.g., phenylalanine, is substituted for (or by) one not having such a side chain, e.g., glycine.

Most deletions and insertions, and substitutions in particular, are not expected to produce radical changes in the characteristics of the peptide molecule. However, when it is difficult to predict the exact effect of the substitution, deletion, or insertion in advance of doing so, one skilled in the art will appreciate that the effect will be evaluated by routine screening assays. For example, a TSG-6 variant typically is made by site-specific mutagenesis or homologous recombination of the TSG-6-encoding nucleic acid, expression of the variant nucleic acid in recombinant cell culture, and, optionally, purification from the cell culture, for example, by immunoaffinity adsorption on an antibody containing column.

An "analog" of the TSG-6 protein refers to a non-natural molecule substantially similar to either the entire molecule or a fragment thereof.

A "chemical derivative" of the TSG-6 protein contains additional chemical moieties not normally a part of the protein. Covalent modifications of the peptide are included within the scope of this invention. Such modifications may be introduced into the molecule by reacting targeted amino acid residues of the peptide with an organic derivatizing agent that is capable of reacting with selected side chains or terminal residues.

Cysteinyl residues most commonly are reacted with alpha-haloacetates (and corresponding amines), such as 2-chloroacetic acid or chloroacetamide, to give carboxymethyl or carboxyamidomethyl derivatives. Cysteinyl residues also are derivatized by reaction with bromotrifluoroacetone, alpha-bromo-beta-(5-imidozoyl) propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylprocarbonate at pH 5.5–7.0 because this agent is relatively specific for the histidyl side chain. Para-bromophenacyl bromide also is useful; the reaction is preferably performed in 0.1M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing alpha-amino-containing residues include imidoesters such as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $PK_s$ of the guanidine functional group. Furthermore, these reagents may react with the groups of lysine as well as the arginine epsilon-amino group.

The specific modification of tyrosyl residues per se has been studied extensively, with particular interest in introducing spectral labels into tyrosyl residues by reaction with aromatic diazonium compounds or tetranitromethane. Most commonly, N-acetylimidizol and tetranitromethane are used to form O-acetyl tyrosyl species and 3-nitro derivatives, respectively.

Carboxyl side groups (aspartyl or glutamyl) are selectively modified by reaction with carbodiimides (R'—N—C—N—R') such as 1-cyclohexyl-3-(2-morpholinyl-(4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Glutaminyl and asparaginyl residues are frequently deamidated to the corresponding glutamyl and aspartyl residues. Alternatively, these residues are deamidated under mildly acidic conditions. Either form of these residues falls within the scope of this invention.

Derivatization with bifunctional agents is useful for crosslinking the peptide to a water-insoluble support matrix or to other macromolecular carriers. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-[(p-azidophenyl) dithio]propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Other modifications include hydroxylation of proline and lysine, phosphorylation of hydroxyl groups of seryl or threonyl residues, methylation of the alpha-amino groups of lysine, arginine, and histidine side chains (T. E. Creighton, *Proteins: Structure and Molecule Properties*, W. H. Freeman & Co., San Francisco, pp. 79–86 (1983)), acetylation of the N-terminal amine, and, in some instances, amidation of the C-terminal carboxyl groups.

Such derivatized moieties may improve the solubility, absorption, biological half life, and the like. The moieties may alternatively eliminate or attenuate any undesirable side effect of the protein and the like. Moieties capable of mediating such effects are disclosed, for example, in *Remington's Pharmaceutical Sciences*, 16th ed., Mack Publishing Co., Easton, Pa. (1980).

Standard reference works setting forth the general principles of recombinant DNA technology include Watson, J. D. et al., *Molecular Biology of the Gene*, Volumes I and II, The Benjamin/Cummings Publishing Company, Inc., publisher, Menlo Park, Calif. (1987); Darnell, J. E. et al., *Molecular Cell Biology*, Scientific American Books, Inc., publisher, New York, N.Y. (1986); Lewin, B. M., *Genes II*, John Wiley & Sons, publishers, New York, N.Y. (1985); Old, R. W., et al., *Principles of Gene Manipulation: An Introduction to Genetic Engineering*, 2d edition, University of California Press, publisher, Berkeley, Calif. (1981); and Sambrook, J. et al., *Molecular Cloning: A Laboratory Manual*, Cold Spring Harbor Laboratory, Cold Spring Harbor, N.Y. (1989). These references are hereby incorporated by reference.

By "cloning" is meant the use of in vitro recombination techniques to insert a particular gene or other DNA sequence into a vector molecule. In order to successfully clone a desired gene, it is necessary to employ methods for generating DNA fragments, for joining the fragments to vector molecules, for introducing the composite DNA molecule into a host cell in which it can replicate, and for selecting the clone having the target gene from amongst the recipient host cells.

By "cDNA" is meant complementary or copy DNA produced from an RNA template by the action of RNA-dependent DNA polymerase (reverse transcriptase). Thus a "cDNA clone" means a duplex DNA sequence complementary to an RNA molecule of interest, carried in a cloning vector.

By "cDNA library" is meant a collection of recombinant DNA molecules containing cDNA inserts which together comprise the entire expressible genome of an organism. Such a cDNA library may be prepared by methods known to those of skill, and described, for example, in Sambrook et al., supra. Generally, RNA is first isolated from the cells of an organism from whose genome it is desired to clone a particular gene. Preferred for the purposes of the present invention are mammalian, most preferably, human, cell lines.

Oligonucleotides representing a portion of the TSG-6 sequence are useful for screening for the presence of homologous genes and for the cloning of such genes. Techniques for synthesizing such oligonucleotides are disclosed by, for example, Wu, R., et al., *Prog. Nucl. Acid. Res. Molec. Biol.* 21:101–141 (1978).

Because the genetic code is degenerate, more than one codon may be used to encode a particular amino acid (Watson, J. D., In: *Molecular Biology of the Gene*, 4th Ed., Benjamin/Cummings Publishing Co., Inc., Menlo Park, Calif. (1987)). Using the genetic code, one or more different oligonucleotides can be identified, each of which would be capable of encoding the amino acid. The probability that a particular oligonucleotide will, in fact, constitute the actual XXX-encoding sequence can be estimated by considering abnormal base pairing relationships and the frequency with which a particular codon is actually used (to encode a particular amino acid) in eukaryotic cells. Such "codon usage rules" are disclosed by Lathe, R., et al., *J. Molec. Biol.* 183:1–12 (1985). Using the "codon usage rules" of Lathe, a single oligonucleotide, or a set of oligonucleotides, that contains a theoretical "most probable" nucleotide sequence capable of encoding the TSG-6 sequences is identified.

Although occasionally an amino acid sequence may be encoded by only a single oligonucleotide, frequently the amino acid sequence may be encoded by any of a set of similar oligonucleotides. Importantly, whereas all of the members of this set contain oligonucleotides which are capable of encoding the TSG-6 peptide fragment and, thus, potentially contain the same oligonucleotide sequence as the gene which encodes the peptide fragment, only one member of the set contains the nucleotide sequence that is identical to the nucleotide sequence of the gene. Because this member is present within the set, and is capable of hybridizing to DNA even in the presence of the other members of the set, it is possible to employ the unfractionated set of oligonucleotides in the same manner in which one would employ a single oligonucleotide to clone the gene that encodes the protein.

The oligonucleotide, or set of oligonucleotides, containing the theoretical "most probable" sequence capable of encoding the TSG-6 fragment is used to identify the sequence of a complementary oligonucleotide or set of oligonucleotides which is capable of hybridizing to the "most probable" sequence, or set of sequences. An oligonucleotide containing such a complementary sequence can be employed as a probe to identify and isolate the TSG-6 gene (Sambrook et al., supra).

A suitable oligonucleotide, or set of oligonucleotides, which is capable of encoding a fragment of the TSG-6 gene (or which is complementary to such an oligonucleotide, or set of oligonucleotides) is identified (using the above-described procedure), synthesized, and hybridized by means well known in the art, against a DNA or, more preferably, a cDNA preparation derived from cells which are capable of expressing the TSG-6 gene, such as TNF-treated FS-4 cells.

Single stranded oligonucleotide molecules complementary to the "most probable" TSG-6 protein coding sequences can be synthesized using procedures which are well known to those of ordinary skill in the art (Belagaje, R., et al., *J.*

*Biol. Chem.* 254:5765–5780 (1979); Maniatis, T., et al., In: *Molecular Mechanisms in the Control of Gene Expression,* Nierlich, D. P., et al., Eds., Acad. Press, NY (1976); Wu, R., et al., *Prog. Nucl. Acid Res. Molec. Biol.* 21:101–141 (1978); Khorana, R. G., *Science* 203:614–625 (1979)). Additionally, DNA synthesis may be achieved through the use of automated synthesizers. Techniques of nucleic acid hybridization are disclosed by Sambrook et al. (supra), and by Haymes, B. D., et al. (In: *Nucleic Acid Hybridization A Practical Approach,* IRL Press, Washington, DC (1985)), which references are herein incorporated by reference. Techniques such as, or similar to, those described above have successfully enabled the cloning of genes for human aldehyde dehydrogenases (Hsu, L. C., et al., *Proc. Natl. Acad. Sci. USA* 82:3771–3775 (1985)), fibronectin (Suzuki, S., et al., *Eur. Mol. Biol. Organ. J.* 4:2519–2524 (1985)), the human estrogen receptor gene (Walter, P., et al., *Proc. Natl. Acad. Sci. USA* 82:7889–7893 (1985)), tissue-type plasminogen activator (Pennica, D., et al., *Nature* 301:214–221 (1983)) and human term placental alkaline phosphatase complementary DNA (Kam, W., et al., *Proc. Natl. Acad. Sci. USA* 82:8715–8719 (1985)).

In an alternative way of cloning the TSG-6 gene, a library of expression vectors is prepared by cloning DNA or, more preferably, cDNA (from a cell capable of expressing TSG-6, such as a TNF-treated FS-4 cell) into an expression vector. The library is then screened for members capable of expressing a protein which binds to anti-TSG-6 antibody, and which has a nucleotide sequence that is capable of encoding polypeptides that have the same amino acid sequence as TSG-6 proteins or peptides, or fragments thereof. In this embodiment, DNA, or more preferably cDNA, is extracted and purified from a cell which is capable of expressing TSG-6 protein. The purified cDNA is fragmentized (by shearing, endonuclease digestion, etc.) to produce a pool of DNA or cDNA fragments. DNA or cDNA fragments from this pool are then cloned into an expression vector in order to produce a genomic library of expression vectors whose members each contain a unique cloned DNA or cDNA fragment.

By "vector" is meant a DNA molecule, derived from a plasmid or bacteriophage, into which fragments of DNA may be inserted or cloned. A vector will contain one or more unique restriction sites, and may be capable of autonomous replication in a defined host or vehicle organism such that the cloned sequence is reproducible.

An "expression vector" is a vector which (due to the presence of appropriate transcriptional and/or translational control seqeences) is capable of expressing a DNA (or cDNA) molecule which has been cloned into the vector and of thereby producing a polypeptide or protein. Expression of the cloned sequences occurs when the expression vector is introduced into an appropriate host cell. If a prokaryotic expression vector is employed, then the appropriate host cell would be any prokaryotic cell capable of expressing the cloned sequences. Similarly, if a eukaryotic expression vector is employed, then the appropriate host cell would be any eukaryotic cell capable of expressing the cloned sequences. Importantly, since eukaryotic DNA may contain intervening sequences, and since such sequences cannot be correctly processed in prokaryotic cells, it is preferable to employ cDNA from a cell which is capable of expressing TSG-6 in order to produce a prokaryotic genomic expression vector library. Procedures for preparing cDNA and for producing a genomic library are disclosed by Sambrook et al. (supra).

By "functional derivative" of a polynucleotide (DNA or RNA) molecule is meant a polynucleotide molecule encoding a "fragment" or "variant" of the TSG-6 protein. It can be a chemical derivative which retains its functions such as the ability to hybridize with a complementary polynucleotide molecule. Such a polynucleotide, or oligonucleotide, chemical derivative is useful as a molecular probe to detect TSG-6 sequences through nucleic acid hybridization assays.

A DNA sequence encoding the TSG-6 protein of the present invention, or its functional derivatives, may be recombined with vector DNA in accordance with conventional techniques, including blunt-ended or staggered-ended termini for ligation, restriction enzyme digestion to provide appropriate termini, filling in of cohesive ends as appropriate, alkaline phosphatase treatment to avoid undesirable joining, and ligation with appropriate ligases. Techniques for such manipulations are disclosed by Sambrook, J. et al., supra, and are well known in the art.

A nucleic acid molecule, such as DNA, is said to be "capable of expressing" a polypeptide if it contains nucleotide sequences which contain transcriptional and translational regulatory information and such sequences are "operably linked" to nucleotide sequences which encode the polypeptide. An operable linkage is a linkage in which the regulatory DNA sequences and the DNA sequence sought to be expressed are connected in such a way as to permit gene expression. The precise nature of the regulatory regions needed for gene expression may vary from organism to organism, but shall in general include a promoter region which, in prokaryotes, contains both the promoter (which directs the initiation of RNA transcription) as well as the DNA sequences which, when transcribed into RNA, will signal the initiation of protein synthesis. Such regions will normally include those 5'-non-coding sequences involved with initiation of transcription and translation, such as the TATA box, capping sequence, CAAT sequence, and the like.

If desired, the non-coding region 3' to the gene sequence coding for the protein may be obtained by the above-described methods. This region may be retained for its transcriptional termination regulatory sequences, such as termination and polyadenylation. Thus, by retaining the 3'-region naturally contiguous to the DNA sequence coding for the protein, the transcriptional termination signals may be provided. Where the transcriptional termination signals are not satisfactorily functional in the expression host cell, then a 3' region functional in the host cell may be substituted.

Two sequences of a nucleic acid molecule are said to be "operably linked" when they are linked to each other in a manner which either permits both sequences to be transcribed onto the same RNA transcript, or permits an RNA transcript, begun in one sequence to be extended into the second sequence. Thus, two sequences, such as a promoter sequence and any other "second" sequence of DNA or RNA are operably linked if transcription commencing in the promoter sequence will produce an RNA transcript of the operably linked second sequence. In order to be "operably linked" it is not necessary that two sequences be immediately adjacent to one another.

A promoter is a double-stranded DNA or RNA molecule which is capable of binding RNA polymerase and promoting the transcription of an "operably linked" nucleic acid sequence. As used herein, a "promoter sequence" is the sequence of the promoter which is found on that strand of the DNA or RNA which is transcribed by the RNA polymerase. A "promoter sequence complement" is a nucleic acid molecule whose sequence is the complement of a "promoter sequence." Hence, upon extension of a primer DNA or RNA adjacent to a single-stranded "promoter sequence complement" or, of a "promoter sequence," a double-stranded molecule is created which will contain a functional promoter, if that extension proceeds towards the "promoter sequence" or the "promoter sequence complement." This functional promoter will direct the transcription of a nucleic acid molecule which is operably linked to that strand of the double-stranded molecule which contains the "promoter sequence" (and not that strand of the molecule which contains the "promoter sequence complement").

Certain RNA polymerases exhibit a high specificity for such promoters. The RNA polymerases of the bacteriophages T7, T3, and SP-6 are especially well characterized, and exhibit high promoter specificity. The promoter sequences which are specific for each of these RNA polymerases also direct the polymerase to utilize (i.e. transcribe) only one strand of the two strands of a duplex DNA template. The selection of which strand is transcribed is determined by the orientation of the promoter sequence. This selection determines the direction of transcription since RNA is only polymerized enzymatically by the addition of a nucleotide 5' phosphate to a 3' hydroxyl terminus. The promoter sequences of the present invention may be either prokaryotic, eukaryotic or viral. Suitable promoters are repressible, or, more preferably, constitutive. Strong promoters are preferred.

The present invention encompasses the expression of the TSG-6 protein (or a functional derivative thereof) in either prokaryotic or eukaryotic cells, although eukaryotic expression is preferred.

Preferred prokaryotic hosts include bacteria such as *E. coli,* Bacillus, Streptomyces, Pseudomonas, Salmonella, Serratia, etc. The most preferred prokaryotic host is *E. coli.* Other enterobacteria such as *Salmonella typhimurium* or *Serratia marcescens,* and various Pseudomonas species may also be utilized. Under such conditions, the protein may not be glycosylated. The procaryotic host must be compatible with the replicon and control sequences in the expression plasmid.

The TSG-6 protein can be expressed in a prokaryotic cell (such as, for example, *E. coli, B. subtilis,* Pseudomonas, Streptomyces, etc.), either by itself, or as part of a fusion protein. For expression as a fusion protein, it must be linked in the appropriate reading frame with a prokaryotic protein. Preferred fusion protein "partners" are the trpE protein of *E. coli* or a bacteriophage protein, such as that of the MS2 phage (see Examples, below). To express the TSG-6 protein (or a functional derivative thereof) in a prokaryotic host, it is necessary to operably link the TSG-6 encoding sequence to a functional prokaryotic promoter. Examples of constitutive promoters include the int promoter of bacteriophage lambda, the bla promoter of the β-lactamase gene of pBR322, and the CAT promoter of the chloramphenicol acetyl transferase gene of pBR325, etc. Examples of inducible prokaryotic promoters include the major right and left promoters of bacteriophage lambda ($P_L$ and $P_R$), the trp, recA, lacZ, lacI, and gal promoters of *E. coli,* the α-amylase (Ulmanen, I., et al., *J. Bacteriol.* 162:176–182 (1985)) and the s-28-specific promoters of *B. subtilis* (Gilman, M. Z., et al., *Gene* 32:11–20 (1984)), the promoters of the bacteriophages of Bacillus (Gryczan, T. J., In: *The Molecular Biology of the Bacilli,* Academic Press, Inc., NY (1982)), and Streptomyces promoters (Ward, J. M., et al., *Mol. Gen. Genet.* 203:468–478 (1986)). Prokaryotic promoters are reviewed by Glick, B. R., (*J. Ind. Microbiol.* 1:277–282 (1987)); Cenatiempo, Y. (*Biochimie* 68:505–516 (1986)); and Gottesman, S. (*Ann. Rev. Genet.* 18:415–442 (1984)). For the present invention, a most preferred promoter is the PL promoter of lambda; alternatively, the protein can be expressed under control of a temperature-sensitive repressor of the lambda PL promoter (see Examples, below).

Proper expression in a prokaryotic cell also requires the presence of a ribosome binding site upstream of the gene-encoding sequence. Such ribosome binding sites are disclosed, for example, by Gold, L., et al. (*Ann. Rev. Microbiol.* 35:365–404 (1981)).

Preferred hosts are eukaryotic hosts including yeast, insects, fungi, and mammalian cells either in vivo, or in tissue culture. Mammalian cells provide post-translational modifications to protein molecules including correct folding or glycosylation at correct sites. Mammalian cells which may be useful as hosts include cells of fibroblast origin such as VERO or CHO, or cells of lymphoid origin, such as the hybridoma SP2/O-Ag14 or the murine myeloma P3-X63Ag8, and their derivatives. A most preferred host is one that does not express the TSG-6 gene upon treatment with TNF, such as GM-637, a SV40-transformed human fibroblast cell line.

For a mammalian cell host, many possible vector systems are available for the expression of TSG-6. A wide variety of transcriptional and translational regulatory sequences may be employed, depending upon the nature of the host. The transcriptional and translational regulatory signals may be derived from viral sources, such as adenovirus, bovine papilloma virus, Simian virus 40, or the like, where the regulatory signals are associated with a particular gene which has a high level of expression. Alternatively, promoters from mammalian expression products, such as actin, collagen, myosin, etc., may be employed. Transcriptional initiation regulatory signals may be selected which allow for repression or activation, so that expression of the genes can be modulated. Of interest are regulatory signals which are temperature-sensitive so that by varying the temperature, expression can be repressed or initiated, or are subject to chemical regulation, e.g., metabolite.

A yeast cell host provides substantial advantages in that it can also carry out post-translational peptide modifications including glycosylation. A number of recombinant DNA strategies exist which utilize strong promoter sequences and high copy number of plasmids which can be utilized for production of the desired proteins in yeast. Yeast recognizes leader sequences on cloned mammalian gene products and secretes peptides bearing leader sequences (i.e., pre-peptides).

Any of a series of yeast gene expression systems incorporating promoter and termination elements from the actively expressed genes coding for glycolytic enzymes produced in large quantities when yeast are grown in mediums rich in glucose can be utilized. Known glycolytic genes can also provide very efficient transcriptional control signals. For example, the promoter and terminator signals of the phosphoglycerate kinase gene can be utilized.

Production of TSG-6 or functional derivatives thereof in insects can be achieved, for example, by infecting the insect host with a baculovirus engineered to express TSG-6 by methods known to those of skill. Thus, in one embodiment, sequences encoding TSG-6 may be operably linked to the regulatory regions of the viral polyhedrin protein (Jasny, *Science* 238: 1653 (1987)). Infected with the recombinant baculovirus, cultured insect cells, or the live insects themselves, can produce the TSG-6 protein in amounts as great as 20 to 50% of total protein production. When live insects are to be used, caterpillars are presently preferred hosts for large scale TSG-6 production according to the invention.

As discussed above, expression of the TSG-6 protein in eukaryotic hosts requires the use of eukaryotic regulatory regions. Such regions will, in general, include a promoter region sufficient to direct the initiation of RNA synthesis. Preferred eukaryotic promoters include the SV40 early promoter (Benoist, C., et al., *Nature* (London) 290:304–310 (1981)); the RSV promoter associated with an MMTV LTR region; promoter of the mouse metallothionein I gene (Hamer, D., et al., *J. Mol. Appl. Gen.* 1:273–288 (1982)); the TK promoter of Herpes virus (McKnight, S., *Cell* 31:355–365 (1982)); the yeast gal4 gene promoter (Johnston, S. A., et al., *Proc. Natl. Acad. Sci.* (USA) 79:6971–6975 (1982); Silver, P. A., et al., *Proc. Natl. Acad. Sci.* (USA) 81:5951–5955 (1984)).

As is widely known, translation of eukaryotic mRNA is initiated at the codon which encodes the first methionine. For this reason, it is preferable to ensure that the linkage between a eukaryotic promoter and a DNA sequence which encodes the TSG-6 protein (or a functional derivative thereof) does not contain any intervening codons which are capable of encoding a methionine (i.e., AUG). The presence of such codons results either in a formation of a fusion protein (if the AUG codon is in the same reading frame as TSG-6 encoding DNA sequence) or a frame-shift mutation (if the AUG codon is not in the same reading frame as the TSG-6 encoding sequence).

The TSG-6 encoding sequence and an operably linked promoter may be introduced into a recipient prokaryotic or eukaryotic cell either as a non-replicating DNA (or RNA) molecule, which may either be a linear molecule or, more preferably, a closed covalent circular molecule. Since such molecules are incapable of autonomous replication, the expression of the TSG-6 protein may occur through the transient expression of the introduced sequence. Alternatively, permanent expression may occur through the integration of the introduced sequence into the host chromosome.

In one embodiment, a vector is employed which is capable of integrating the desired gene sequences into the host cell chromosome. Cells which have stably integrated the introduced DNA into their chromosomes can be selected by also introducing one or more markers which allow for selection of host cells which contain the expression vector. The marker may provide for prototropy to an auxotrophic host, biocide resistance, e.g., antibiotics, or heavy metals, such as copper or the like. The selectable marker gene can either be directly linked to the DNA gene sequences to be expressed, or introduced into the same cell by co-transfection. Additional elements may also be needed for optimal synthesis of single chain binding protein mRNA. These elements may include splice signals, as well as transcription promoters, enhancers, and termination signals. cDNA expression vectors incorporating such elements include those described by Okayama, H., *Mol. Cell. Biol.* 3:28 (1983).

In a preferred embodiment, the introduced sequence will be incorporated into a plasmid or viral vector capable of autonomous replication in the recipient host. Any of a wide variety of vectors may be employed for this purpose. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species. Preferred prokaryotic vectors include plasmids such as those capable of replication in *E. coli* (such as, for example, pBR322, ColE1, pSC101, pACYC 184, πVX. Such plasmids are, for example, disclosed by Sambrook et al. (supra). Bacillus plasmids include pC194, pC221, pT127, etc. Such plasmids are disclosed by Gryczan, T. (In: *The Molecular Biology of the Bacilli,* Academic Press, NY (1982), pp. 307–329). Suitable Streptomyces plasmids include pIJ101 (Kendall, K. J., et al., *J. Bacteriol.* 169:4177–4183 (1987)), and streptomyces bacteriophages such as φC31 (Chater, K. F., et al., In: *Sixth International Symposium on Actinomycetales Biology,* Akademiai Kaido, Budapest, Hungary (1986), pp. 45–54). Pseudomonas plasmids are reviewed by John, J. F., et al. (*Rev. Infect. Dis.* 8:693–704 (1986)), and Izaki, K. (*Jpn. J. Bacteriol.* 33:729–742 (1978)).

Preferred eukaryotic plasmids include BPV, vaccinia, SV40, 2-micron circle, etc., or their derivatives. Such plasmids are well known in the art (Botstein, D., et al., *Miami Wntr. Symp.* 19:265–274 (1982); Broach, J. R., In: *The Molecular Bioloqy of the Yeast Saccharomyces: Life Cycle and Inheritance,* Cold Spring Harbor Laboratory, Cold Spring Harbor, N.Y., p. 445–470 (1981); Broach, J. R., *Cell* 28:203–204 (1982); Bollon, D. P., et al., *J. Clin. Hematol. Oncol.* 10:39–48 (1980); Maniatis, T., In: *Cell Biology: A Comprehensive Treatise. Vol. 3. Gene Expression,* Academic Press, NY, pp. 563–608 (1980)).

Once the vector or DNA sequence containing the construct(s) has been prepared for expression, the vector or DNA construct(s) may be introduced into an appropriate host cell by any of a variety of suitable means, including such biochemical means as transformation, transfection, conjugation, protoplast fusion, calcium phosphate-precipitation, and application with polycations such as diethylaminoethyl (DEAE) dextran, and such mechanical means as electroporation, direct microinjection, and microprojectile bombardment (Johnston et al., *Science* 240:1538 (1988)), etc.

After the introduction of the vector, recipient cells are grown in a selective medium, which selects for the growth of vector-containing cells. Expression of the cloned gene sequence(s) results in the production of the TSG-6 protein, or in the production of a fragment of this protein. This can take place in the transformed cells as such, or following the induction of these cells to differentiate.

The expressed protein or fusion protein may be isolated and purified in accordance with conventional conditions, such as extraction, precipitation, chromatography, affinity chromatography, electrophoresis, or the like. For example, the cells may be collected by centrifugation, or with suitable buffers, lysed, and the protein isolated by column chromatography, for example, on DEAE-cellulose, phosphocellulose, polyribocytidylic acid-agarose, hydroxyapatite or by electrophoresis or immunoprecipitation. Alternatively, the TSG-6 or functional derivative thereof may be isolated by the use of anti- TSG-6 antibodies. Such antibodies may be obtained by weld-known methods, some of which are mentioned below.

Genetic constructs encoding TSG-6 functional derivatives thereof such as those described above, can be used in gene therapy. An abnormal TSG-6 molecule which results in enhanced susceptibility to disease, may be replaced by infusion of cells of the desired lineage (such as fibroblasts, for example) transfected with DNA encoding normal or modified TSG-6 protein, under conditions where the infused cells will preferentially replace the endogenous cell population.

The present invention is also directed to a transgenic non-human eukaryotic animal (preferably a rodent, such as a mouse) the germ cells and somatic cells of which contain genomic DNA according to the present invention which encodes the TSG-6 protein or a functional derivative thereof. The TSG-6 DNA is introduced into the animal to be made transgenic, or an ancestor of the animal, at an embryonic stage, preferably the one-cell, or fertilized oocyte, stage, and generally not later than about the 8-cell stage. The term "transgene," as used herein, means a gene which is incorporated into the genome of the animal and is expressed in the animal, resulting in the presence of protein in the transgenic animal.

There are several means by which such a gene can be introduced into the genome of the animal embryo so as to be chromosomally incorporated and expressed. One method is to transfect the embryo with the gene as it occurs naturally, and select transgenic animals in which the gene has integrated into the chromosome at a locus which results in expression. Other methods for ensuring expression involve modifying the gene or its control sequences prior to introduction into the embryo. One such method is to transfect the embryo with a vector (see above) containing an already modified gene. Other methods are to use a gene the transcription of which is under the control of a inducible or constitutively acting promoter, whether synthetic or of eukaryotic or viral origin, or to use a gene activated by one or more base pair substitutions, deletions, or additions (see above).

Introduction of the desired gene sequence at the fertilized oocyte stage ensures that the transgene is present in all of the germ cells and somatic cells of the transgenic animal and has the potential to be expressed in all such cells. The presence of the transgene in the germ cells of the transgenic "founder" animal in turn means that all its progeny will carry the transgene in all of their germ cells and somatic cells. Introduction of the transgene at a later embryonic stage in a founder animal may result in limited presence of the transgene in some somatic cell lineages of the founder; however, all the progeny of this founder animal that inherit the transgene conventionally, from the founder's germ cells, will carry the transgene in all of their germ cells and somatic cells.

Chimeric non-human mammals in which fewer than all of the somatic and germ cells contain the TSG-6 DNA of the present invention, such as animals produced when fewer than all of the cells of the morula are transfected in the process of producing the transgenic mammal, are also intended to be within the scope of the present invention.

The techniques described in Leder, U.S. Pat. No. 4,736,866 (hereby incorporated by reference) for producing transgenic non-human mammals may be used for the production of the transgenic non-human mammal of the present invention. The various techniques described in Palmiter, R. et al., *Ann. Rev. Genet.* 20:465–99 (1986), the entire contents of which are hereby incorporated by reference, may also be used.

The animals carrying the TSG-6 gene can be used to test compounds or other treatment modalities which may prevent, suppress or cure chronic inflammatory conditions mediated by TNF action on connective tissue cells. These tests can be extremely sensitive because of the ability to adjust the dose of an agent under test given to the transgenic animals of this invention. Such diseases include, but are not limited to rheumamtoid arthritis, granulomatous diseases, and the like. Transgenic animals according to the present invention can also be used as a source of cells for cell culture.

This invention is also directed to an antibody specific for an epitope of TSG-6 protein. In additional embodiments, the antibodies of the present invention are used in methods to detect the presence of, or measure the quantity or concentration of, TSG-6 protein in a cell, or in a cell or tissue extract, or a biological fluid. The antibodies may also be used in methods for measuring induction of expression of TSG-6 in a cell or in methods for identifying a compound capable of inducing the expression of TSG-6 in a cell. The antibodies may also be used to disrupt the action of TSG-6, thereby preventing or treating diseases associated with overproduction, or inappropriate production or action of TSG-6, such as inflammatory disorders including rheumatoid arthritis, infections and sepsis, as well as conditions associated with TNF-stimulated leukocyte adhesion.

The term "antibody" is meant to include polyclonal antibodies, monoclonal antibodies (mabs), chimeric antibodies, and anti-idiotypic (anti-Id) antibodies.

An antibody is said to be "capable of binding" a molecule if it is capable of specifically reacting with the molecule to thereby bind the molecule to the antibody. The term "epitope" is meant to refer to that portion of any molecule capable of being bound by an antibody which can also be recognized by that antibody. Epitopes or "antigenic determinants" usually consist of chemically active surface groupings of molecules such as amino acids or sugar side chains and have specific three dimensional structural characteristics as well as specific charge characteristics.

An "antigen" is a molecule or a portion of a molecule capable of being bound by an antibody which is additionally capable of inducing an animal to produce antibody capable of binding to an epitope of that antigen. An antigen may have one, or more than one epitope. The specific reaction referred to above is meant to indicate that the antigen will react, in a highly selective manner, with its corresponding antibody and not with the multitude of other antibodies which may be evoked by other antigens.

In order to predict antigenic epitopes present in the protein, the amino acid sequence is inspected visually or analyzed by computer, for example, using the program of PEPTIDESTRUCTURE (Jameson et al., *CABIOS* 4: 181–186 (1988)). This program allows determination of hydropathicity values which are then used to determine which peptide sequences within the overall protein sequence are likely to be most immunogenic based on their potential secondary structure. Such peptides may be synthesized chemically, or alternatively, and preferably, by recombinant DNA methods.

Such computer analysis of the sequence of the TSG-6 protein led to the selection of three sequences each of 15 amino acids from different parts of the molecule. These synthetic peptides were synthesized by the NYU Cancer Center Peptide Synthesis Laboratory. One sequence was selected on the basis of its high degree of homology with proteoglycan core/cartilage link protein/CD44, whereas the other two peptides were from other portions of the TSG-6 protein and showed no significant homology to other known proteins. A cysteine residue was added to the N- or C-terminus of each of the synthetic peptides to facilitate coupling to keyhole limpet hemocyanin (KLH), to be used as carrier protein. The 15-mers were coupled to KLH with the aid of the heterobifunctional reagent m-maleimidobenzoyl-N-hydroxysuccinimide ester (MBS) as described (Hartlow, E. et al., *Antibodies: A Laboratory Manual,* Cold Spring Harbor Laboratory Press, Cold Spring Harbor, N.Y., 1988)) and employed for the immunization of rabbits, using 2 rabbits per each synthetic peptide-KLH conjugate.

One of the pitfalls of generating antibodies to synthetic peptides is the possibility that an antibody so raised may fail to react with the native protein. For this reason, alternative approaches may be used. The TSG-6 protein may be prepared as a bacterially expressed fusion protein by using an appropriate expression plasmid (see Examples, below). The purified fusion protein is employed for the immunization of rabbits. Alternatively, such a fusion protein, or a synthetic peptide may be used to immunize a rodent for generation of a monoclonal antibody.

Polyclonal antibodies are heterogeneous populations of antibody molecules derived from the sera of animals immunized with an antigen.

Monoclonal antibodies are a substantially homogeneous population of antibodies to specific antigens. MAbs may be obtained by methods known to those skilled in the art. See, for example Kohler and Milstein, Nature 256:495–497 (1975) and U.S. Pat. No. 4,376,110. Such antibodies may be of any immunoglobulin class including IgG, IgM, IgE, IgA, and any subclass thereof. The hybridoma producing the mabs of this invention may be cultivated in vitro or in vivo. Production of high titers of mabs in vivo production makes this the presently preferred method of production. Briefly, cells from the individual hybridomas are injected intraperitoneally into pristane-primed Balb/c mice to produce ascites fluid containing high concentrations of the desired mAbs. MAbs of isotype IgM or IgG may be purified from such ascites fluids, or from culture supernatants, using column chromatography methods well known to those of skill in the art.

Chimeric antibodies are molecules different portions of which are derived from different animal species, such as those having a variable region derived from a murine mAb and a human immunoglobulin constant region. Chimeric antibodies and methods for their production are known in the art (Cabilly et al, Proc. Natl. Acad. Sci. USA 81:3273–3277 (1984); Morrison et al., Proc. Natl. Acad. Sci. USA 81:6851–6855 (1984); Boulianne et al., Nature 312:643–646 (1984); Neuberger et al., Nature 314:268–270 (1985); Taniguchi et al., European Patent Application 171496 (published Feb. 19, 1985); Kudo et al., European Patent Application 184187 (published Jun. 11, 1986); Robinson et al., International Patent Publication #PCT/US86/02269 (published 7 May 1987); Sun et al., Proc. Natl. Acad. Sci. USA 84:214–218 (1987); Better et al., Science 240:1041–1043 (1988)). These references are hereby incorporated by reference.

An anti-idiotypic (anti-Id) antibody is an antibody which recognizes unique determinants generally associated with the antigen-binding site of an antibody. An Id antibody can be prepared by immunizing an animal of the same species and genetic type (e.g. mouse strain) as the source of the mAb with the mAb to which an anti-Id is being prepared. The immunized animal will recognize and respond to the idiotypic determinants of the immunizing antibody by producing an antibody to these idiotypic determinants (the anti-Id antibody).

The anti-Id antibody may also be used as an "immunogen" to induce an immune response in yet another animal, producing a so-called anti-anti-Id antibody. The anti-anti-Id may bear structural similarity to the original mAb which induced the anti-Id. Thus, by using antibodies to the idiotypic determinants of a mAb, it is possible to identify other clones expressing antibodies of identical specificity.

Accordingly, mAbs generated against the TSG-6 protein of the present invention may be used to induce anti-Id antibodies in suitable animals, such as Balb/c mice. Spleen cells from such immunized mice are used to produce anti-Id hybridomas secreting anti-Id mAbs. Further, the anti-Id mAbs can be coupled to a carrier such as keyhole limpet hemocyanin (KLH) and used to immunize additional Balb/c mice. Sera from these mice will contain anti-anti-Id antibodies that have the binding properties of the original mAb specific for an TSG-6 protein epitope.

The term "antibody" is also meant to include both intact molecules as well as fragments thereof, such as, for example, Fab and $F(ab')_2$, which are capable of binding antigen. Fab and $F(ab')_2$ fragments lack the Fc fragment of intact antibody, clear more rapidly from the circulation, and may have less non-specific tissue binding than an intact antibody (Wahl et al., J. Nucl. Med. 24:316–325 (1983)).

It will be appreciated that Fab and $F(ab')_2$ and other fragments of the antibodies useful in the present invention may be used for the detection and quantitation of TSG-6 protein according to the methods disclosed herein for intact antibody molecules. Such fragments are typically produced by proteolytic cleavage, using enzymes such as papain (to produce Fab fragments) or pepsin (to produce $F(ab')_2$ fragments).

The antibodies, or fragments of antibodies, of the present invention may be used to quantitatively or qualitatively detect the presence of cells which express the TSG-6 protein on their surface or intracellularly. This can be accomplished by immunofluorescence techniques employing a fluorescently labeled antibody (see below) coupled with light microscopic, flow cytometric, or fluorimetric detection.

The antibodies of the present invention may be employed histologically, as in immunofluorescence or immunoelectron microscopy, for in situ detection of TSG-6 protein. In situ detection may be accomplished by removing a histological (cell or tissue) specimen from a subject and providing the a labeled antibody of the present invention to such a specimen. The antibody (or fragment) is preferably provided by applying or by overlaying on the biological sample. Through the use of such a procedure, it is possible to determine not only the presence of the TSG-6 protein but also its distribution on the examined tissue. Using the present invention, those of ordinary skill will readily perceive that any of a wide variety of histological methods (such as staining procedures) can be modified in order to achieve such in situ detection.

Additionally, the antibody of the present invention can be used to detect the presence of soluble TSG-6 molecules in a biological sample. Used in this manner, the antibody can serve as a means to monitor the presence and quantity of TSG-6 proteins in a subject having a condition associated with TNF induction of TSG-6, such as an inflammatory condition, an infection or sepsis, and the like.

Such immunoassays for TSG-6 protein typically comprise incubating a biological sample, such as a biological fluid, a tissue extract, freshly harvested cells such as lymphocytes or leucocytes, or cells which have been incubated in tissue culture, in the presence of a detectably labeled antibody capable of identifying TSG-6 protein, and detecting the antibody by any of a number of techniques well-known in the art.

The biological sample may be treated with a solid phase support or carrier (which terms are used interchangeably herein) such as nitrocellulose, or other solid support which is capable of immobilizing cells, cell particles or soluble proteins. The support may then be washed with suitable buffers followed by treatment with the detectably labeled TSG-6-specific antibody. The solid phase support may then be washed with the buffer a second time to remove unbound antibody. The amount of bound label on said solid support may then be detected by conventional means.

By "solid phase support or carrier" is intended any support capable of binding antigen or antibodies. Well-known supports, or carriers, include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Those skilled in the art will know many other suitable carriers for binding antibody or antigen, or will be able to ascertain the same by use of routine experimentation.

The binding activity of a given lot of anti-TSG-6 antibody may be determined according to well known methods. Those skilled in the art will be able to determine operative and optimal assay conditions for each determination by employing routine experimentation.

Other such steps as washing, stirring, shaking, filtering and the like may be added to the assays as is customary or necessary for the particular situation.

One of the ways in which the TSG-6-specific antibody can be detectably labeled is by linking the same to an enzyme and use in an enzyme immunoassay (EIA). This enzyme, in turn, when later exposed to an appropriate substrate, will react with the substrate in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods which employ a chromogenic substrate for the enzyme. Detection may also be accomplished by visual comparison of the extent of enzymatic reaction of a substrate in comparison with similarly prepared standards.

Detection may be accomplished using any of a variety of other immunoassays. For example, by radioactively labeling the antibodies or antibody fragments, it is possible to detect TSG-6 protein through the use of a radioimmunoassay (RIA) (Chard, T., "An Introduction to Radioimmune Assay and Related Techniques" (In: Work, T. S., et al., *Laboratory Techniques in Biochemistry in Molecular Biology,* North Holland Publishing Company, New York (1978), incorporated by reference herein). The radioactive isotope can be detected by such means as the use of a gamma counter or a liquid scintillation counter or by autoradiography. It is also possible to label the antibody with a fluorescent compound. When the fluorescently labeled antibody is exposed to light of the proper wave length, its presence can then be detected due to fluorescence. Among the most commonly used fluorescent labelling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as $^{152}$Eu, or others of the lanthanide series. These metals can be attached to the antibody using such metal chelating groups as diethylenetriaminepentaacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

The antibody molecules of the present invention may be adapted for utilization in an immunometric assay, also known as a "two-site" or "sandwich" assay. In a typical immunometric assay, a quantity of unlabeled antibody (or fragment of antibody) is bound to a solid support and a quantity of detectably labeled soluble antibody is added to permit detection and/or quantitation of the ternary complex formed between solid-phase antibody, antigen, and labeled antibody.

Typical, and preferred, immunometric assays include "forward" assays in which the antibody bound to the solid phase is first contacted with the sample being tested to "extract" the antigen from the sample by formation of a binary solid phase antibody-antigen complex. After a suitable incubation period, the solid support is washed to remove the residue of the fluid sample, including unreacted antigen, if any, and then contacted with the solution containing an unknown quantity of labeled antibody (which functions as a "reporter molecule"). After a second incubation period to permit the labeled antibody to complex with the antigen bound to the solid support through the unlabeled antibody, the solid support is washed a second time to remove the unreacted labeled antibody.

In another type of "sandwich" assay, which may also be useful with the antigens of the present invention, the so-called "simultaneous" and "reverse" assays are used. A simultaneous assay involves a single incubation step as the antibody bound to the solid support and labeled antibody are both added to the sample being tested at the same time. After the incubation is completed, the solid support is washed to remove the residue of fluid sample and uncompleted labeled antibody. The presence of labeled antibody associated with the solid support is then determined as it would be in a conventional "forward" sandwich assay.

In the "reverse" assay, stepwise addition first of a solution of labeled antibody to the fluid sample followed by the addition of unlabeled antibody bound to a solid support after a suitable incubation period is utilized. After a second incubation, the solid phase is washed in conventional fashion to free it of the residue of the sample being tested and the solution of unreacted labeled antibody. The determination of labeled antibody associated with a solid support is then determined as in the "simultaneous" and "forward" assays.

According to the present invention, it is possible to diagnose circulating antibodies in a subject which are specific for the TSG-6 protein. This is accomplished by means of an immunoassay, as described above, using the protein of the invention or a functional derivative thereof.

In cancer patients, circulating endotoxin levels are high (Harris, R. I. et al., *J. Clin. Path.* 37:467–470 (1984)), particularly in patients with tumor types known to be associated with an increased incidence of cachexia (Humberstone, D. A. et al., *Cancer* 62:1619–1624 (1988)). The presence of high endotoxin levels is probably not a direct result of the tumor per se, but rather reflects the general debility of the patients. Increased translocation from the gut of endogenous bacteria and endotoxins in critical illness is dependent on the presence of malnutrition and that impaired cell-mediated immunity may be an aggravating factor (Wilmore, D. W. et al., *Surgery* 104:917–923 (1988)). As cachectic cancer patients are malnourished and often exhibit suppression of cell-mediated immunity, translocation of endogenous organisms may account for higher levels of endotoxins. Cancer patients' peripheral blood mononuclear cells often show enhanced "spontaneous" TNF release in vitro (Aderka, D. et al., *Lancet* i:1190–1192 (1985)). TNF production in response to macrophage-activating agents is reduced in patients with advanced metastatic disease but not in cancer patients with only localized disease. These observations supported the notion that TNF production is ongoing in cancer patients, either due to sustained stimulation of monocytes/macrophages by tumor cells or to direct TNF production by tumor cells. TNF was detected in the serum of 50% of 226 cancer patients with active disease, compared to 3% of healthy sera and 18% of sera from disease-free cancer patients (Balkwill, F. et al., *Lancet ii:* 1229–1232 (1987)).

TNF levels are also elevated in a variety of bacterial and viral illnesses, including AIDS (Lahdevirta, J. et al., *Amer. J. Med.* 85:289–291 (1988)) and meningococcal meningitis and septicemia (Waage, A. et al., (*Lancet i:*355–357 (1987)). In a rat burn/infection model, levels of hepatic TNF mRNA increased 100% in rats subjected to burn+infection compared to controls or rats subjected to burns but no infection (Marano, M. A. et al., *Arch. Surg.* 123:1383–1388 (1988)). The animals subjected to burn and infection also showed a greater metabolic response (cachexia). Michie, H. R. et al., *Br. J. Surg.* 76:670–671 (1989), reviewed evidence that TNF is the principal mediator associated with the changes of severe sepsis.

Therefore, the methods of the present invention which are capable of measuring the response of a subject to a cytokine such as TNF or IL-1, or to bacterial endotoxin are useful in predicting the susceptibility of that individual to the debilitating effects of cancer or infectious disease. Similarly, the compositions of the present invention are useful in the prevention or treatment of such diseases, due to their ability to disrupt events set into motion by the action of TNF.

As used herein, the term "prevention" of a condition, such as an inflammatory response, infectious disease or a malignant tumor, in a subject involves administration of the TSG-6 peptide derivative, or antibody (see above) prior to the clinical onset of the disease. "Treatment" involves administration of the protective composition after the clinical onset of the disease. For example, successful administration of a TSG-6 peptide derivative or anti-TSG-6 antibody according to the invention after development of an inflammatory condition, a malignant tumor or an infection comprises "treatment" of the disease.

The TSG-6 protein, peptides or antibodies of the present invention may be administered by any means that achieve their intended purpose, for example, to treat rheumatoid arthritis or other inflammatory conditions, malignant tumors, infections, and the like.

For example, administration may be by various parenteral routes such as subcutaneous, intravenous, intradermal, intramuscular, intraperitoneal, intranasal, transdermal, or buccal routes. Alternatively, or concurrently, administration may be by the topical route or the oral route. Parenteral administration can be by bolus injection or by gradual perfusion over time.

A typical regimen for preventing, suppressing, or treating a condition such as chronic inflammation, as in rheumatoid arthritis, or a malignant tumor, comprises administration of an effective amount of the TSG-6 functional derivative, or an antibody thereto, administered over a period of one or several days, up to and including between one week and about six months.

It is understood that the dosage administered will be dependent upon the age, sex, health, and weight of the recipient, kind of concurrent treatment, if any, frequency of treatment, and the nature of the effect desired. The ranges of effective doses provided below are not intended to be limiting and represent preferred dose ranges. However, the most preferred dosage will be tailored to the individual subject, as is understood and determinable by one of skill in the art.

The total dose required for each treatment may be administered by multiple doses or in a single dose. The protein, functional derivative thereof or antibody may be administered alone or in conjunction with other therapeutics directed to the viral infection, or directed to other symptoms of the viral disease.

Effective amounts of the TSG-6 protein, functional derivative thereof, or antibody thereto, are from about 0.01 $\mu$g to about 100 mg/kg body weight, and preferably from about 10 $\mu$g to about 50 mg/kg body weight.

Preparations for parenteral administration include sterile aqueous or non-aqueous solutions, suspensions, and emulsions, which may contain auxiliary agents or excipients which are known in the art. Pharmaceutical compositions such as tablets and capsules can also be prepared according to routine methods.

Pharmaceutical compositions comprising the proteins, peptides or antibodies of the invention include all compositions wherein the protein, peptide or antibody is contained in an amount effective to achieve its intended purpose. In addition, the pharmaceutical compositions may contain suitable pharmaceutically acceptable carriers comprising excipients and auxiliaries which facilitate processing of the active compounds into preparations which can be used pharmaceutically.

Pharmaceutical compositions include suitable solutions for administration by injection or orally, and contain from about 0.01 to 99 percent, preferably from about 20 to 75 percent of active component (i.e., the TSG-6 protein or antibody) together with the excipient. Pharmaceutical compositions for oral administration include tablets and capsules. Compositions which can be administered rectally include suppositories.

Chondroitin-sulfate-rich proteoglycan is an essential component of the matrix of cartilage since it enables the tissue to resist compression during load bearing. Loss of proteoglycan, such as occurs in rheumatoid arthritis, osteoarthritis and other joint diseases, results in severe impairment of the function of cartilage. TNF and IL-1 are known to cause degradation of this proteoglycan in cartilage (Saklatvala, J. et al., *Biochem. J.* 224:461 (1984); *J. Exp. Med.* 162:1208 (1985); Saklatvala, J., *Nature* 322:547 (1986)), and to inhibit its re-synthesis. In the extracellular matrix, proteoglycan core noncovalently binds to a hyaluronic acid chain through two link proteins that bind to both the core protein of the proteoglycan and to the hyaluronic acid chain, thereby stabilizing the aggregates.

The N-terminal half of TSG-6 protein has significant homology with cartilage proteoglycan core protein and link protein. Thus, according to the present invention, in connective tissue, TNF or IL-1 induces the secretion of TSG-6, which interacts with link proteins or the proteoglycan core protein through a shared homology domain. TSG-6 may compete either with link protein or with proteoglycan core protein for binding to the hyaluronic acid chain, resulting in destabilization of the structure of the proteoglycan aggregates, which causes proteoglycan release.

The C-terminal half of TSG-6 has a high degree of homology with the interaction domain of the complement C1r-A chain. The complement components C1r and C1s (which interacts with C1r through the interaction domain) are serine proteases. Therefore, upon binding to a hyaluronic acid chain via its N-terminal portion, TSG-6 may attract proteases through its C1r-like domain. This results in the proteases causing limited proteolysis of the proteoglycan. See FIG. 17 for a schematic illustration of this interaction.

Thus, according to the present invention, antibodies specific to the N-terminal portion of the TSG-6 protein, or functional derivatives of TSG-6, preferably peptides from the N-terminal portion having homology to the proteoglycan core protein or to the cartilage link protein, are useful in inhibiting TNF-induced, TSG-6-mediated, breakdown of proteoglycan in cartilage. In addition, antibodies specific to the C-terminal portion of the TSG-6 protein, or functional derivatives of TSG-6, preferably peptides from the C-terminal potion having homology to C1r, are useful in inhibiting TNF-induced, TSG-6-mediated, breakdown of proteoglycan in cartilage. Therefore, according to the present invention, diseases involving proteoglycan breakdown, such as, for example, rheumatoid arthritis and other inflammatory connective tissue disorders, may be treated using antibodies specific for epitopes of TSG-6 or peptides corresponding to portions of TSG-6 as described above.

Cartilage cells (chondrocytes) may be used for production of TSG-6, or for evaluating the efficacy of treatments using TSG-6-specific antibodies or TSG-6 functional derivatives such as peptides. Cartilage cells are one of the family of connective tissue cells, and these cells are highly responsive to the pro-inflammatory cytokines, TNF and IL-1. TNF and IL-1 stimulate resorption of cartilage (Saklatvala, J., supra), a major feature of inflammatory diseases such as rheumatoid arthritis. Furthermore, IL-6 is secreted by chondrocytes upon treatment with TNF or IL-1 (Guerne, P.-A. et al., supra) as part of an inflammatory process, similar to the response to FS-4 fibroblasts to these cytokines.

Cells are isolated from human articular cartilage by sequential enzymatic digestion using standard procedures (Pieter, A. et al., *Arthritis Rheum.* 25:1217 (1982); Malejczyk, J. et al., *Clin. Exp. Immunol.* 75:477 (1989)). An exemplary method for preparing cartilage chips (1 cm$^2$) from the superficial layers of cartilage, avoiding calcified layers, follows. The cartilage chips are first treated with hyaluronidase (0.5 mg/ml for 15 min at room temperature) to remove any other cell types that might potentially adhere to the cartilage surface, followed by five washes with PBS. The chips are then minced into small pieces of about 0.5 mm$^3$ and digested with collagenase (2 mg/ml) and DNase (0.1 mg/ml) in the presence of 10% FCS for 18 h at 370° C. in a gyratory shaker. The resulting chondrocytes are cultured in 175-cm$^2$ tissue culture flasks in DMEM and 10% FCS. After 24 h, cells are detached by gentle pipetting, washed, and recultured for 4 hours in the presence of TNF (20 ng/ml) at a density of 5×10$^7$ cells/75 cm$^2$ flask. Total RNA is isolated from the TNF treated cells by the guanidine thiocyanate/hot phenol method (Feramisco, J. R. et al., *J. Biol. Chem.* 257:11024 (1982)). Northern blot analysis is performed to test for induction of TSG-6 mRNA; alternatively, antibodies specific for TSG-6 can be used to test extracts or supernatants of chondrocytes for production of TSG-6 protein, as described herein.

The preferred animal subject of the present invention is a mammal. By the term "mammal" is meant an individual belonging to the class Mammalia. The invention is particularly useful in the treatment of human subjects, although it is intended for veterinary uses as well.

The present invention provides methods for evaluating the presence and the level of normal or mutant TSG-6 protein or mRNA in a subject. For example, over-expression of TSG-6 in response to stimulation with TNF or IL-1, or an exogenous stimulus such as a bacterial infection, may serve as an important predictor of the inflammatory or septic response. By providing a means to measure the quantity of TSG-6 mRNA in a hybridization assay or to measure TSG-6 protein, as in an immunoassay, the present invention provides a means for detecting susceptibility in a subject to development of an inflammatory condition, such as rheumatoid arthritis, to infectious and septic conditions, and the like.

Oligonucleotide probes encoding various portions of the TSG-6 DNA sequence are used to test cells from a subject for the presence TSG-6 DNA or mRNA. A preferred probe would be one directed to the nucleic acid sequence encoding at least 12 and preferably at least 15 nucleotides of the TSG-6 sequence. Qualitative or quantitative assays can be performed using such probes. For example, Northern analysis (see Examples below) is used to measure expression of an TSG-6 mRNA in a cell or tissue preparation.

Such methods can be used even with very small amounts of DNA obtained from an individual, following use of selective amplification techniques. Recombinant DNA methodologies capable of amplifying purified nucleic acid fragments have long been recognized. Typically, such methodologies involve the introduction of the nucleic acid fragment into a DNA or RNA vector, the clonal amplification of the vector, and the recovery of the amplified nucleic acid fragment. Examples of such methodologies are provided by Cohen et al. (U.S. Pat. No. 4,237,224), Sambrook et al. (supra), etc.

Recently, an in vitro enzymatic method has been described which is capable of increasing the concentration of such desired nucleic acid molecules. This method has been referred to as the "polymerase chain reaction" or "PCR" (Mullis, K. et al., *Cold Spring Harbor Symp. Ouant. Biol.* 51:263–273 (1986); Erlich H. et al., EP 50,424; EP 84,796, EP 258,017, EP 237,362; Mullis, K., EP 201,184; Mullis K. et al., U.S. Pat. No. 4,683,202; Erlich, H., U.S. Pat. No. 4,582,788; and Saiki, R. et al., U.S. Pat. No. 4,683,194).

The polymerase chain reaction provides a method for selectively increasing the concentration of a particular nucleic acid sequence even when that sequence has not been previously purified and is present only in a single copy in a particular sample. The method can be used to amplify either single- or double-stranded DNA. The essence of the method involves the use of two oligonucleotide probes to serve as primers for the template-dependent, polymerase mediated replication of a desired nucleic acid molecule.

The precise nature of the two oligonucleotide probes of the PCR method is critical to the success of the method. As is well known, a molecule of DNA or RNA possesses directionality, which is conferred through the 5'–3' linkage of the phosphate groups of the molecule. Sequences of DNA or RNA are linked together through the formation of a phosphodiester bond between the terminal 5' phosphate group of one sequence and the terminal 3' hydroxyl group of a second sequence. Polymerase dependent amplification of a nucleic acid molecule proceeds by the addition of a 5' nucleotide triphosphate to the 3' hydroxyl end of a nucleic acid molecule. Thus, the action of a polymerase extends the 3' end of a nucleic acid molecule. These inherent properties are exploited in the selection of the oligonucleotide probes of the PCR. The oligonucleotide sequences of the probes of the PCR method are selected such that they contain sequences identical to, or complementary to, sequences which flank the particular nucleic acid sequence whose amplification is desired.

More specifically, the oligonucleotide sequence of the "first" probe is selected such that it is capable of hybridizing to an oligonucleotide sequence located 3' to the desired sequence, whereas the oligonucleotide sequence of the "second" probe is selected such that it contains an oligonucleotide sequence identical to one present 5' to the desired region. Both probes possess 3' hydroxy groups, and therefore can serve as primers for nucleic acid synthesis.

In the PCR, the reaction conditions are cycled between those conducive to hybridization and nucleic acid polymerization, and those which result in the denaturation of duplex molecules. In the first step of the reaction, the nucleic acids of the sample are transiently heated, and then cooled, in order to denature any double-stranded molecules which may be present. The "first" and "second" probes are then added to the sample at a concentration which greatly exceeds that of the desired nucleic acid molecule. When the sample is incubated under conditions conducive to hybridization and polymerization, the "first" probe will hybridize to the nucleic acid molecule of the sample at a position 3' to the sequence to be amplified. If the nucleic acid molecule of the sample was initially double-stranded, the "second" probe will hybridize to the complementary strand of the nucleic acid molecule at a position 3' to the sequence which is the complement of the sequence whose amplification is desired. Upon addition of a polymerase, the 3' ends of the "first" and (if the nucleic acid molecule was double-stranded) "second" probes will be extended. The extension of the "first" probe will result in the synthesis of an oligonucleotide having the exact sequence of the desired nucleic acid. Extension of the "second" probe will result in the synthesis of an oligonucleotide having the exact sequence of the complement of the desired nucleic acid.

The PCR reaction is capable of exponential amplification of specific nucleic acid sequences because the extension product of the "first" probe, of necessity, contains a sequence which is complementary to a sequence of the "second" probe, and thus can serve as a template for the production of an extension product of the "second" probe. Similarly, the extension product of the "second" probe, of necessity, contains a sequence which is complementary to a sequence of the "first" probe, and thus can serve as a template for the production of an extension product of the "first" probe. Thus, by permitting cycles of polymerization, and denaturation, a geometric increase in the concentration of the desired nucleic acid molecule can be achieved. Reviews of the PCR are provided by Mullis, K. B. (*Cold Spring Harbor Symp. Ouant. Biol.* 51:263–273 (1986)); Saiki, R. K., et al. (*Bio/Technology* 3:1008–1012 (1985)); and Mullis, K. B., et al. (*Meth. Enzymol.* 155:335–350 (1987)).

Having now generally described the invention, the same will be more readily understood through reference to the following examples which are provided by way of illustration, and are not intended to be limiting of the present invention.

EXAMPLE I

Preparation of cDNA Library from TNF-Treated FS-4 Cells and Isolation of TNF-Inducible cDNA Materials

*E. coli*-derived recombinant human TNF (specific activity, $3\times10^7$ U/mg) was supplied by M. Tsujimoto of the Suntory Institute for Biomedical Research, Osaka, Japan. *E. coli*-derived recombinant human IL-1α (specific activity, $1\times10^9$ U/mg) was received from Alvin Stern and Peter Lomedico, Hoffmann-LaRoche, Inc., Nutley, N.J. *E. coli*-derived human gamma interferon (IFN-τ) (specific activity, $2.1\times10^7$ U/mg) was provided by Biogen, Cambridge, Me. *E. coli*-derived human IFN-β (Betaseron, specific activity, $2\times10^8$ U/mg) was obtained from Triton Biosciences, Alameda, Calif. Epidermal growth factor (EGF), platelet-derived growth factor (PDGF) and transforming growth factor-β (TGF-β) were purchased from Collaborative Research, INc., Bedford, Me. Poly(I)-poly(C) was from P-L Biochemicals, Inc., Milwaukee, Wis. $N^6$-2'-O-dibutyl adenosine cyclic 3',5'-monophosphate, cycloheximide, forskolin, 12-O-tetradecanoylphorbol 13-acetate (TPA), the calcium ionophore A23187, and isobutylmethylxanthine were purchased from Sigma Chemical Co., St. Louis, Mont. The pHe7 plasmid, used as a source of internal reference cDNA (Kaczmarek, L. et al., *J. Cell Biol.* 104:183–187 (1987), was supplied by P. B. Sehgal, Rockefeller University, New York, N.Y.

Cell Culture

The human diploid FS-4 foreskin fibroblast cell line (Vilcek, J. et al., *Proc. Natl. Acad. Sci.* USA 70:3909–3913 (1973)) was used at passage level 15 in all experiments. FS-4 cells were grown in Eagle minimal essential medium (E-MEM) supplemented with 6 mM HEPES, 3 mM Tricine, 50 μg/ml gentamicin, and 5% heat inactivated (56° C., 30 min) fetal bovine serum (FBS; GIBCO Laboratories, Grand Island, N.Y.). For experiments, $4\times10^6$ cells were seeded in 175 cm$^2$ Falcon flasks, incubated at 37° C., and allowed to grow to confluence over 6 days. The confluent monolayers were washed once with phosphate buffered saline and replenished with E-MEM containing 0.25% FBS. The cultures were incubated in this medium for another 72 h at 37° C. to let the cells become quiescent and then treated with the appropriate agents, as specified herein.

Preparation of cDNA and Construction of cDNA Library

Total cytoplasmic RNA was isolated from quiescent FS-4 cells treated for 3 h with TNF (10 ng/ml) as described previously (Lin, J.-X. et al., *J. Biol. Chem.* 262:11908–11911 (1987)). Poly(A)$^+$ RNA was selected by one cycle of binding to oligo(dT)-cellulose (type 7; P-L Biochemicals). Double stranded cDNA was made from 10 μg of poly(A)$^+$ by using the cDNA synthesis system of Bethesda Research Laboratories, Gaithersburg, Md. The double stranded cDNA was methylated with EcoRI methylase and made blunt-ended with T4 DNA polymerase. EcoRI linkers were ligated onto the cDNA, which was then restricted with EcoRI. The resulting cDNA greater than 600 base pairs in size was fractionated and separated from the linker fragments by Sepharose CL4B column chromatography and ligated into the EcoRI site of lambda gt10. The library was packed in vitro with Gigapack packaging extract (Stratagene).

Differential Screening of the cDNA Library

The lambda gt10 cDNA library was plated on E. coli LE392 at a density of 1000 PFU/dish (150 mm diameter). Nitrocellulose filters were used to prepare duplicate plaque lifts of each plats. Prehybridization and hybridization of filters with $^{32}$P-labeled single-stranded cDNA probe were performed as described (Leonard, D. G. B. et al., Molec. Cell. Biol. 7:3156–3167 (1987)). Probes were synthesized by using the Bethesda Research Laboratories cDNA synthesis system with 10 μg poly(A)$^+$ RNA. The first strand synthesis reaction was adjusted to contain 0.5 mM each of DATP, dGTP, and dTTP, 0.1 mM dCTP, 100 μg/ml dactinomycin, and 200 μCi of [α-$^{32}$p]dCTP (3000 Ci/mmol; ICN Pharmaceuticals, Inc., Irvine, Calif.). After synthesis of the cDNA, the RNA was removed by incubation in 0.2M NaOH at 70° C. for 20 min. The reaction was neutralized with HCl and the cDNA was ethanol precipitated in the presence of 2M ammonium acetate. The pellet was suspended in 200 μl of TE (10 mM Tris HCl, pH 8.0, 1 mM EDTA) and added to the hybridization solution and filters. One of two probes was used to hybridize to each of the two replica filters; one was made from untreated FS-4 cells, and the other was made from FS-4 cells treated for 3 h with TNF (10 ng/ml). After hybridization, the filters were washed in 2×SSC (1×SSC is 0.15M NaCl plus 0.015M sodium citrate) -0.1% sodium dodecyl sulfate (SDS) at 65° C. for 1 h with one or two changes. Filters ere exposed to Kodak XAR-5 film for 1–2 days with an intensifying screen at −70° C. Plaques that showed different intensities of the hybridization signal with the two probes were selected. these clones were subjected to one further round of differential screening, and the plaques were purified.

Subcloning of the cDNA, Inserts, and Cross Hybridization Studies

E. coli LE392 cells in soft 0.7% agarose were poured into 150 mm plates. The lambda clones were then spotted on the plates in a grid array. Four nitrocellulose filters were lifter from each plate, processed, and stored until use. To prepare cDNA inserts from plaque-purified recombinant clones, 10 ml of liquid lysate was clarified and digested with 2 μg of DNase I per ml to remove contaminated chromosomal DNA. Then 2 ml of 2.5% SDS-0.5M Tris HCl (pH9.5)-0.25M EDTA was added, and plates were incubated at 65° C. for 15 min to lyse the phages. The solution was then cooled to room temperature before 2.0 ml of 10M ammonium acetate was added. The sample was chilled on ice for 20 min and centrifuged at 15,000×g at 4° C. for 10 min to obtain the DNA pellet. The pellet was suspended in 100 μl TE buffer containing 2 μg RNase A (Boehringer) per ml, and cut with the restriction enzyme EcoRI. The cDNA insert was isolated and subcloned into the EcoRI site of an M13mp19 vector. The cDNA inserts to be used as probes for cross-hybridization and Northern (RNA) blot experiments were prepared from the recombinant M13 clones by restriction with EcoRI to minimize background. The probes were prepared earlier. The hybridization conditions ere essentially as described above for the differential screening experiments.

Northern Blot Analysis

Cytoplasmic RNA was fractionated on a 1% agarose gel containing formaldehyde and blotted onto Zeta-probe blotting membranes (Bio-Rad Laboratories, Richmond, Calif.). Cytoplasmic RNA was loaded at 10 μg/lane. Prehybridization and hybridization of Northern blots were performed as described (Lin, J.-X. et al., supra). Filters were probed with 32P-labeled cDNA insert from recombinant M13 clones and/or with 32P-labeled internal reference pHe7 insert. Northern blots were quantified with a laser densitometer.

Sequence Analysis

Single stranded DNA templates from recombinant M13 clones were prepared, and several hundred nucleotides from each end of the cDNA were determined by the dideoxynucleotide-chain termination method (Sanger, F. et al., Proc. Natl. Acad. Sci. USA 74:5463–5468 (1977)). The partial nucleotide sequences were compared with sequences entered in GenBank (release 60.0).

RESULTS

FS-4 cells were grown to confluence, then switched to medium with 0.25% fetal bovine serum (FBS) and incubated for 72 h at 37° C. The cells were then exposed to recombinant human TNF (10 ng/ml). Cytoplasmic RNA was isolated (Lin, J.-X. et al., J. Biol. Chem. 262, 11908, 1987) after a 3-h incubation with TNF. A 3 h incubation with TNF was chosen for the following reason. It is known that TNF induces an increase in the level of some mRNAs within 20–30 min in quiescent FS-4 cells, but some of these "early response" mRNAs are elevated only transiently, for 30–120 min (e.g., c-fos and c-myc mRNA; see Lin, J.-X. et al., supra). Although such immediate early response gene products may be important for turning on other genes, the fact that they are induced only transiently suggested that they are not the actual effector molecules responsible for the phenotypic changes induced by TNF. Therefore, a search was initiated for cDNAs corresponding to messages that are more stably elevated after TNF treatment.

Poly(A)+ RNA was isolated from the cytoplasmic RNA by and double-stranded cDNA was synthesized. The resulting cDNA library from TNF-treated FS-4 cells, consisting of 2×10$^6$ recombinant clones, was screened for TNF-inducible gene sequences by differential hybridization with [$^{32}$P] cDNA probes prepared from poly(A)+ RNA from control and from TNF-treated FS-4 cells. Plaques which gave a strong signal when probed with cDNA from TNF-treated cells, but not when probed with control cell cDNA, were picked as presumptive TNF-inducible genes.

Approximately 3×10$^4$ plaques were screened, and 47 were scored as clearly inducible after two rounds of screening. They were designated TSG 1–47 (TSG="TNF-stimulated gene sequence"). To determine the number of different mRNAs represented among the TSG clones selected by differential screening, the inserts were tested for sequence homology by cross-hybridization. A total of 44 cloned cDNAs have been examined by cross-hybridization to each other. These experiments revealed a total of eight distinct, non-crossreacting cDNAs. As summarized in Table 2, below, some of the cDNAs were represented among the 44 clones with a high frequency (TSG-8 and TSG-14) while others were much less abundant (TSG-21, TSG-27 and TSG-37). The size of the corresponding mRNAs ranged from 0.8 to 4.5 kb.

TABLE 2

Abundance of Individual TSG cDNAs Among 44 TNF-specific cDNA Clones

| cDNA | Abundance[a] | Approximate size of corresponding mRNA (kb) |
|---|---|---|
| TSG-1 | 6 | 1.6 |
| TSG-6 | 6 | 1.5 |
| TSG-8 | 11 | 1.1 |
| TSG-12 | 3 | 4.5 |
| TSG-14 | 13 | 2.3 |
| TSG-21 | 1 | 2.4 |
| TSG-27 | 2 | 2.4 |
| TSG-37 | 2 | 0.8 |

[a]Each of the 44 cDNA inserts was isolated from the lambda gt10 vector and subcloned into the M13mp19 vector. Inserts from the M13 vector were [32p]-labeled by nick translation and hybridized with each of the 44 lambda cDNA clones. Cross-hybridization was taken as evidence that the cDNAs were derived from the same mRNA species.

EXAMPLE II

Kinetics of Induction of TNF-Induced mRNAs

To ascertain that the eight distinct TSG cDNAs isolated indeed correspond to mRNAs whose levels are up-regulated in FS-4 cells by TNF treatment, quiescent FS-4 cultures were treated with TNF (20 ng/ml) for different intervals ranging from 0.5 to 16 h, cytoplasmic RNA was isolated (Lin, J.-X. et al.,supra) and mRNA levels corresponding to each of the eight cDNAs were quantitated by Northern blot analysis and densitometric scanning of the autoradiograms (FIGS. 1 and 2). The increase in mRNA levels ranged from about 3-fold (TSG-21) to over 100-fold (TSG-6 and TSG-8).

Three different patterns of mRNA stimulation were noted. The first pattern was characterized by an increase to peak levels by 2–4 h, followed by a gradual decrease in mRNA levels (TSG-1 and TSG-6). The second pattern showed a rapid increase of mRNA levels to a maximum by 1.5 to 4 h, followed by a plateau until at least 16 h (TSG-8, TSG-12, TSG6–14 and TSG-37). The third pattern was characterized by a possible initial decrease, followed by a slow gradual increase in mRNA levels throughout the 16-h observation period (TSG-21 and TSG-27).

EXAMPLE III

Partial Sequencing of TSG cDNAs

To determine whether the isolated cDNAs were homologous to previously identified genes, all eight cDNAs were partially sequenced (300–400 bp) and the sequences determined were checked against sequences available in GenBank. Sequences of four cDNAs (TSG-1, TSG-8, TSG-21 and TSG-27) were found to be identical to earlier identified genes. Of these, TSG-1 corresponded to the gene for β-thromboglobulin-like protein 3°–10° C. (Schmid, J. et al., *J. Immunol.* 139:250 (1987)), also known as IL-8. TSG-8 was identical to the recently cloned gene for "monocyte chemotactic and activating factor" (MCAF) (Matsushima, K. et al., *Cytokine* 1:2 (1989)). TSG-21 and TSG-27 were found to be identical to the collagenase and stromelysin genes, respectively, and TSG-37 was found to encode metallothionein II. The other three partial cDNA sequences showed no significant homologies with known genes, indicating that they represented hitherto unidentified gene sequences.

Induction of IL-8 (=TSG-1) by TNF and by IL-1 was recently observed by others (Matsushima, K. et al., supra; *J. Exp. Med.* 167:1883 (1988)). IL-8, a neutrophil chemotactic factor, is structurally related to several members of a family of inflammatory cytokines that include platelet factor-4 (PF-4), the IFN-τ-inducible protein IP-10, the PDGF-inducible gene JE, proteins termed MIP-1 and MIP-2, and GRO (Matsushima, K. et al., supra; Larsen, C. G. et al., *Science* 243:1464 (1989)). Most of these proteins appear to be chemotactic.

MCAF (=TSG-8) induction in human fibroblasts by TNF and IL-1 has been recently described (Matsushima, K. et al., supra). Interestingly, MCAF shows significant amino acid sequence similarity (21%) with IL-8, and they both have four cysteines at similar positions.

Collagenase (=TSG-21) was also reported earlier to be TNF-inducible in synovial cells and fibroblasts (Dayer et al., supra). It is very likely that the ability of TNF to induce collagenase is related to TNF's role in tissue remodeling during inflammation. While the induction of stromelysin by TNF has not been reported, stromelysin mRNA was recently shown to be inducible by IL-1 (Quinones, S. et al., *J. Biol. Chem.* 264:8339 (1989)). Like collagenase, stromelysin is a collagen-degrading metalloproteinase, and both can also degrade fibronectin, laminin and cartilage proteoglycans. Both collagenase and stromelysin are thought to be important in the increased extracellular matrix degradation occurring in rheumatoid arthritis.

Finally, metallothionein II (MT-II) (=TSG-37) has been shown to be inducible by various stresses, including heavy metal challenge, injection of lipopolysaccharide as well as by cytokines including interferons and IL-1 (Karin, M., *Cell* 41:9–10 (1985)). In addition to its ability to bind heavy metal ions, MT-II may also act as a scavenger of free radicals released by activated macrophages and neutrophils during an inflammatory response. MT-II induction would thus serve a protective role in the prevention of tissue injury (Thornalley, P. J., *Biochim. Biophys. Acta* 827:36–44 (1985).

It is significant that all five TSG cDNAs identified by sequencing correspond to genes coding for proteins important in the inflammatory process. These results support the utility of the present approach of cloning TNF-inducible cDNAs from human fibroblasts in the identification of novel genes with important functions in immune responses and inflammation.

EXAMPLE IV

Patterns of TSG mRNA Induction by Different Cytokines and Other Agents

Table 3 provides a summary of a large number of experiments in which levels of mRNAs corresponding to the 8 distinct TSG cDNAs were determined in FS-4 cells exposed to various agents by Northern blot analysis. Three of the mRNAs (corresponding to TSG-8, TSG-12 and TSG-14) were inducible by the protein synthesis inhibitor, cycloheximide (CHX). In some cases the addition of CHX either did not block (TSG-12 and TSG-14) or increased (TSG-1, TSG-6 and TSG-8) mRNA inducibility by TNF, suggesting that the increase in the mRNA levels is the result of a direct action of TNF, not requiring a protein intermediate. In contrast, induction of the remaining 3 mRNAs by TNF was inhibited or reduced in the presence of CHX. Five of the mRNAs were inducible by IFN-β, but only two of these responded to IFN-τ. Simultaneous treatment with IFN-β reduced inducibility of TSG-1 (=IL-8) mRNA by TNF, but increased the inducibility of TSG-6 and TSG-37 mRNAs. All mRNAs were inducible by IL-1 and by the double-stranded RNA poly(I)·poly(C) or the phorbol ester 12-O-tetradecanoyl phorbol 13-acetate (TPA), but the efficiency of induction by these agents varied. Epidermal growth factor (EGF) was moderately efficient in increasing TSG-21 (=collagenase) and TSG-27 (=stromelysin) mRNA levels, and weakly stimulated several other mRNAs. PDGF and transforming growth factor-β (TGF-β) were only weakly effective, as were dibutyryl cyclic AMP (dBcAMP) and the phosphodiesterase inhibitor, isobutyl methyl xanthine (IBMX).

As summarized in Table 3, it is apparent that none of the mRNAs responded exclusively to TNF. However, at least two mRNAs (TSG-1/IL-8 and TSG-6) were particularly strongly induced by TNF compared to any other stimulus. It is interesting that TSG-1/IL-8 and TSG-6 mRNAs have similar patterns of inducibility (except for an apparent difference in the actions of IFN-β and IFN-τ on induction by TNF). It is also apparent that the pattern of inducibility of TSG-8 closely resembled that of TSG-12; TSG-21 (collagenase) and TSG-27 (stromelysin) mRNA also had similar patterns of inducibility. TSG-37 mRNA (metallothionein II) was strongly inducible by both TNF and IFN-β.

Among the six lambda clones which cross-hybridized with TSG-6 cDNA, the lambda5-TSG-6 clone had the longest insert, of about 1.4 kb, and was therefore used for sequence analysis. The approximately 1.4 kb lambda5-TSG-6 insert was subcloned into the EcoRI site of M13mp18 bacteriophage in both orientations. To insure fidelity of sequence determination, directional deletion clones were generated by the ExoIII/S1 method (Henikoff, S. supra) in both directions within the M13 clones. The deletion clones were then used to determine the nucleotide sequence by the dideoxynucleotide chain termination method (Sanger, F. et al., supra).

The TSG-6 cDNA was found to comprise 1414 bases, apparently consisting of a 69-base 5' untranslated region, a continuous open reading frame of 831 bases and a 3' untranslated region (FIGS. 3A–3C). Within the 3' untranslated region, there were multiple AT-rich regions. The corresponding mRNA sequence AUUUA is thought to confer instability (Shaw, G. et al., supra), resulting in rapid message degradation, and may explain the decline in the TSG-6 mRNA level seen after 4 h of continuous treatment with TNF (see FIG. 1). A consensus polyadenylation signal (AATAAA) was also located at the 3' end.

The largest open reading frame predicted a polypeptide of 277 amino acids. No other open reading frame with a

TABLE 3

Effect of various treatments on TSG mRNA levels in FS-4 cells

Relative increase in mRNA level

| Treatment[a] | TSG-1 (IL-8) | TSG-6 | TSG-8 (MCAF) | TSG-12 | TSG-14 | TSG-21 (Collagenase) | TSG-27 (Stromelysin) | TSG-37 (MT-II) |
|---|---|---|---|---|---|---|---|---|
| TNF | +++ | +++ | +++ | ++++ | ++++ | ++ | ++ | +++ |
| CHX | 0 | 0 | + | +++ | + | 0 | 0 | 0 |
| TNF + CHX | ++++ | ++++ | ++++ | ++++ | ++++ | 0 | 0 | + |
| IFN-beta | 0 | 0 | ++ | + | 0 | ++ | ++ | +++ |
| IFN-gamma | 0 | 0 | ++ | + | 0 | 0 | 0 | 0 |
| TNF + IFN-beta | + | ++++ | +++ | ++++ | ++++ | ++ | ++ | ++++ |
| TNF + IFN-gamma | + | +++ | ++++ | ++++ | ++++ | ++ | ++ | +++ |
| IL-1 | + | + | ++ | ++++ | ++++ | ++ | ++ | ++ |
| EGF | 0 | 0 | + | + | + | ++ | ++ | + |
| PDGF | 0 | 0 | + | + | + | 0 | 0 | 0 |
| TGF-beta | 0 | 0 | 0/+ | 0 | 0 | 0 | 0 | 0 |
| Poly(I).poly(C) | + | + | +++ | ++ | ++ | ++ | ++ | + |
| TPA | + | + | ++ | ++ | + | ++++ | ++++ | + |
| A23187 | + | + | ++ | ++ | 0 | ND | ND | 0 |
| Forskolin | 0 | 0/+ | 0 | 0 | 0 | 0 | 0 | 0 |
| dBcAMP | 0 | 0 | + | + | 0 | ND | ND | 0/+ |
| IBMX | 0 | 0/+ | + | + | 0 | 0 | 0 | 0 |

[a]Growth arrested FS-4 cells were treated with the following agents: TNF (20 ng/ml), CHX (10 ug/ml), IFN-beta (500 U/ml), IFN-gamma (100 U/ml), IL-1-alpha (1 ng/ml), EGF (25 ng/ml), PDGF (5 ng/ml), TGF-beta (2 ng/ml), poly(I).poly(C) (50 ug/ml), TPA (100 ng/ml), A23187 (1 uM), forskolin (10 uM), dBcAMP (100 uM), or IBMX (100 uM). All treatments were for 2 h, except that TSG-21 and -27 nRNA levels were determined after 16 h of treatment. (Since longer periods of treatment with a mixture of TNF and CHX were toxic, TSG-21 and -27 mRNA levels in the groups treated with TNF and CHX were determined at 4 h after the onset of treatment.) Total cellular RNA was isolated and fractionated on a 1% agarose gel containing formaldehyde; the RNA was then subjected to Northern blot analysis as described in the Materials and Methods. Relative increases in each of the TSG mRNA levels were quantitated by densitometric scanning of the autoradiograms: 0 indicates no increase in the mRNA level compared to the control mRNA level (no treatment); +, ++, +++, ++++ indicates relative increase in the mRNA level after treatment as compared with untreated control. For each of the individual TSG mRNA species, the highest density band(s) was (were) assigned ++++, and the relative densities of other mRNAs bands in the same experiment were then scored accordingly. ND, not determined.

EXAMPLE V

Figure 1A:
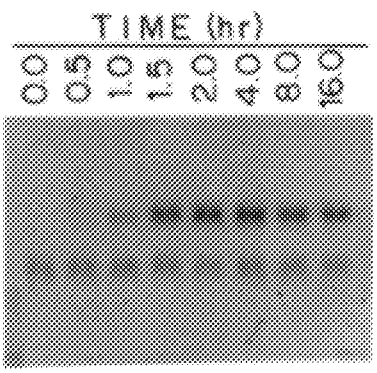
Figure 1B:
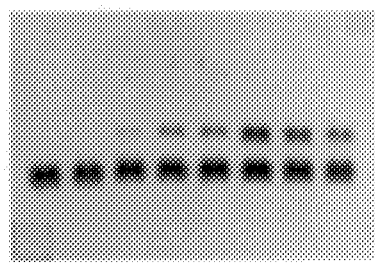
Figure 1C:
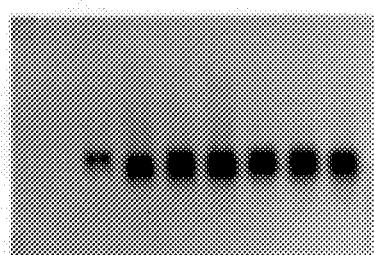
Figure 1D:
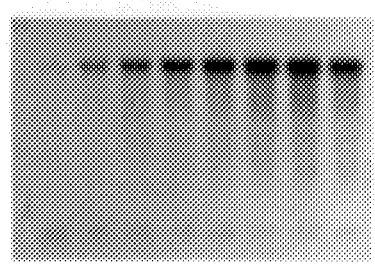
Figure 2F:
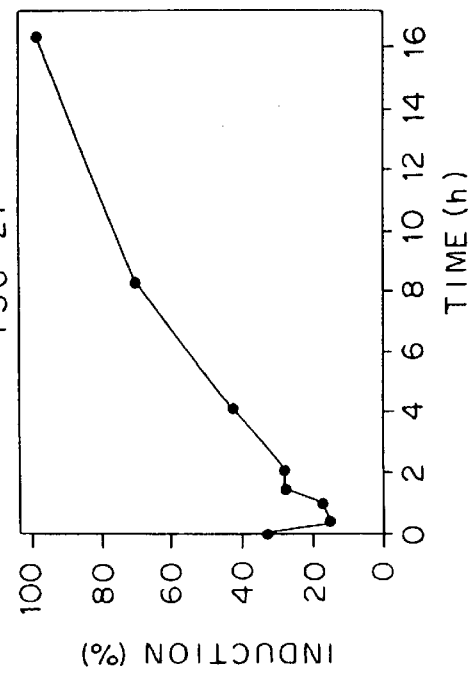
Figure 2H:
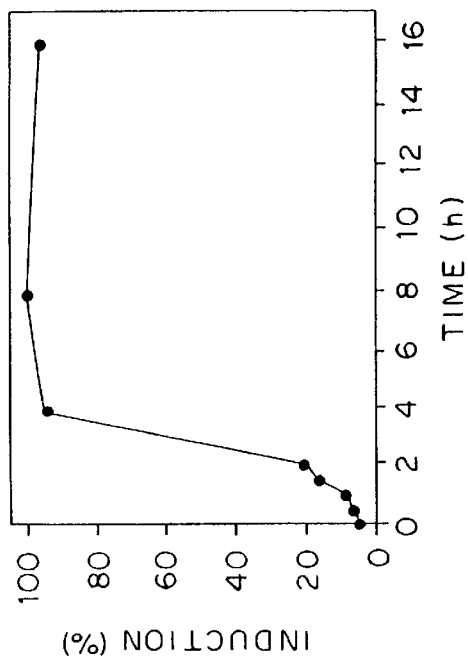
Figure 2E:
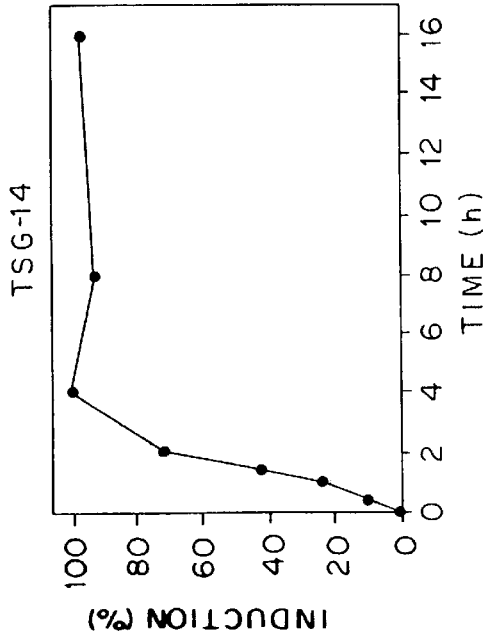
Figure 2G:
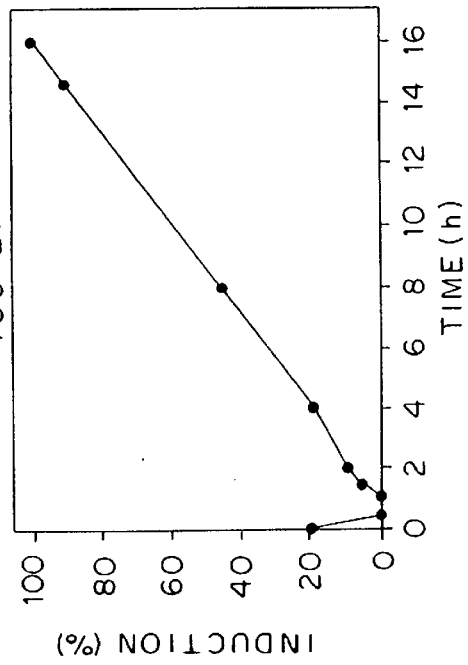
Figure 4:
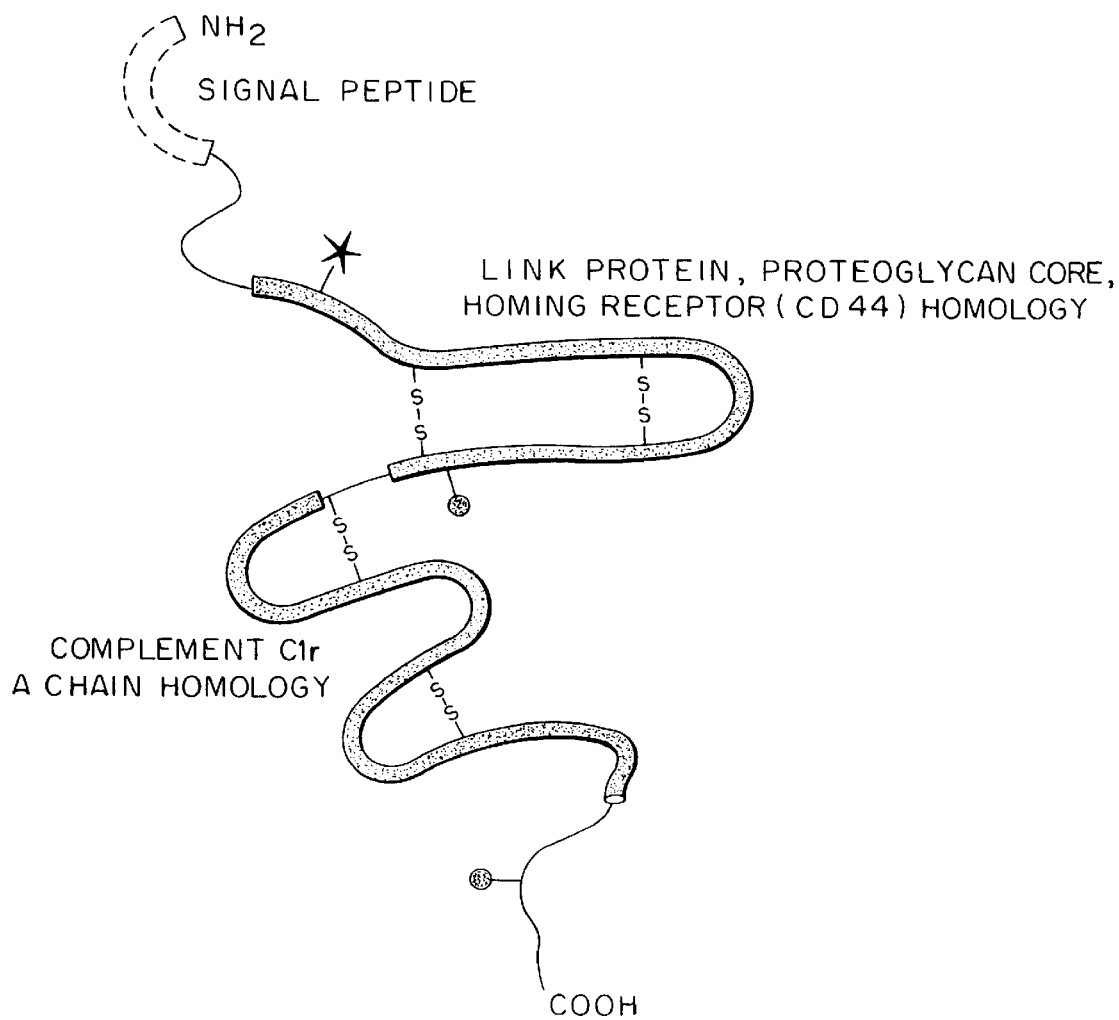
FIG. 4 is a schematic diagram of the putative secondary structure of the TSG-6 protein. The possible signal peptide sequence, and regions with homology to cartilage link protein/proteoglycan core/lymphocyte homing receptor CD44, and to C1r A chain are indicated. Also depicted are two potential N-glycosylation sites (ball and stick) and a chondroitin sulfate linkage site (asterisk and stick).

Complete DNA Sequence of TSG-6 and Homology of the Protein to CD44/Hermes and the Cartilage Link Protein Family Of the three TSG cDNAs having novel partial sequences, TSG-6 was selected for further sequencing. Northern blot analysis showed that the TSG-6 cDNA hybridized to a single TNF-inducible mRNA band with an apparent size of 1.5 kb.

significant length was found. The putative initiation methionine codon is followed by 11 consecutive hydrophobic amino acids followed by a charged region, suggesting a typical cleavable signal peptide (FIGS. 3A–3B and 4). In addition, the predicted TSG-6 protein sequence contains two potential sites of N-linked glycosylation, and one potential chondroitin sulfate linkage site (FIGS. 3A–3B and 4).

Comparison of the deduced amino acid sequence from TSG-6 cDNA with the protein sequences available in databases revealed interesting sequence homologies. FIGS. 5A–5B show that the N-terminal motif of the TSG-6 gene product (between residues 37 and 127) has a high degree of homology with rat cartilage link protein (35.8% identity), rat proteoglycan core protein (38.9% identity) and the recently published sequence (Stamenkovic, I. et al., supra; Goldstein, L. A. et al., supra) of the human lymphocyte homing receptor CD44/gp90 Hermes (32.6% identity). In addition, the C-terminal portion of the TSG-6 gene product shows approximately 30% sequence homology with the α-fragment of the complement component C1r A chain.

The homology between a portion of the predicted sequence of the protein encoded by TSG-6 cDNA and the CD44/Hermes family is of particular interest. The CD44/Hermes membrane proteins have been implicated in the lymph node "homing" of lymphocytes and their binding to a variety of other tissues (Stoolman, L. M., supra). The fact that CD44/Hermes is expressed in many hematopoietic, mesenchymal and epithelial cell lines suggests that this protein functions as a multipurpose adhesion receptor. The striking homology between CD44/Hermes and two repeated domains of cartilage link protein as well as a domain of the proteoglycan core protein has been noted recently (Stamenkovic, I. et al.,supra; Goldstein, L. A. et al., supra). In cartilage link protein and proteoglycan core protein these homologous regions are thought to be involved in the binding of these proteins both to hyaluronic acid and to other proteoglycans through protein—protein interactions. The presence of this epitope in CD44/Hermes may be related to the importance of cellular matrix interactions in lymphocyte traffic.

The highest degree of homology of any TSG-6 region and a known sequence (about 60%) is to the hyaluronic acid binding sites of link protein and proteoglycan core protein. Based on the predicted secondary structure, this region appears to be part of an extended loop formed by disulfide bonds that are highly conserved in all of these proteins (FIGS. 5A–5B). Furthermore, the presence of a potential chondroitin sulfate linkage site suggests that the TSG-6 protein itself may be a so-called "part-time" proteoglycan (Ruoslahti, E., supra), as is also the case with CD44/Hermes.

A secreted form of the TSG-6 protein would be expected to play a role in leukocyte traffic and/or chemotaxis. The TSG-6 protein would be predicted to bind to structures on the surface of leukocytes and alter their adhesion characteristics and/or other function. TSG-6 protein is likely to recognize the same ligand as CD44/Hermes, i.e. hyaluronic acid and, possibly, other structures; in this event, soluble TSG-6 is predicted to interfere with lymphocyte adhesion mediated by the CD44/Hermes molecule. Soluble TSG-6 is also predicted to inhibit cell adhesion to the extracellular matrix.

The TSG-6 protein may also be a cell surface, membrane-associated protein, wherein its expression on the surface of fibroblasts (or other cells) would play a role in leukocyte adhesion. Cell-surface expression of TSG-6 protein would alter the adhesion properties of the cells producing it to extracellular matrix molecules. Thus, TSG-6 expression may be related to the well-documented ability of TNF to either stimulate or inhibit cell growth, and to alter cellular morphology. In this regard, it is interesting to note that TGF-β, another growth-modulatory cytokine, stimulates the synthesis of various proteoglycans (Bassols, A. et al., supra), including decorin (a secreted proteoglycan, a portion of which remains cell surface-associated); this action could be directly related to changes in cell morphology and cell growth characteristics (Ruoslahti, E., supra; Bassols, A. et al., supra). Like decorin, the TSG-6 polypeptide has a molecular weight of approximately 29–30 kDa and a single chondroitin sulfate linkage site. Several membrane proteoglycans (including the murine homologue of CD44/Hermes) are known to interact with the cytoskeleton, providing another potential mechanism whereby increased expression of the TSG-6 protein could lead to changes in cell growth or morphology.

It is therefore apparent that TSG-6 (either secreted or cell-associated) could have profound effects on vital properties of cell including cell growth, cell motility and cell-to-cell interactions. In view of the ability of TSG-6 to bind hyaluronic acid (see below) and the fact that hyaluronic acid is an important component of both cell surfaces and extracellular matrices, soluble TSG-6 would be postulated to inhibit cell adherence. Cell adherence, both to other cells and to the extracellular matrix, is important in the ability of malignant tumor cells to metastasize to distant sites in the body. One useful application of TSG-6, in particular TSG-6 prepared by recombinant DNA technology, is as a prophylactic or therapeutic agent capable of suppressing the metastasis of tumor cells.

The homology between the C-terminal half of the TSG-6 protein and complement component C1r (FIG. 5B), is to a domain of C1r thought to be the $Ca^{2+}$ binding region, responsible for interaction between components C1r and C1s. This suggests that the homologous region of TSG-6 may be a $Ca^{2+}$ binding region and, therefore, perhaps involved in protein-protein interactions.

EXAMPLE VI

Preparation of Bacterial Fusion Proteins

Figure 6A:
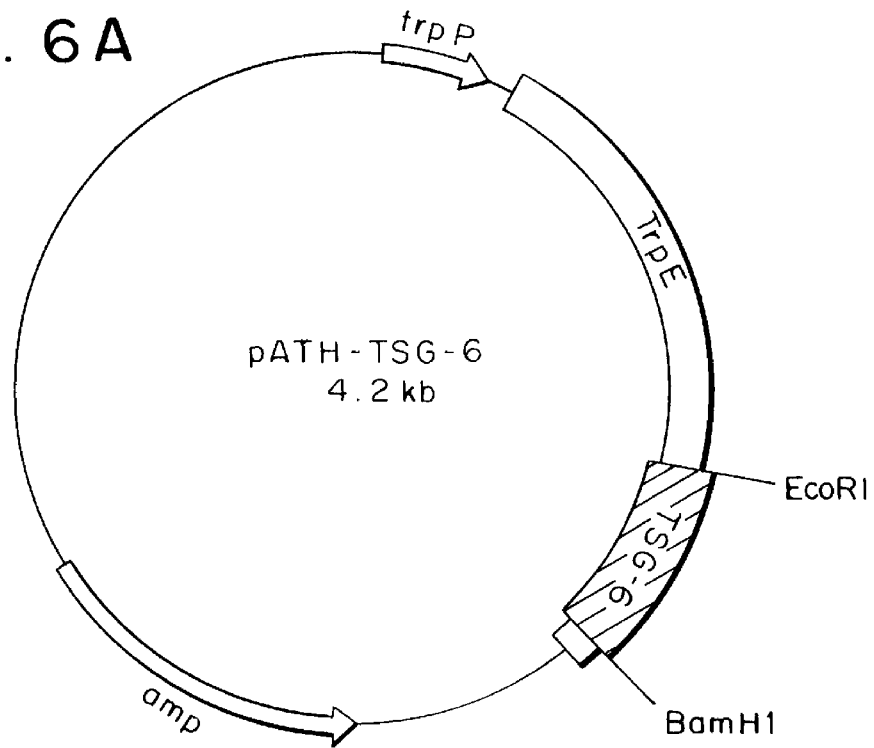
FIGS. 6A and 6B present schematic diagrams of TSG-6 bacterial expression vectors.
Figure 6B:
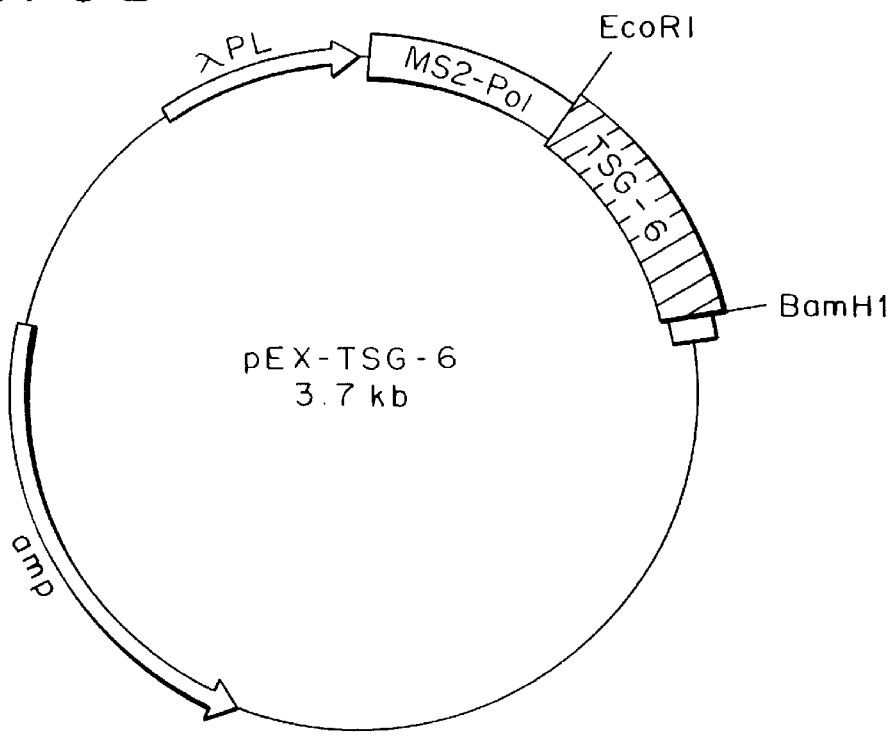

To express a bacterial fusion protein of TSG-6, we used EcoRI cDNA insert from clone lambda6. Clone lambda6 contains a cDNA insert that lacks 402 bp at the 5'-end and 4 bp at the 3'-end of the TSG-6 cDNA sequence shown in FIGS. 3A–3B. An EcoRI-BamH1 (406 bp) restriction fragment (that encodes the portion of TSG-6 open reading frame spanning from Ile115 to Asp248) was isolated from the EcoRI cDNA insert of clone lambda6 and was cloned into the same restriction sites in the polylinker downstream of, and in frame with, a portion (35–37 kDa) of the E. coli TrpE open reading frame in the pATH21 vector (Sprindler, K. R. et al., J. Virol. 49:132–141 (1984)), resulting in the TrpE/TSG-6 expression plasmid, pATH-TSG-6 (FIG. 6A).

The same restriction fragment (EcoRI-BamH1) was also inserted into pEX34A bacterial expression vector, resulting in the MS2/TSG-6 expression plasmid, pEX-TSG-6 (FIG. 6B). pEX34A is a derivative of pEX29 (Klinkert, M. et al., Infec. Immun. 49:329–335 (1985)) which permits the production of foreign proteins fused to the N-terminal part of the MS2 polymerase and controlled by the temperature-inducible PL promoter of bacteriophage lambda.

Figure 7:
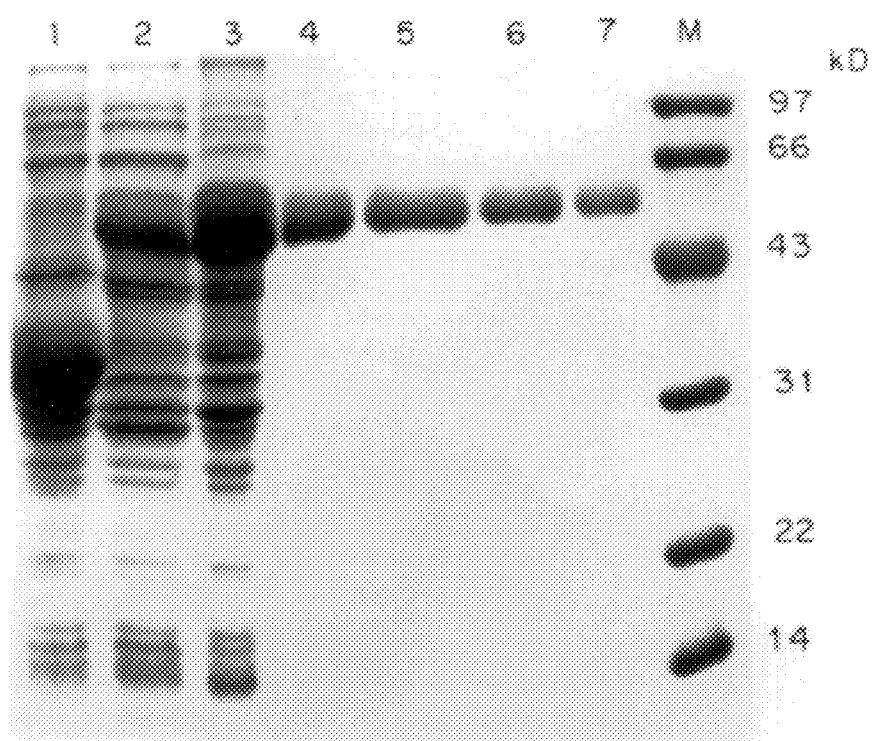
FIG. 7 is a gel pattern showing the expression and purification of TrpE/TSG-6 bacterial fusion protein. E. coli HB101 cells transformed with either pATH-21 or pATH-TSG-6 were induced by 3-β-indole acrylic acid. Total cell lysates were analyzed by SDS-PAGE (10%) and proteins stained with Coomassie blue. Lane 1: total cell extract, after 24 hr induction, of cells transformed with pATH-21; Lanes 2 and 3: total cell extract after 3 hr (lane 2) or 24 hr (lane 3) induction of cells transformed with pPATH-TSG-6. A 7M urea extract of the insoluble proteins of the bacteria shown in lane 3 was fractionated by preparative SDS-PAGE. TrpE/TSG-6 fusion protein was purified by two rounds of electroelution and analyzed by SDS-PAGE (10%). Lane 4: the first eluate (20 μg); Lane 5, 6 and 7: the second eluate (50 μg, 20 μg and 5 μg, respectively); Lane M: marker protein with MW indicated in kDa.

Expression plasmid pATH-TSG-6 was transferred into competent E. coli HB101 cells. Transformed cells in M9 medium containing 2% Casamino acids, 20 µg/ml of L-tryptophan, and 150 µg/ml of ampicillin were grown to a density of $A_{600}$=0.5 (absorbance at 600 nm). To induce synthesis of the fusion protein, cells were pelleted and resuspended in prewarmed L-tryptophan-free medium. After an additional 1-hour incubation, 20 µg/ml of 3-β-indoleacrylic acid was added and the incubation was continued for an additional 24 hours. FIG. 7 shows that protein of the expected size (approx. 54 kDa) was in fact induced following addition of 3-β-indoleacrylic acid.

Figure 8:
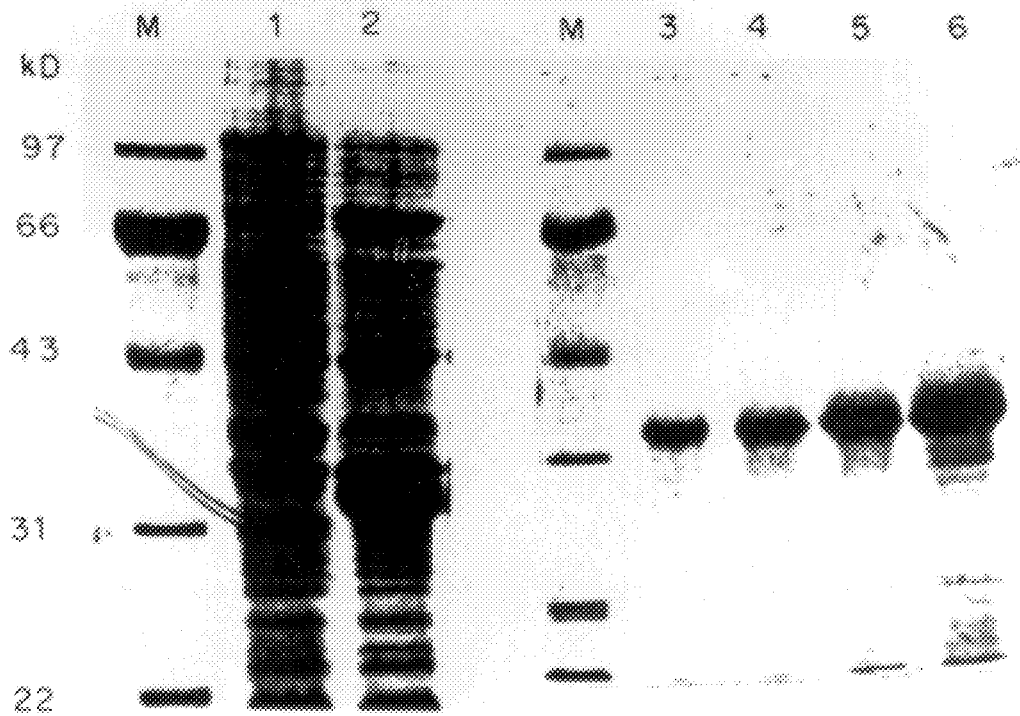
FIG. 8 is a gel pattern showing expression and purification of MS2/TSG-6 bacterial fusion protein. E. coli K12 *H*Trp cells transformed with pEX-TSG-6 were induced by high temperature (42° C.). Total lysates from non-induced (28° C.) and induced (42° C.) cells were analyzed as in FIG. 7. Lane 1: total cell lysate before induction; Lane 2: total cell lysate after induction. Lane 3–6: Electroeluted fusion protein from gel slice of preparative SDS-PAGE (5, 10, 20 and 50 μg, respectively).
Figure 9A:
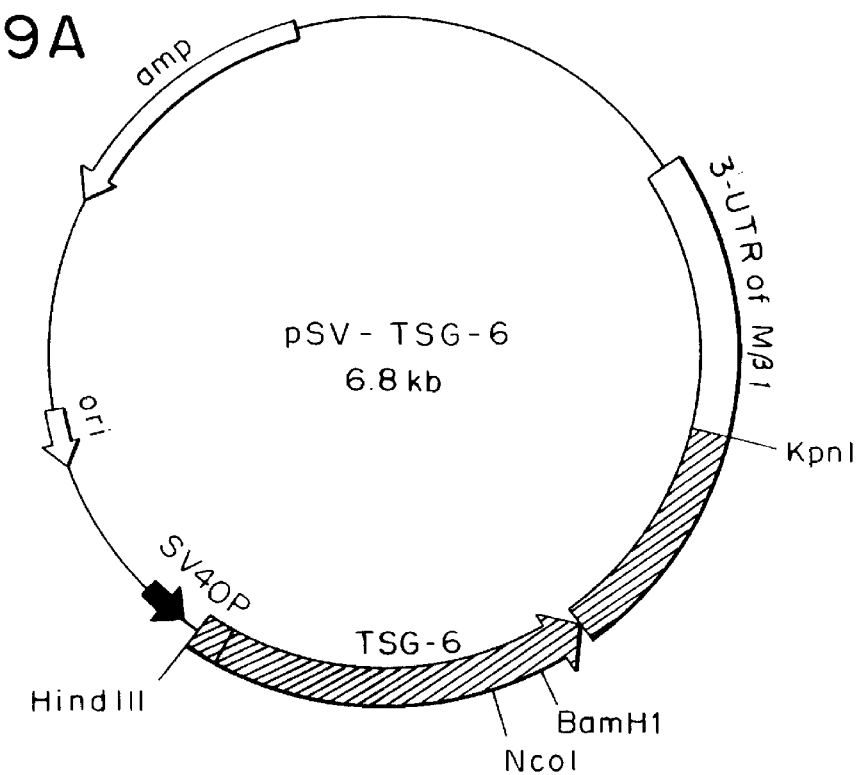
FIGS. 9A and 9B are schematic diagrams of TSG-6 expression vectors pSV-TSG-6 (FIG. 9A) and pMAM-TSG-6 (FIG. 9B).
Figure 9B:
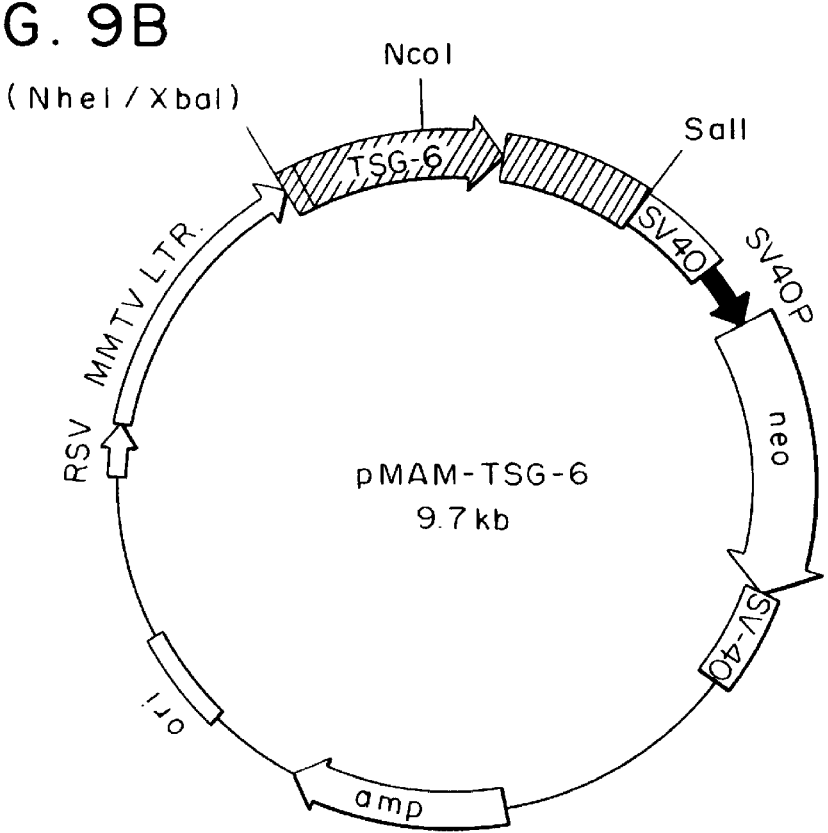

For expression of another TSG-6 fusion protein (MS2/TSG-6), recombinant plasmid pEX-TSG-6 was transferred into competent E. coli K12 *H*Trp (Remaut, E. et al., Gene 15:81–03 (1981)), which contain a temperature-sensitive repressor of the lambdaPL promoter. Cells were grown under selective conditions at 28° C. to high density. To induce synthesis of the MS2/TSG-6 fusion protein, cells were diluted with 4 volumes of prewarmed culture medium (LB) without antibiotics and then incubated for 3 hours at 42° C. under good aeration. FIG. 8 shows that a MS2/TSG-6 fusion protein of the expected size (about 32 kDa) was specifically induced by high temperature.

Purification of both fusion proteins was done essentially as described by Strebel et al. (J. Virol. 57:983–991 (1985)). Cells from a 1L culture were pelleted and washed with TEN (10 mM Tris-HCL, pH 8.0, 1 mM EDTA, 0.5M NaCl), lysed with lysozyme (5 mg/ml) and finally broken by sonication. Insoluble material was recovered by centrifugation (30 min, 20,000×g) and extracted sequentially with 20 ml of 3M urea and 5 ml of 7M urea each for 30 min at 37° C. The 7M urea extract containing the fusion protein was further purified by preparative SDS-PAGE. After electrophoresis the fusion protein was excised from the gel, electroeluted and concentrated as needed. The purity of the electroeluted fusion protein was checked on analytical gels. After the second round of electroelution, highly purified fusion protein was obtained with no detectable E. coli protein bands on SDS-PAGE (lane 7, in FIG. 7).

EXAMPLE VII

Stable Transfection of TSG-6 cDNA into GM637 Cell Lines

The biological functions of TSG-6 can be studied by expression of TSG-6 cDNA in a cell line which does not respond to TNF by the induction of TSG-6 mRNA. For this purpose we examined the inducibility of TSG-6 mRNA by TNF in the SV40 transformed GM637 cells, which do not express TSG-6 mRNA upon treatment with TNF (see FIGS. 10A–10B). As a constitutive expressor, an expresion plasmid, pSV-TSG-6 (FIG. 9A) was constructed by replacing the β-tubulin isotype mβ1 coding region with the full-length TSG-6 cDNA in the plasmid pSVβ1 (Lewis. S. A. et al., Cell 49:539–548 (1987)). In order to exploit suitable restriction enzyme sites for easier cloning, we used the M13mp18 vector carrying the full-length TSG-6 cDNA at the EcoRI site in either the sense or antisense orientation with respect to the lac promoter (Plac). A HindIII-NcoI fragment containing the 5' region of TSG-6 cDNA was isolated from the antisense construct and a NcoI-KpnI fragment containing the 3' region of TSG-6 cDNA was isolated from the sense construct. Both fragments were ligated into the HindIII/KpnI cleaved plasmid pSVβ1.

An inducible expression plasmid pMAM-TSG-6 (FIG. 9B) was also constructed by ligating XbaI-NcoI fragment from the antisense construct and NcoI-SalI fragment from the sense construct into the NheI/SalI cleaved plasmid, pMAMneo (Sardet, C. et al., Cell 56:271 (1989)). Expression vector pMAMneo contains the RSV-LTR enhancer linked to the dexamethasone-inducible MMTV LTR promoter, a construction which yields controllable high level expression of cloned genes in the presence of dexamethasone. It also contains the E. coli neo gene, driven by the SV40 later promoter, for selection of transfectants by growth in medium containing the antibiotic G418.

Both constructs were used to transfect GM-637 cell lines by using $CaPO_4$-DNA precipitation (Graham, F. L., Virology 52:456 (1973)). In the case of stable transfection with pSV-TSG-6, pRSVneo (Gorman, C. et al., Science 221:551 (1983)), which confers resistance to G418, was cotransfected. For stable transfection of $CaPO_4$-DNA precipitates, GM-637 cells were maintained in MEM containing 10% fetal calf serum and gentamycin sulfate at 37° C. and 5% $CO_2$ atmosphere. Cells were split 1:5 with twice a week. To transfect human GM-637 cells, plates were seeded 1 day prior to transfection at $5\times10^5$ cells per 60 mm plate in 5 ml of medium. The TSG-6 expression plasmid, pMAM-TSG-6, or a mixture of pSV-TSG-6 plus pRSVneo, was mixed with 0.25 ml of $CaCl_2$. An equal volume of 2× HBS (pH 7.05) (280 mM NaCl, 10 mM HCl, 1.5 mM $Na_2HPO_4.2H_2O$, 12 mM dextrose, 50 mM HEPES) was added and the solution was incubated for 20 min at room temperature. The $CaPO_4$-DNA suspension was dripped onto plates and mixed. After 5 hr of incubating the cells at 37° C. in a 5% $CO_2$ atmosphere, the transfected cells were given a glycerol shock by treatment with 15% glycerol in 1× HBS for 30 sec. and further incubated for 20 hr. The resulting tolerant cell monolayers were replated in the medium containing G418 (800 μg/ml) to select cells expressing the neomycin resistance marker. Colonies were isolated from transfection plates via the use of cloning rings, subcloned in 24 well plates, and expanded to monolayer culture. Multiple independent transfectants were selected and tested for the expression of TSG-6 cDNA by northern blot analysis.

Figure 10A:
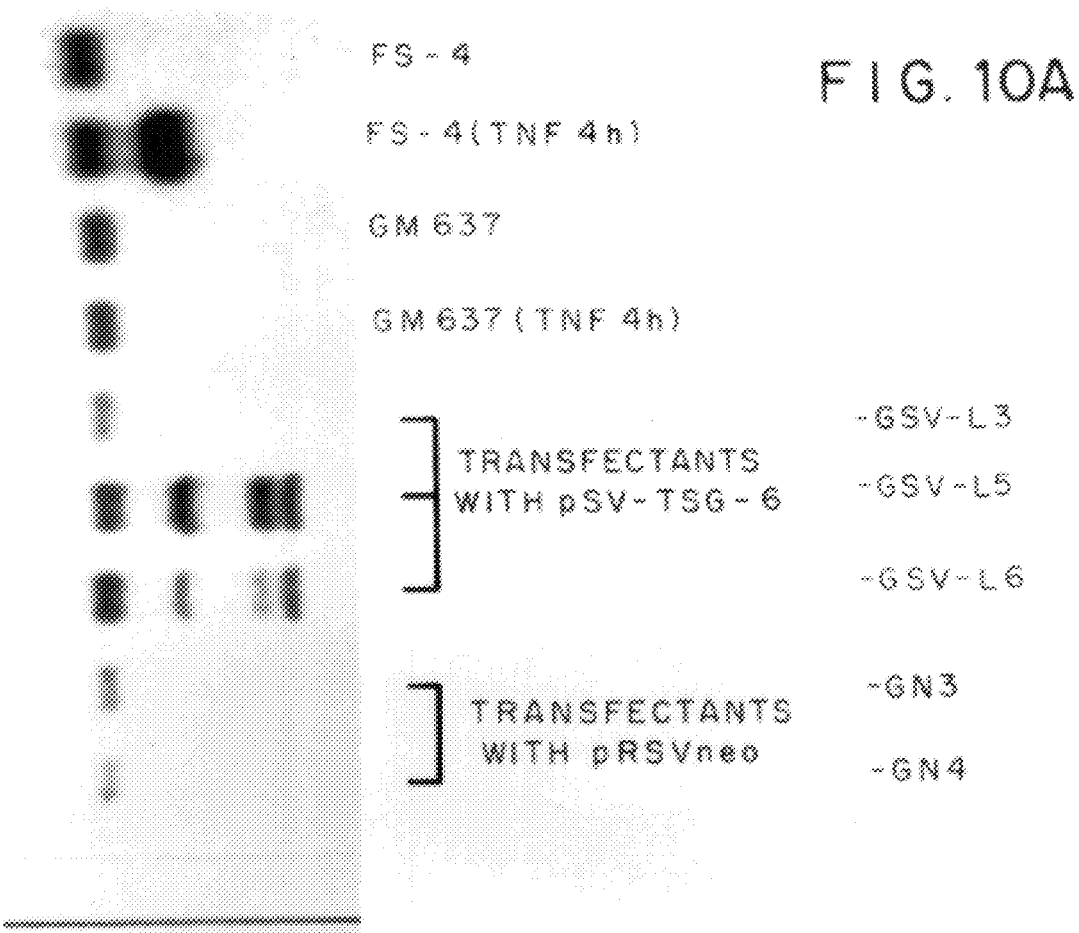
FIGS. 10A–10B show Northern blot analysis of the expression of TSG-6 mRNA in various stable transfectants.
Figure 10B:
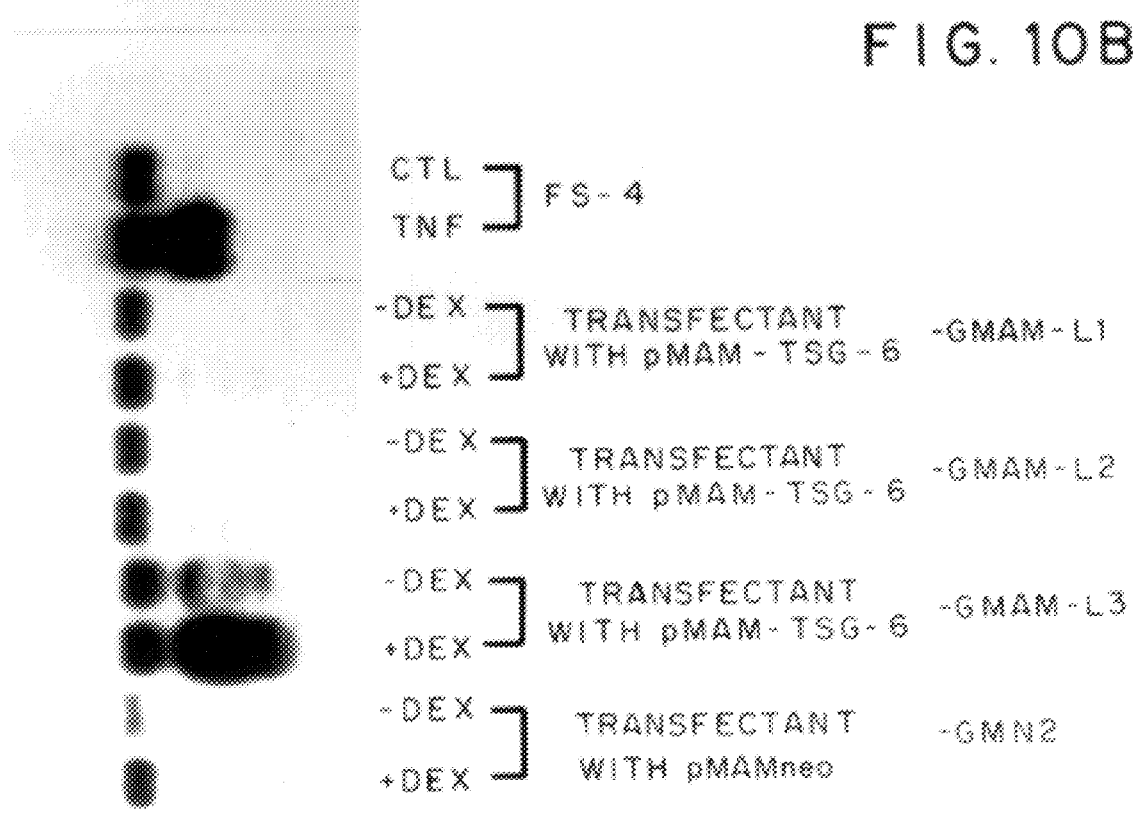

FIGS. 10A–10B show that several transfectants express TSG-6 mRNA in the absence of TNF. The major band appears to be the same size as the band corresponding to TSG-6 mRNA induced by TNF in FS-4 cells. The upper bands may be the result of incomplete processing of TSG-6 cDNA in the polyadenylation signal. The expression of TSG-6 protein in these transfectants was confirmed by Western blot analysis with the aid of polyclonal antiserum generated against the TSG-6 bacterial fusion protein (see below).

EXAMPLE VIII

Expression of TSG-6 mRNA by TNF: Specificity for Normal Connective Tissue

Figure 11A:
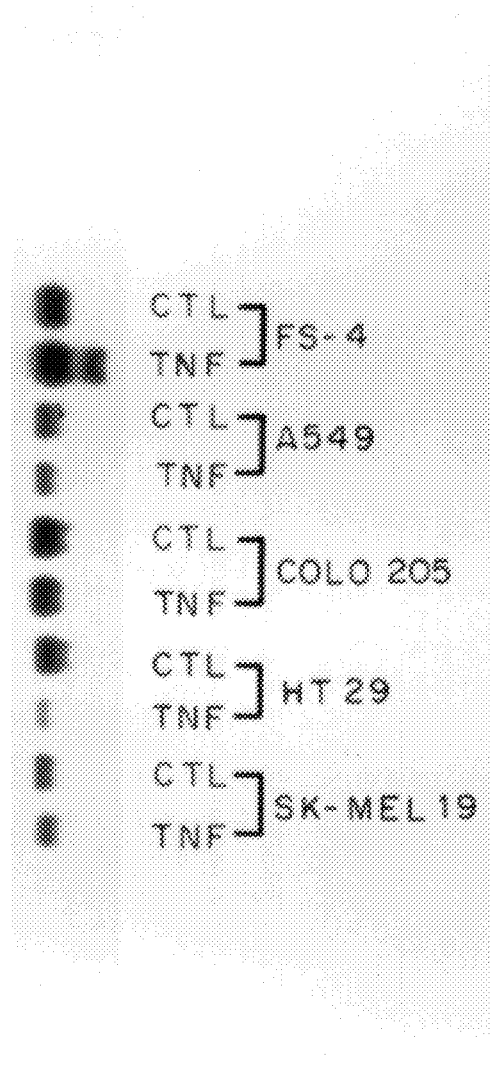
FIGS. 11A–11B show Northern blot analysis of TNF induction of TSG-6 mRNA in various cell lines. TNF (20 ng/ml) was added to confluent cells. After 4 hr, total RNA was extracted and subjected to Northern blot analysis. "CTL" (control) indicates no TNF treatment; "TNF" indicates 4-hour TNF treatment. The following cells were examined.
Figure 11B:
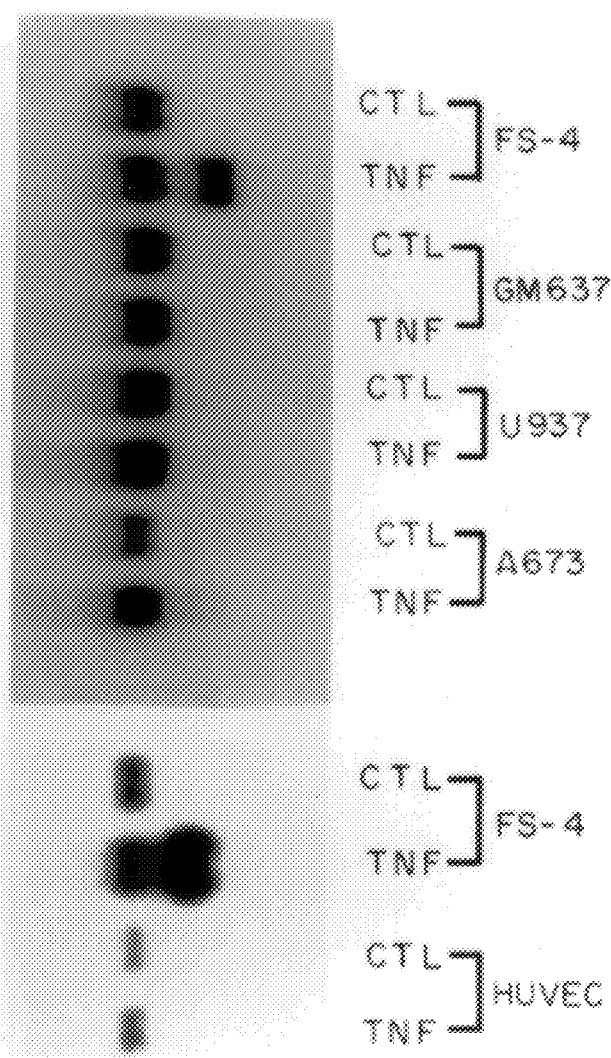

The inducibility of TSG-6 mRNA by TNF was examined in various cell lines by Northern blot analysis. The presence of detectable TSG-6 mRNA was of interest in view of the homology of TSG-6 protein to the homing receptor, CD44. Human umbilical vein endothelial cells (HUVEC), which are one cell type shown to be highly responsive to TNF and useful in the analysis of proinflammatory action of TNF, were examined. Also examined were GM-637 cells, a line of SV40 virus-transformed human diploid fibroblasts. FIG. 11 shows that these cell types do not express TSG-6 mRNA upon TNF stimulation. Other selected cell lines (U937, A673, Colo205, HT29 and SK-MEL-19) also did not produce TSG-6 mRNA after TNF treatment. This unresponsiveness is not due to a lack of TNF receptors on the cell surface because these cell lines have been shown to be responsive to the actions of TNF (Le, J. et al., 1987, supra). These findings indicate the possibility that the expression of TSG-6 mRNA is restricted to cells of normal connective tissue origin To test this notion, the inducibility of TSG-6 mRNA in other normal fibroblasts (FS-48, FS-49 and WI-38) and in fibroblast cell lines transformed with either SV40 virus (WI-38 VA13, GM-637) or SV40 large T antigen only (FS-4-SV1, FS-4-SV2 and FS-4-SV3) was examined. TSG-6 mRNA was indeed induced in all normal fibroblasts but not in SV40 virus-transformed fibroblasts (WI-38 VA13 or GM-637). Interestingly, TNF induction of TSG-6 mRNA was significantly decreased in FS-4 cells transfected with SV40 large T antigen (FIG. 12). This was not due to the general decrease in TNF responsiveness of these transfectants; for example, TSG-14 mRNA, encoded by another TNF-stimulated gene (see above) is more highly induced in large T antigen transfectants than in FS-4 cells after TNF treatment. It is concluded that the degree of "oncogenic" transformation has a controlling effect on the inducibility of TSG-6 mRNA.

EXAMPLE IX

Preparation of Polyclonal Antiserum and Purification of Anti-TSG-6 Antibodies by Immunoaffinity Chromatography Rabbits were first immunized with about 200 µg of the TrpE/TSG-6 fusion protein suspended in Freund's complete adjuvant and were boosted at intervals of 2–3 weeks with the same amount of protein in Freund's incomplete adjuvant. All injections were performed subcutaneously, except for the final boost which was done intravenously. Rabbits were bled six days after immunizations. Sera were analyzed by immunoblotting according to Strebel et al. (supra).

Antibodies raised against the TrpE/TSG-6 fusion protein show nonspecific binding to a broad range of proteins from supernatants or extracts of FS-4 cells and other human cells. To obtain antibodies specific for TSG-6 domains of the fusion protein, the antiserum was subjected to purification on an immunoaffinity matrix to which the MS2/TSG-6 fusion protein was coupled.

The immunoaffinity chromatography matrix was prepared as follows. Five mg of purified MS2/TSG-6 fusion protein was dialyzed extensively against 0.5M NaCl. Three ml of EAH-Sepharose 4B (Pharmacia) was washed extensively with 0.5M NaCl and the purified MS2/TSG-6 fusion protein was added. The pH was adjusted to 4.5 and 40 mg 1-(3-dimethylaminopropyl)-3-ethylcarbodiimide hydrochloride (Aldrich Chemical Co.) dissolved in 1 ml distilled water was added dropwise while constantly stirring. Thereafter, the pH was readjusted to 4.5 and the coupling reaction was allowed to proceed overnight under constant stirring. Acetic acid (200 µl) was added for another 4 hr to block the remaining amino groups on the matrix. Finally, the matrix material was washed several times alternately with 0.1M acetate buffer, pH 4.0, 0.5M NaCl, and 0.1M sodium bicarbonate buffer, pH 8.3, 0.5M NaCl, and suspended in Tris-buffered saline for storage.

For immunoaffinity chromatography, 0.5 ml of MS2/TSG-6 Sepharose was equilibrated with Tris-buffered saline (20 mM Tris, 0.5M NaCl, pH 7.5) containing 0.05% Tween-20 (TTBS). One ml of antiserum raised against the TrpE/TSG-6 fusion protein was mixed with 0.5 ml MS2/TSG-6 Sepharose and 0.5 ml TTBS, and the mixture incubated in a cryotube at 4° C. overnight under constant rotation. The suspended solid phase matrix material was transferred to a centrifuge tube and washed with 10 ml TTBS. Thereafter, the sediment was transferred to an Eppendorf tube, centrifuged (14,000 rpm, 2 min.) and the supernatant carefully removed. One ml 0.1M glycine-HCl buffer, pH 2.5, was added and the gel was vigorously shaken for 2 min. After further centrifugation, the supernatant was immediately neutralized with solid Tris.

EXAMPLE X

Detection of Natural and Recombinant TSG-6 Protein from TNF-Treated FS-4 Cells and GM-637 Cells Transfected with a TSG-6 Expression Vector The predicted TSG-6 protein sequence features a putative initiation methionine, followed by eleven hydrophobic amino acids and a charged region. This portion has the characteristics of a cleavable signal peptide. There are proteins that are known to exist in both secreted and membrane-anchored form (either integral or phosphatidylinositol-linked) (Mosley, B. et al., Cell 59:335 (1989); Camerini, D. et al., Nature 342:78 (1989)). Thus, the TSG-6 protein may also be anchored to the cell surface via glycosyl-phosphatidylinositol structures because of the hydrophobic amino acid stretches in its C-terminal portion which could interact with the cell membrane. To distinguish between these possibilities, experiments were conducted to localize TSG-6 protein in the supernatants or extracts of either (a) FS-4 cells treated with TNF for 7–24 hours, or (b) GM-637 cells transfected with TSG-6 cDNA (termed GSV-L5).

After FS-4 cells had been grown to confluence in MEM containing 5% FCS, the medium was exchanged for MEM containing 0.25% FCS and the cells maintained in this medium for three days. Thereafter, the medium was removed and the FS-4 cells received MEM containing 0.25% FCS with or without 20 ng/ml TNF-α. After 5 h the medium was exchanged for serum-free MEM containing nonessential amino acids. (TNF-treated cultures again received 20 ng/ml TNF-α). GSV-L5 cells were grown to confluence in MEM containing 10% FCS and 800 µg/ml G418. Thereafter, the medium was replaced with serum-free MEM containing nonessential amino acids. Both FS-4 and GSV-L5 cells were cultured for a total of 7 to 24 hours, after which culture supernatants and cell pellets were collected and processed. Cell culture supernatants were collected, cleared by centrifugation, and concentrated about 100-fold in an Amicon apparatus. Cell pellets were washed with serum-free medium and lysed in SDS-PAGE sample buffer.

For Western blot analysis of samples 12.5% polyacrylamide gels were used in a Mini-Protean II Electrophoresis cell (Bio-Rad). The electrophoretic transfer was carried out at 100V for 1 hr using nitrocellulose as transfer medium (Trans-Blot Transfer Medium, Bio-Rad). After blocking with 1% "blotto" in Tris buffered saline, affinity-purified rabbit anti-TSG-6 antiserum was used as the first antibody, a biotinylated goat anti-rabbit immunoglobulin was used as the second antibody, and an avidin-biotinylated alkaline phosphatase complex (Vectastain, Vector Labs.) was used as the detection system.

The immunopurified antibody, specific for TSG-6 domains of the TrpE/TSG-6 fusion protein, detected one or more bands in concentrated supernatants of TNF-treated FS-4 cells or GSV-L5 cells, but not in supernatants from control cells (FIG. 13A). These bands were not detected by an immunopurified pre-immune serum from the same rabbit (FIG. 13B). No bands could be detected by the immunopurified antibody in lysates of GSV-L5 cells (FIG. 14) or lysates of FS-4 cells. The major band detected in serum-free culture supernatants of TNF-treated FS-4 cells and GSV-L5 cells (FIG. 13A) corresponds to a molecular weight of 36 to 41 kDa and is thought to represent a glycosylated monomer of the TSG-6 protein. Bands corresponding to a molecular weight of greater than 110 kDa were sometimes found in serum-free culture supernatants of GSV-L5 cells (FIG. 13A) and FS-4 cells, probably representing an oligomeric or glycosaminoglycan-linked form of the TSG-6 protein. Another band, corresponding to a molecular weight of approximately 32 kD and probably representing the nonglycosylated or partially glycosylated TSG-6 monomer, could be found in affinity-purified TSG-6 preparations from serum-containing GSV-L5 cultures (FIG. 16) and sometimes in concentrated supernatants of serum-free GSV-L5 cultures (FIG. 15).

EXAMPLE XI

Binding of TSG-6 Protein to Hyaluronic Acid

To analyze the hyaluronic acid binding properties of the TSG-6 protein, hyaluronic acid was coupled to Sepharose (HA-Sepharose) to be used as a matrix for affinity chromatography.

It is known that the binding of the cartilage proteoglycan core protein and link protein to hyaluronic acid, though highly specific, is maintained at least partially by ionic interactions. Basic amino acid residues in the highly conserved hyaluronic acid binding domain of the proteoglycan core protein (Hardingham et al., *Biochem. J.* 157:127 (1976)) and in the link protein (Lyon, M., *Biochim. Biophys. Acta* 881:22 (1986)) are essential for this interaction. Modification of the uronic acid residues in hyaluronic acid also interferes with the protein-hyaluronic acid interaction (Christner, J. et al., *Biochem. J.* 167:711 (1977)). High salt concentrations prevent the binding of link protein to hyaluronic acid and dissolve link protein-hyaluronic acid complexes (Goetinck, P. F. et al., *J. Cell Biol.* 105:2403 (1987); Tengblad, A., *Biochem. J.* 199:297 (1981)).

Because the TSG-6 protein shows considerable homology to the hyaluronic acid binding domains of proteoglycan core protein, high salt concentrations were used for elution in experiments designed to show binding of TSG-6 protein to HA-Sepharose.

To couple hyaluronic acid to Sepharose, 100 mg hyaluronic acid from bovine trachea (Sigma Chemicals) was dialyzed extensively against 0.5M NaCl. Five ml EAH-Sepharose 4B (Pharmacia) was washed extensively with 0.5M NaCl and mixed with the hyaluronic acid solution. The pH was adjusted to 4.5 and 40 mg 1-(3-dimethylaminopropyl)-3-ethylcarbodiimide hydrochloride (Aldrich Chem. Co.), dissolved in 1 ml distilled water, was added dropwise under constant stirring. The pH was kept at 4.5 for 1 hr. After constantly stirring the reaction mixture overnight, 200 µl acetic acid were added for another 4 hr to block the remaining amino groups on the EAH-Sepharose. Finally, the matrix material was washed several times, alternating between 0.1M acetate buffer (pH 4.0, containing 0.5M NaCl) and 0.1M Tris-HCl buffer (pH 9.5, containing 0.5M NaCl), and was resuspended in phosphate buffered saline. Control Sepharose was prepared in the same way but without hyaluronic acid.

To show the binding of TSG-6 protein to HA-Sepharose but not to a similarly activated and blocked control Sepharose matrix, concentrated serum-free supernatant of GSV-L5 cells was used. HA-Sepharose or control Sepharose (200 µl each) was incubated with 500 µl concentrated supernatant of GSV-L5 cells and 500 µl phosphate buffered saline (PBS) overnight at 4° C. under constant rotation. Thereafter, the supernatants were removed and analyzed by Western blotting with anti-TSG-6 antibody. The Sepharose was washed with 10 ml PBS and 10 ml PBS containing 0.05% Tween-20. Thereafter, the HA-Sepharose as well as the control Sepharose were eluted with 1 ml 20 mM Tris-HCl, pH 8.5, containing 3M NaCl. The procedure was carried out in Eppendorf tubes. After vigorous shaking and centrifugation the supernatants were removed, dialyzed against Tris buffered saline and analyzed by Western blotting (FIG. 15). Whereas the control Sepharose matrix did not bind any detectable TSG-6 protein, the HA-Sepharose bound virtually all the TSG-6 protein present in the concentrated GSV-LS culture supernatant. The band showing a molecular weight of about 29 or 32 kDa, detectable in supernatants from GSV-L5 cells after prolonged cultivation (20–24 hr) in serum-free medium, probably represents a nonglycosylated or partially glycosylated TSG-6 monomer.

When supernatants from GSV-L5 cultures in serum-containing medium (10% FCS) were used for the affinity chromatography on HA-Sepharose, three distinct bands could be detected in Western blots (FIG. 16). One band corresponding to a molecular weight of about 29 or 32 kDa probably represented a nonglycosylated or partially glycosylated TSG-6 monomer. The main band corresponding to a molecular weight of 36 or 38 to 41 kDa probably represented an N-glycosylated monomer. A third (and more diffuse) band corresponding to a molecular weight of greater than 110 kDa was thought to represent a TSG-6 oligomer or a glycosaminoglycan-linked form of the TSG-6 protein.

EXAMPLE XII

TSG-6 Protein and Leukocyte Adhesion

Based on homology with CD44/Hermes, an important lymphocyte homing receptor, TSG-6 is expected to play a role in leukocyte adhesion. This was tested by treating FS-4 cells with TNF and showing that this led to a marked increase in the adherence of human "PHA blasts" (peripheral blood T cells cultured in the presence of phytohemagglutinin (PHA) and IL-2). TNF increases lymphocyte adhesion to endothelial cells, mediated at least in part by the up-regulation of the adhesion molecule, ICAM-1 (Dustin, M. L. et al., *J. Immunol.* 137: 245 (1986)). TNF also up-regulates the neutrophil adhesion molecule, ELAM-1, in HUVEC (Bevilacqua, M. P. et al., *Proc. Natl. Acad. Sci. USA* 84: 9238 (1987); *Science* 243:1160 (1989)).

Quantitation of lymphocyte (e.g., PHA blast) and neutrophil adherence is performed essentially according to published methods (Dustin et al., supra; Bevilacqua et al., supra).

Antibodies specific for the TSG-6 protein, as described herein, are examined for their ability to inhibit the increase in the adherence of PHA blasts to TNF-treated FS-4 cells. Treatment of FS-4 cells with rabbit anti TSG-6 antibodies, and in particular, polyclonal antibodies and mAb which are specific for a TSG-6 epitope which is homologous to CD44/Hermes, at the time of TNF induction, are found to reduce T cell adhesion.

Specificity of this interaction is shown using mabs specific for CD44/Hermes (such as those produced by Dr. Eugene Butcher (Stanford University) which do not bind to TSG-6 (Jalkanen, S. et al.,*J. Cell Biol.* 105:983 (1987)). The anti-CD44/Hermes antibodies do not block the above adhesion reaction, indicating that it is due to TSG-6 and not CD44/Hermes expression in TNF-treated FS-4 cells.

The role of ICAM-1 in the adherence of TNF-treated FS-4 cells, via the induction of TSG-6, is analyzed using mabs to ICAM-1 and/or to its ligand LFA-1 (Dustin et al., supra). Antibodies to ICAM-1 and LFA-1 are found to reduce PHA blast adherence to TNF-treated FS-4 cells at the level of the T cells. Antibodies to TSG-6, and peptides of TSG-6 corresponding to the portion homologous to CD44) are also found to inhibit PHA blast adhesion to TNF-treated FS-4 cells, at the level of the FS-4 cell.

The importance of TSG-6 in neutrophil adhesion to FS-4 cells and the role of ELAM-1 (Bevilacqua et al., supra) is evaluated using anti-TSG-6 antibodies, as above, and mAbs specific for ELAM-1. It is shown that both types of antibodies inhibit neutrophil adherence to TNF-treated FS-4 cells, indicating an interaction between ELAM-1 on neutrophils and TSG-6 (or a TSG-6-dependent process) in fibroblasts.

EXAMPLE XIII

Inhibition of TNF-induced, TGF-6-mediated Release of Proteoglycan from Cartilage Explants by Anti-TSG-6 Antibodies Pieces of articular cartilage (approximately 4 mg wet weight) obtained from patients undergoing surgery or biopsy are maintained for 48 h at 37° C. in DMEM containing 10% FCS. Each piece is then transferred to a well of a 96-well plate and incubated in 0.2 ml of culture medium, either with no addition, with human TNF, or with human TNF and an anti-TSG-6 antibody. The medium is changed at about 3 days and the culture is terminated after about 6 days. The cartilage explant is removed from the medium and digested completely with papain. The chondroitin sulfate content of this digest and of the culture medium is estimated by use of the metachromatic dye, dimethylmethylene blue (Oldberg, A. et al., *J. Biol. Chem.* 256: 10847 (1981)). TNF is found to induce release of proteoglycan from cartilage and antibodies to TSG-6 inhibit this breakdown, indicating that TSG-6 is a mediator of TNF-induced proteoglycan release.

EXAMPLE IX

Experimental Procedures

Materials. Chondroitin sulfate ABC lyase from *Proteus vulgaris* (EC 4.2.2.4) and hyaluronate lyase from *Streptomyces hyalurolyticus* (EC 4.2.2.1) were purchased from Sigma, rabbit anti-human inter-α-inhibitor (IαI) immunoglobulin was from Dako (Glostrup, Denmark), and [$^{35}$S] methionine/[$^{35}$S]cysteine (Trans 35S-label) was purchased from ICN. Immmunoprecipitin (heat-killed, formalin fixed *Staphylococcus aureas*, SAC) was from GIBCO BRL, and EX-CELL 300 and EX-CELL 400 medium was from JRH Biosciences (Lenexa, Kans.). Albumin Removal AFFINI-FILTERS were from Affinity Technology, New Brunswick, N.J., Centricon-10 concentrators were from Amicon, and polyvinylidene difluoride (PVDF) membranes (Immobilon-P) were from Millipore. FPLC equipment and separation matrices were from Pharmacia. All other chemicals were purchased from commercial suppliers and were of analytical or molecular biology grade.

Production and Purification of Recombinant Human TSG-6 Protein. Recombinant *Autographa californica* nuclear polyhedrosis virus (genus Baculovirus) containing human TSG-6 cDNA (Wisniewski et al., *Physiology and Pathophysiology of Cytokines* (1992)) was used for the infection of High Five insect cells from *Trichoplusia ni* (BTI-TN-5B1-4; purchased from Invitrogen, San Diego, Calif.). For high-level expression and purification of TSG-6 protein, TN-5B insect cells were grown in serum-free EX-CELL 400 medium. The cell culture medium was replaced 24 hrs. after inoculation of ~70–80% confluent cultures with recombinant virus and collected again 48 hrs. later. For purification of TSG-6 protein, cleared culture supernatant was directly loaded on a MonoS (HRS/5) column equilibrated with 20 mM 4-morpholineethanesulfonic acid (MES), pH 6.5. Bound protein was eluted with a linear gradient (20 mL) from 0 to 1M NaCl in 20 mM MES, ph 6.5. Fractions containing the bulk of TSG-6 protein (0.45–0.65M NaCl) were pooled, concentrated in Centricon-10 units, and applied onto a Supperdex 75 (HR 10/30) column equilibrated with 20 mM MES, pH 6.5, 0.5 M NaCL. This resulted in the recovery of ≧95% pure TSG-6 protein as judged by silver staining of SDS-PAGE gels. About 1 μg of pure protein was recovered per 1 mL of culture supernatant.

Microsequencing of the purified TSG-6 ;protein established Trp[18] as the N-terminus of the mature secreted glycoprotein (Table 2), which is in good agreement with the predicted cleavage site of the signal peptide sequence (Von Heijne, *J. Mol. Biol.* 173, 243–251 (1984); *J. Mol. Biol.* 184, 99–105 (1985)).

Analysis of TSG-6 Binding to Carrier Protein. To determine the presence of TSG-6 binding protein, samples to be analyzed were mixed with an equal volume of TSG-6-containing serum-free supernatants of TN-5B insect cells infected with recombinant Baculovirus and incubated at 37° C. for 30–60 min. (Purified TSG-6 protein was used in some experiments, as indicated.) Thereafter, the mixtures were analyzed for the presence of the 120-kDa complex by Western blotting with purified rabbit antibody to TSG-6 as described earlier (Wisniewski et al., *J. Immunol.* 151, 6593–6601 (1993)). For detection of inter-α-inhibitor (IαI) epitopes by Western blotting,, membranes were incubated with a rabbit anti-human IαI antibody (Dako) at a 1:2000 dilution for 1 hr.

Immunoprecipitation. Human HepG2 hepatoma cells producing IαI constitutively (Bourguignon et al., *Biochem. J.* 261, 305–308 (1989)) were grown in serum-free EX-CELL medium. [$^{35}$S]Methionine(Trans$^{35}$S-label) was added to about 75% confluent HepG2 cell cultures in a 25 cm$^2$ flask (500 μCi/culture), and the culture supernatant was collected after 24 hrs. The $^{35}$S-labeled HepG2 culture supernatant (300 μL) was incubated with 16 μg of purified recombinant TSG-6 protein or with buffer for 1 hr. at 37° C. Samples were precleared with 150 μL of 10% SAC. Rabbit anti-TSG-6 antiserum or preimmune serum from the same rabbit (5 μL) was added to the supernatants and incubated for 3 hrs. at 37° C. Thereafter, 150 μL of 10% SAC was added and incubated for 30 min. at room temperature. The supernatants were removed, and the pellets were washed 3 times with 1 mL of 20 mM tris, pH 7.5, 0.5M NaCl, and 0.02% Tween-20. Pellets were resuspended in 40 μL of SDS-PAGE sampler buffer (reducing) and incubated for 3 min. in a boiling water bath. The supernatants were removed and analyzed by SDS-PAGE on 10% polyacrylamide (PAA) gels and fluorography.

Partial Purification of TSG-6 Binding Protein from Human Serum for N-Terminal Microsequencing. Protein precipitated between 40% and 55% saturation with ammonium sulfate from 40 mL of fresh human serum was dissolved in 10 mL of PBS an dialyzed against 50 mM KH$_2$PO$_4$, pH 7.0, 50 mM NaCl. Four aliquots were passed through Affini-filter cartridges for albumin removal (Affinity Technology). Each cartridge was washed with 5 mL of the same buffer and eluted with 5 mL of 5 mM KH$_2$PO$_4$, pH 7.0, 0.5M NaCl. The eluates of four cartridges were pooled, dialyzed against 20 mM Tris, pH 7.5, 50 mM NaCl, and loaded on a MonoQ column (HR5/5, Pharmacia) using a Pharmacia FPLC system. Protein was eluted with a linear gradient (16 mL) from 50 mM to 1M NaCl in 50 mM Tris, pH 7.5. Fractions containing TSG-6 binding activity were pooled and concentrated in Centricon-10 units to a final volume of 200 μL. This material was further separated by FPLC on a Superdex 200 column (HR 10/30). The column was equilibrated with 50 mM Na$_2$HPO$_4$, ph 7.0, 150 mM NaCl and run at a flow rate of 0.5 mL/min. Fractions containing TSG-6 binding activity were pooled and concentrated in Centricon-10 units. the material was further separated by SDS-PAGE under reducing conditions on a 4–15% PAA gel and transferred in methanol-free transfer buffer at 200 mA for 1 hr. to a PVDF membrane. Staining with Coomassie Blue R250 revealed only one protein band greater than 200 kDa which was used for microsequencing.

Purification of IαI from Human Serum. IαI purified from human serum, according to Salier et al., *Anal. Biochem.* 109, 273–283 (1980), with some modifications. FPLC on Q Sepharose Fast Flow was used instead of DEAE-Sephacel chromatography. Chelating Sepharose Fast Flow was used for zinc chelate chromatography. Phenyl Superose was used for hydrophobic chromatography and Superdex 200 was used for size-exclusion chromatography instead of Sephacryl-300. The IαI recovered was essentially pure as judged by SDS-PAGE and silver staining.

Protein Sequencing. Coomassie Blue-stained protein bands on the PVDF membranes were cut from the blots and placed directly into a micro-cartridge of an Applied Biosystems Model 473A protein sequencer. Automated Edman degradations were performed using standard cycles with gas phase delivery of trifluroacetic acid (TFA). Data collection and reduction were performed using Applied Biosystems Model 610 software.

Microsequencing of the TSG-6/IαI Complex. Purified recombinant TSG-6 (2.5 μg) was incubated with 2.6 μg of IαI purified from human serum for 1 hr. at 37° C. After SDS-PAGE in an 8% PAA gel under reducing conditions, protein was transferred to a PVDF membrane in methanol-free transfer buffer at 200 mA for 1 hr. The membrane was stained with Coomassie Blue R250, and the newly formed 120-kDa band (not present in the IαI or TSG-6 preparation) was excised for microsequencing.

RESULTS

Binding of TSG-6 Protein to a Protein Present in Mammalian Sera and in Supernatants of Human HepG2 Hepatoma Cells. Western blot analysis of serum-free culture supernatants of TN-5B insect cells infected with recombinant Baculovirus encoding human TSG-6 revealed the presence of a 32-kDa band reactive with antibody to TSG-6 (FIG. 18, lane 1). Recombinant human TSG-6 protein produced in insect cells migrates somewhat faster than the 35-kDa TSG-6 protein from human cells (Wisniewski et al., *J. Immunol.* 151, 6593–6601 (1993)) possibly due to a different extent of glycosylation. A second band recognized by antibody against TSG-6, with the apparent molecular mass of 29 kDa, probably represents unglycosylated TSG-6 protein. When TSG-6 containing culture supernatants were incubated at 37° C. in the presence of fetal bovine serum (lane 3), mouse serum (lane 7), or serum-free culture supernatant of human HepG2 hepatoma cells (lane 5), an additional 120-kDa band became readily apparent. A band of identical electrophoretic mobility appeared after incubation of recombinant TSG-6 protein with human or rabbit serum.

The 120-kDa Band Represents a Complex of TSG-6 with a Distinct Protein. In order to show that the newly formed 120-kDa band revealed by Western blot analysis is indeed a complex of TSG-6 with a distinct protein, and not a TSG-6 oligomer whose formation is promoted by serum, we employed immunoprecipitation. When a supernatant from HepG2 cells cultured in serum-free medium in the presence of [$^{35}$S]-methionine was incubated with unlabeled purified recombinant TSG-6 protein and immunoprecipitated with a rabbit anti-serum to TSG-6, a labeled 120-kDa molecule was precipitated (FIG. 19). This immunoprecipitation was specific because incubation with preimmune serum from the same rabbit or incubation of $^{35}$S-labeled HepG2 supernatants with immune serum in the absence of TSG-6 protein failed to precipitate a labeled 120-kDa molecule. [$^{35}$S] Methionine incorporation into a molecule specifically recognized by an antibody to TSG-6 indicates that the 120-kDa molecule is indeed a complex of TSG-6 protein with another distinct protein that is constitutively produced and secreted by human HepG2 cells.

Partial Purification and Identification of the TSG-6 Binding Protein from Human Serum. Fractionation of normal human serum by ammonium sulfate precipitation showed that proteins precipitated between 40% and 55% saturation contained most of the TSG-6 binding activity, although significant binding was also detected in the fraction precipitated at an ammonium sulfate saturation of 40%. The purification procedure used for the isolation of the binding protein and the Western blot-based assay used for the detection of TSG-6 binding protein are described under Experimental Procedures. During Affini-filter chromatography, most of the TSG-6 binding activity eluted at 0.5M NaCl together with residual albumin. FPLC on a MonoQ column proved to be very efficient for further purification of the TSG-6 binding protein. SDS-PAGE followed by silver staining revealed that incubation of fractions from MonoQ-FPLC with recombinant TSG-6 protein resulted in the partial disappearance of a >200-kDa band and the appearance of a new band at 120 kDa (FIG. 20). This finding suggests that the human TSG-6 binding protein is greater than 200 kDa in size and hence considerably greater than its complex with TSG-6. During FPLC on superdex 200, the TSG-6 binding protein eluted with a retention volume corresponding to a molecular mass of about 270 kDa. Fractions containing TSG-6 binding activity were concentrated about 80-fold before SDS-PAGE was performed on 4–15% PAA gradient gels or 8% PAA gels under reducing conditions. Proteins were transferred electrophoretically to PVDF membranes. CBB staining revealed the presence of only one band greater than 200 kDa which was cut for microsequencing.

Microsequencing of the TSG-6 binding protein resulted in double signals for the first five cycles and one signal for each of the following seven cycles. Comparison of the resulting sequences with sequences stored in protein databases revealed that they identify 2 of the 3 chains of the human IαI (trypsin): the bikunin chain of IαI was presented by its 12 N-terminal amino acids, whereas the heavy chain 2 (HC1) was represented by its 5 N-terminal amino acids (Table 3). It is noteworthy that Ser$^{10}$ of the bikunin chain could not be identified. No signals corresponding to the heavy chain 1 (HC1) of IαI were retrieved. The microsequencing data along with the molecular mass of ~250 kDa (determined by SDS-PAGE) indicate that the TSG-6 binding protein is IαI rather than inter-α-like-inhibitor (IαLI) whose molecular mass is 130–140 kDa (Enghild et al., *J. Biol. Chem.* 264, 15975–15981 (1989); Rouet et al., *Biol. Chem. Hoppe-Seyler* 373, 1019–1024 (1992)). Subsequent microsequencing of another preparation of IαI purified from human serum allowed the identification of HC1 besides HC2 and bikunin. However, the detected amount of HC1 was substantially lower than that of the two other chains on a molar basis.

TABLE 3

N-Terminal Amino Acid Sequence of the Human TSG-6 Binding Protein Determined by Microsequencing

| Position | Amino Acid Residues | |
|---|---|---|
| 1 | Ala | Ser |
| 2 | Val | Leu |
| 3 | Leu | Pro |
| 4 | Pro | Glu |

TABLE 3-continued

N-Terminal Amino Acid Sequence of the Human TSG-6
Binding Protein Determined by Microsequencing

| Position | Amino Acid Residues | |
|---|---|---|
| 5 | Gln | Gly |
| 6 | Glu | —[a] |
| 7 | Glu | — |
| 8 | Glu | — |
| 9 | Gly | — |
| 10 | Xaa | — |
| 11 | Gly | — |
| 12 | Gly | — |
|  | (SEQ ID NO:7) | (SEQ ID NO:8) |

[a]Not determined.

Rapid Complex Formation between Recombinant TSG-6 Protein and IαI Purified from Human Serum at 37° C. The 120-kDa TSG-6/IαI complex formed readily when purified TSG-6 protein and purified IαI were incubated together at 37° C. but not at 0° C. (FIG. 21). At 37° C., complex formation was detectable within 2 min., and the reaction appeared to be complete by 10 min. At 0° C., however, little or no TSG-6/IαI complex was formed within 1 hr. (FIG. 21). Mono-specific rabbit antisera against either TSG-6 protein or IαI (FIG. 22) detect the 120-kDa complex in Western blots, indicating the presence of both TSG-6 and IαI epitopes in a stable complex. Besides the formation of the TSG-6/IαI complex of 120 kDa, incubation of TSG-6 protein with IαI resulted in the appearance of yet another band with a molecular mass of ~130 kDa (FIG. 23, line 2) which was detected by anti IαI but not by anti-TSG-6. This IαI derivative appears to be a byproduct of the reaction of TSG-6 with IαI. It should be noted that the 120-kDa TSG-6/Iαi complex is formed by purified TSG-6 and IαI proteins in the apparent absence of other proteins.

Composition of the TSG-6/IαI Complex. The 120-kDa complex, formed by incubating together purified TSG-6 protein and IαI, was isolated and identified by SDS-PAGE in an 8% PAA gel, electrotransfer to a PVDF membrane, and CBB staining. Microsequencing of the isolated band corresponding to the complex revealed the presence of TSG-6 protein (shown below in Table 4 as an amino acid sequence corresponding to amino acids 18–27 of SEQ ID NO:2), bikunin, and HC2 of IαI in nearly equimolar ratios (Table 4). Interestingly, Ser[10] of the bikunin chain, which was not detectable during microsequencing of IαI (see Table 1), was found in an equimolar amount in the TSG-6/IαI complex. The unexpected appearance of a serine residue in position 10 could reflect the presence of an additional chain or partial modification of one or more N-termini. A less likely possibility is that Ser[10] of the bikunin chain, which is glycosylated in IαI, might become deglycosylated in the process of TSG-6/IαI complex formation.

TABLE 4

N-Terminal Amino Acid Sequences of the TSG-6/IαI Complex
Determined by Microsequencing

| Position | Amino Acid Residues | | | Yield (pmol of phenylthiohydantoin (PTH)) | | |
|---|---|---|---|---|---|---|
|  | Bikunin | HC2 | TSG-6 |  |  |  |
| 1 | Ala | Ser | Trp | 10 | 12 | 15 |
| 2 | Val | Leu | Gly | 10 | 12 | 12 |
| 3 | Leu | Pro | Phe | 9 | 11 | 9 |
| 4 | Pro | Gly | Lys | 9 | 15 | 8 |
| 5 | Gln | Glu | Asp | 7 | 12 | 13 |
| 6 | Glu | Ser | Gly | 11 | 8 | 13 |
| 7 | Glu | Glu | Ile |  | 13 | 9 |
| 8 | Glu | Glu | Phe |  | 15 | 9 |
| 9 | Gly | Met | His | 11 | 9 | 6 |
| 10 | Ser | Met | Asn | 8 | 12 | 13 |
|  | SEQ ID NO:9 | SEQ ID NO:10 | SEQ ID NO:2 (18–27) |  |  |  |

The Stable Cross-Link in the TSG-6/IαI Complex is Provided by a Glycosaminoglycan Chain. The stability of the 120-kDa TSG-6/IαI complex during SDS-PAGE under reducing conditions raises the question of the nature of the interaction between TSG-6 and the other components of the complex. Addition of 8M urea before SDS-PAGE did not affect the 120-kDa complex (FIG. 23). The effect of treatment with 8M guanidine hydrochloride could not be fully evaluated because the detectability of both the TSG-6 band and the TSG-6/IαI in Western blots was significantly diminished. However, the TSG-6/IαI complex was still detectable after treatment with 8M guanidine hydrochloride. Taken together, these data reflect the high stability of the TSG-6/IαI complex, and the formation of a covalent bond cannot be ruled out.

It is known that the three polypeptide chains of IαI are cross-linked by a chondroitin sulfate chain (Enghild et al., *J. Biol. Chem.* 264, 15975–15981 (1989); Jessen et al., *FEBS Lett.* 230, 195–200 (1988); Balduyck et al., *Biol. Chem. Hoppe-Seyler* 370, 329–336 (1989). It has been shown that bikunin, HC2 of IαLI, and HC3 of pre-α-inhibitor (PαI) are covalently bound to chondroitin 4-sulfate (Enghild et al., *J. Biol. Chem.* 264, 15975–15981 (1989); *J. Biol. Chem.* 266, 747–751 (1991); *J. Biol. Chem.* 268, 8711–8716 (1993)). To determine if cross-linking via chondroitin sulfate is also required for the stability of the TSG-6/IαI complex, purified TSG-6 protein and IαI were first incubated together to allow the formation of the complex and then treated with chondroitin sulfate ABC lyase from *Proteus vulgaris* or hyaluronidase from *Streptomyces hyalurolyticus*. Treatment with chondroitin sulfate ABC lyase resulted in complete disappearance of the complex whereas hyaluronidase had no effect (FIG. 24)

Chondroitin Sulfate Associated with IαI is Required for the Formation of the TSG-6/IαI Complex. In order to determine the effect of chondroitin sulfate ABC lyase on either TSG-6 protein or IαI separately, purified TSG-6 protein and purified IαI from human serum were incubated with a limited amount of chondroitinase for 16 hrs. and then mixed with untreated IαI or TSG-6 protein, respectively. Western blotting revealed that IαI preincubated with chondroitin sulfate ABC lyase was no longer able to form a complex with untreated TSG-6 protein (FIG. 25). On the other hand, pretreatment with chondroitinase had little effect on the ability of TSG-6 protein to react with untreated IαI (FIG. 25). A slight decrease of the amount of TSG-6/IαI complex formed by chondroitinase-pretreated TSG-6 (FIG.

25) can be explained by carry-over of the enzyme into the final TSG-6-IαI incubation mixture because the chondroitinase could not be selectively inactivated. Limiting chondroitinase activity to the necessary minimum was essential in this experiment in order to prevent IαI inactivation during the final incubation. This finding suggests that IαI, but not TSG-6 protein, has a chondroitinase-sensitive structure required for the formation of the TSG-6/IαI complex.

DISCUSSION

We showed earlier that TSG-6 synthesis is rapidly induced in human diploid fibroblasts and peripheral blood mononuclear cells after stimulation with the inflammatory cytokines TNF and IL-1 (Lee et al., *Mol. Cell. Biol.* 10, 1982–1988 (1990), *J. Biol. Chem.* 268, 6154–6160 (1993); Wisniewski et al., *J. Immunol.* 151, 6593–6601 (1993)). The affinity of TSG-6 protein for hyaluronan suggests a possible association with the extracellular matrix and cartilage (Lee et al., *J. Cell Biol.* 116, 545–557 (1992)). High levels of TSG-6 protein in the synovial fluid of patients with rheumatoid arthritis and constitutive TSG-6 expression by cultured synovial cells from rheumatoid joints in vitro that was further enhanced by TNF and IL-1, suggested a role for TSG-6 in inflammatory diseases of connective tissue and cartilage (Wisniewski et al., *J. Immunol.* 151, 6593–6601 (1993)). Little is known, however, about the actions of TSG-6 at the molecular or cellular level. Here we show that recombinant human TSG-6 protein is readily incorporated into a stable 120-kDa complex if incubated with human, fetal bovine, rabbit, or mouse serum. Isolation and microsequencing of the human TSG-6 binding protein allowed its identification as IαI, an extensively studied serum protein.

IαI is a complex protein in which the bikunin chain is linked to HC1 and HC2 (Enghild et al., *J. Biol. Chem.* 264, 15975–15981 (1989); Gebhard et al., *Biol. Chem. Hoppe-Seyler* 371, Suppl. 13–22 (1990); Rouet et al., *Biol. Chem. Hoppe-Seyler* 373, 1019–1024 (1992)). Yet, sequence analysis of the TSG-6 binding protein purified from human serum revealed only the bikunin chain and HC2 (Table 1), and no indication for the presence of HC1 was obtained. Subsequent sequencing of another preparation of IαI purified from human serum resulted in the detection of very weak signals for the sequence of HC1, corresponding to about one-tenth of the other two chains on a molar basis. Other investigators who reported N-terminal sequencing data for IαI also received incomplete and divergent sequences for HC1 when sequencing the unmodified IαI molecule (Enghild et al., *J. Biol. Chem.* 264, 15975–15981 (1989); Jessen et al., *FEBS Lett.* 320, 195–200 (1988); Malki et al., *Biol. Chem. Hoppe-Seyler* 373, 1009–1018 (1992)). Nevertheless, little doubt exists that the TSG-6 binding proteins IαI because IαI is the only member of this protein family with a molecular mass greater than 200 kDa. IαLI, which consists of bikunin and HC2, the two chains we detected by microsequencing, has a molecular mass of only 130–140 kDa (Enghild et al., *J. Biol. Chem.* 264, 15975–15981 (1989); Rouet et al., *Biol. Chem. Hoppe-Seyler* 373, 1019–1024 (1992). In addition, we found that purified IαI forms what appears to be the same 120-kDa complex with TSG-6 proteins whole serum (FIGS. 21 and 22). While there is no doubt that IαI is the TSG-6 binding protein we have isolated, it is possible that IαLI or PαI also can bind TSG-6 protein.

Evidence that the reaction between TSG-6 and IαI indeed yields a complex of TSG-6 with one or more polypeptide chains of IαI is provided by the immunoprecipitation data (FIG. 19). Further information about the composition of the TSG-6/IαI complex is derived from Western blot analysis.

Antisera specific for either TSG-6 protein or IαI detected a 120-kDa band newly formed upon incubation of tSG-6 protein and IαI with each other (FIG. 22), suggesting the presence of TSG-6 and IαI epitopes in the complex. This was confirmed by microsequencing of the TSG-6/IαI complex (Table 2) which revealed the presence of three chains: TSG-6 protein, bikunin, and HC2. The signals of all three chains are represented in nearly equimolar amounts, suggesting that the complex contains one of each polypeptide chain. No signals corresponding to HC1 could be detected. The molecular mass of the complex is surprisingly low if one considers the molecular masses of the incorporated polypeptides. HC2 has a molecular mass of 70 kDa (Enghild et al., *J. Biol. Chem.* 264, 15975–15981 (1989)), the reported molecular mass of bikunin is 26–70 kDa depending on the extent of glycosylation (Gebhard et al., *Biol. Chem. Hoppe-Seyler* 371, Suppl. 13–22 (1990); Rouet et al, *Biol. Chem. Hoppe-Seyler* 373, 1019–1024 (1992)), and that of recombinant TSG-6 protein is 32 kDa. The fact that the apparent molecular mass of the 120-kDa complex is less than the sum of its components suggests that some additional modifications, such as deglycosylation or limited proteolytic cleavage, might take place. Alternatively, changes of the gross structure of the complex due to incorporation of TSG-6 could have a substantial effect on its apparent molecular mass.

The unusual stability of the TSG-6/IαI complex raises the question of the nature of the bonds linking its components. The resistance of the complex to boiling in 2% SDS and 5% β-mercaptoethanol as well as to 8M urea makes any non-covalent hydrophobic or hydrophilic bond unlikely. In addition, the strict temperature dependence of TSG-6/IαI complex formation (FIG. 22) suggests that the reaction involves an activated transition state and supports the notion that a covalent bond is formed. However, an unusually stable noncovalent bond is formed. However, an unusually stable noncovalent association of TSG-6 with the glycosaminoglycan chain of the complex cannot be ruled out. The polypeptide chains of IαI are cross-linked by chondroitin 4-sulfate chain (Enghild et al., *J. Biol. Chem.* 264, 15975–15981 (1989; Jessen et al., *FEBS Lett.* 230, 195–200 (1988); Balduyck et al., *Biol. Chem. Hoppe-Seyler* 370, 329–336 (1989)). The sensitivity of the TSG-6/IαI complex to chondroitin sulfate ABC lyase (FIG. 24) and the inability of chondroitinase-pretreated IαI to form the complex (FIG. 25) suggests that the chondroitin 4-sulfate chain cross-linking the polypeptide chains of IαI is also required for the formation of the 120-kDa complex. It has been shown that the chondroitin 4-sulfate chain of IαI is bound to Ser$^{10}$ of bikunin via a common Gal—Gal-Xyl oligosaccharide (Enghild et al., *J. Biol. Chem.* 264, 15975–15981 (1989); *J. Biol. Chem.* 266, 747–751 (1991); Chirat et al., *Int. J. Biochem.* 23, 1201–1203 (1991). An unusual ester bond has been shown to cross-link the α-carboxylic a group of the HC2 C-terminal Asp$^{648}$ of IαLI to C-6 of an internal N-acetyl-galactosamine of the chondroitin 4-sulfate chain (Enghild et al., *J. Biol. Chem.* 268, 8711–8716 (1993)). A similar bond cross-lings the C-terminal Asp$^{618}$ of HC3 to chondroitin 4-sulfate in PαI (Enghild et al., *J. Biol. Chem.* 266, 747–751 (1991); *J. Biol. Chem.* 268, 8711–8716 (1993). Analysis of the cDNAs of the three heavy chains showed that all have the conserved consensus sequence Val Xaa Asp Pro His Phe Ile Ile (SEQ ID NO:11) supposed to determine the cleavage site for the C-terminal propeptide (Bourguignon et al., *Eur. J. Biochem.* 212, 771–776 (1993)) after the aspartic acid residue. This cleavage generates the free a-carboxylic group of the now C-terminal aspartic acid residue which forms the ester bond to an internal N-acetylgalactosamine of chondroitin 4-sulfate, two reactions that may be closely coupled. Interestingly, TSG-6 also features a core of the consensus sequence Val Xaa Xaa Asp Pro$^{249}$ (corresponding to amino acid dues 1–5 of SEQ ID NO:11). Hence, it is conceivable that TSG-6 forms a direct covalent bond to the chondroitin 4-sulfate chain of IαI. Additional studies are required to determine the molecular structures formed and the exact nature of the interactions leading to the formation of the exceedingly stable TSG-6/IαI complex.

Although the trypsin-inhibitory activity of IαI has been known for a long time (Heide et al., *Clin. Chem. Acta* 11, 82–85 (1965)), little is known about the functions of the different members of the IαI family. However, disease-associated presence in various tissues and fluctuations seen in the serum levels of IαI and IαI-related proteins suggest an involvement in pathologic processes. Daveau et al., *Biochem. J.* 292, 485–492 (1993) reported a distinct pattern of changes in serum concentrations of the different members of the IαI family during acute inflammation. Proteins identical with, or closely related to, the bikunin chain of IαI have been detected in stroma and the surrounding connective tissue of malignant tumors (Yoshida et al., *Cancer* 64, 860–869 (1989)), in brain tissue of patients with Alzheimer's disease (Yoshida et al., *Biochem. Biophys. Res. Commun.* 174, 1015–1021 (1991)), and in serum and urine of patients with inflammatory disease, cancer, and leukemias (Rudman et al., *Cancer Res.* 36, 1837–1846 (1976); Franck & Pedersen, Scand. *J. Clin. Lab. Invest.* 43, 151–155 (1983); Chawla et al., *J. Cell Biochem.* 42, 207–217 (1990)). A link between IαI and rheumatoid arthritis was suggested over 20 years ago when Becker and Sandson, *Arthritis Rheum.* (1971), found IαI associated with hyaluronan in the synovial fluid of patients with rheumatoid arthritis, whereas no IαI was detectable in control synovial fluids. This finding was confirmed and extended to show that IαI associates in vitro with hyaluronan isolated from the synovial fluid of healthy subjects (Hutadilok et al., *Ann. Rheum. Dis.* 47, 377–385 (1988)). Huang et al *J. Biol. Chem.* 268, 26725–26730 (1993) showed recently that in the presence of serum the two heavy chains of IαI become covalently associated with hyaluronan.

The possible functional implications of complex formation between TSG-6 and IαI are still elusive. Though TSG-6 has been detected inhuman serum it is most prominent at sites of local inflammation (Wisniewski et al., 1993; and unpublished results). Therefore,, TSG-6/IαI interaction probably occurs most readily at inflammatory sites such as the synovial tissue in rheumatoid arthritis, where both TSG-6 and IαI are found at high concentrations together with hyaluronan. Indeed, synovial fluids from arthritis patients contained both the free 35-kDa form and the 120-kDa complexed form of TSG-6 protein (Wisniewski et al.,*J. Immunol.* 151, 6593–6601 (1993)). Recently, the rabbit homologue of TSG-6 has been cloned and characterized as a developmentally regulated protein (Feng & Liau, *J. Biol. Chem.* 268, 9387–9392, 21453 (1993)), supporting the idea that TSG-6 might play a role in developmental processes. Tissue remodeling could be the common denominator of TSG-6 association with developmental and inflammatory processes. The fact that human TSG-6 forms complexes of equal size with IαI from different mammalian species indicates that the molecular structures involved in the interaction are well conserved among mammals, perhaps reflecting selective pressure due to functional and structural constraints.

The references cited above are all incorporated by reference herein, whether specifically incorporated or not.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

What is claimed is:

1. A DNA molecule encoding Tumor Necrosis Factor Stimulated Gene 6 (TSG-6), wherein said DNA molecule comprises base pairs 69 to 899 of SEQ ID NO:1.

2. A DNA molecule encoding a human Tumor Necrosis Factor Stimulated Gene 6 (TSG-6), protein having the amino acid sequence SEO ID NO:2, substantially free of other human nucleotide sequences.

3. A DNA molecule according to claim 2 which is cDNA.

4. A DNA molecule according to claim 2 which is genomic DNA.

5. A DNA molecule according to claim 2 having the nucleotide sequence SEQ ID NO:1.

6. A DNA molecule according to claim 2 which is comprised in an expression vector.

7. A DNA molecule according to claim 6, wherein said vehicle is a plasmid.

8. A prokaryotic host cell transformed with the molecule of claim 6.

9. A host cell according to claim 8 which is a bacterium.

10. A eukaryotic host cell transfected with the molecule of claim 6.

11. A host cell according to claim 10 which is a yeast cell or a mammalian cell.

12. A process for preparing an isolated Tumor Necrosis Factor Stimulated Gene 6 (TSG-6), protein molecule having the amino acid sequence SEQ ID NO:2, comprising:

(a) culturing a host cell capable of expressing said protein under culturing conditions;

(b) expressing said protein; and (c) recovering said protein from said culture.

13. A process according to claim 12 wherein said host cell is prokaryotic.

14. A process according to claim 13 wherein said host cell is eukaryotic.

\* \* \* \* \*

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 1414 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens
        ( G ) CELL TYPE: Fibroblast
        ( H ) CELL LINE: FS-4

( i x ) FEATURE:
        ( A ) NAME/KEY: CDS ( B ) LOCATION: 69..899
( D ) OTHER INFORMATION:

( x i ) SEQUENCE DESCRIPTION: SEQ ID NO:1:

```
GAATTCGCAC TGCTCTGAGA ATTTGTGAGC AGCCCCTAAC AGGCTGTTAC TTCACTACAA                60

CTGACGAT ATG ATC ATC TTA ATT TAC TTA TTT CTC TTG CTA TGG GAA GAC                 110
         Met Ile Ile Leu Ile Tyr Leu Phe Leu Leu Leu Trp Glu Asp
           1               5                          10

ACT CAA GGA TGG GGA TTC AAG GAT GGA ATT TTT CAT AAC TCC ATA TGG                  158
Thr Gln Gly Trp Gly Phe Lys Asp Gly Ile Phe His Asn Ser Ile Trp
 15              20                  25                      30

CTT GAA CGA GCA GCC GGT GTG TAC CAC AGA GAA GCA CGG TCT GGC AAA                  206
Leu Glu Arg Ala Ala Gly Val Tyr His Arg Glu Ala Arg Ser Gly Lys
                 35                  40                  45

TAC AAG CTC ACC TAC GCA GAA GCT AAG GCG GTG TGT GAA TTT GAA GGC                  254
Tyr Lys Leu Thr Tyr Ala Glu Ala Lys Ala Val Cys Glu Phe Glu Gly
             50              55                      60

GGC CAT CTC GCA ACT TAC AAG CAG CTA GAG GCA GCC AGA AAA ATT GGA                  302
Gly His Leu Ala Thr Tyr Lys Gln Leu Glu Ala Ala Arg Lys Ile Gly
         65                  70                  75

TTT CAT GTC TGT GCT GCT GGA TGG ATG GCT AAG GGC AGA GTT GGA TAC                  350
Phe His Val Cys Ala Ala Gly Trp Met Ala Lys Gly Arg Val Gly Tyr
     80                  85                  90

CCC ATT GTG AAG CCA GGG CCC AAC TGT GGA TTT GGA AAA ACT GGC ATT                  398
Pro Ile Val Lys Pro Gly Pro Asn Cys Gly Phe Gly Lys Thr Gly Ile
 95              100                 105                     110

ATT GAT TAT GGA ATC CGT CTC AAT AGG AGT GAA AGA TGG GAT GCC TAT                  446
Ile Asp Tyr Gly Ile Arg Leu Asn Arg Ser Glu Arg Trp Asp Ala Tyr
                 115                 120                 125

TGC TAC AAC CCA CAC GCA AAG GAG TGT GGT GGC GTC TTT ACA GAT CCA                  494
Cys Tyr Asn Pro His Ala Lys Glu Cys Gly Gly Val Phe Thr Asp Pro
             130                 135                     140

AAG CGA ATT TTT AAA TCT CCA GGC TTC CCA AAT GAG TAC GAA GAT AAC                  542
Lys Arg Ile Phe Lys Ser Pro Gly Phe Pro Asn Glu Tyr Glu Asp Asn
         145                 150                 155

CAA ATC TGC TAC TGG CAC ATT AGA CTC AAG TAT GGT CAG CGT ATT CAC                  590
Gln Ile Cys Tyr Trp His Ile Arg Leu Lys Tyr Gly Gln Arg Ile His
     160                 165                 170

CTG AGT TTT TTA GAT TTT GAC CTT GAA GAT GAC CCA GGT TGC TTG GCT                  638
Leu Ser Phe Leu Asp Phe Asp Leu Glu Asp Asp Pro Gly Cys Leu Ala
175                 180                 185                 190

GAT TAT GTT GAA ATA TAT GAC AGT TAC GAT GAT GTC CAT GGC TTT GTG                  686
Asp Tyr Val Glu Ile Tyr Asp Ser Tyr Asp Asp Val His Gly Phe Val
                 195                 200                 205

GGA AGA TAC TGT GGA GAT GAG CTT CCA GAT GAC ATC ATC AGT ACA GGA                  734
Gly Arg Tyr Cys Gly Asp Glu Leu Pro Asp Asp Ile Ile Ser Thr Gly
             210                 215                 220

AAT GTC ATG ACC TTG AAG TTT CTA AGT GAT GCT TCA GTG ACA GCT GGA                  782
Asn Val Met Thr Leu Lys Phe Leu Ser Asp Ala Ser Val Thr Ala Gly
         225                 230                 235

GGT TTC CAA ATC AAA TAT GTT GCA ATG GAT CCT GTA TCC AAA TCC AGT                  830
Gly Phe Gln Ile Lys Tyr Val Ala Met Asp Pro Val Ser Lys Ser Ser
     240                 245                 250

CAA GGA AAA AAT ACA AGT ACT ACT TCT ACT GGA AAT AAA AAC TTT TTA                  878
Gln Gly Lys Asn Thr Ser Thr Thr Ser Thr Gly Asn Lys Asn Phe Leu
255                 260                 265                 270

GCT GGA AGA TTT AGC CAC TTA TAAAAAAAAA AAAGGATGAT CAAAACACAC                     929
Ala Gly Arg Phe Ser His Leu
                 275

AGTGTTTATG TTGGAATCTT TTGGAACTCC TTTGATCTCA CTGTTATTAT TAACATTTAT                989
```

```
TTATTATTTT  TCTAAATGTG  AAAGCAATAC  ATAATTTAGG  GAAAATTGGA  AAATATAGGA    1049

AACTTTAAAC  GAGAAAATGA  AACCTCTCAT  AATCCCACTG  CATAGAAATA  ACAAGCGTTA    1109

ACATTTTCAT  ATTTTTTTCT  TTCAGTCATT  TTTGTATTTG  TGGTATATGT  ATATATGTAC    1169

CTATATGTAT  TTGCATTTGA  AATTTGGAA   TCCTGCTCTA  TGTACAGTTT  TGTATTATAC    1229

TTTTTAAATC  TTGAACTTTA  TGAACATTTT  CTGAAATCAT  TGATTATTCT  ACAAAAACAT    1289

GATTTTAAAC  AGCTGTAAAA  TATTCTATGA  TATGAATGTT  TTATGCATTA  TTTAAGCCTG    1349

TCTCTATTGT  TGGAATTTCA  GGTCATTTTC  ATAAATATTG  TTGCAATAAA  TATCCTTCGG    1409

AATTC                                                                    1414
```

( 2 ) INFORMATION FOR SEQ ID NO:2:

( i ) SEQUENCE CHARACTERISTICS:
        ( A ) LENGTH: 277 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Ile  Ile  Leu  Ile  Tyr  Leu  Phe  Leu  Leu  Leu  Trp  Glu  Asp  Thr  Gln
 1              5                        10                       15

Gly  Trp  Gly  Phe  Lys  Asp  Gly  Ile  Phe  His  Asn  Ser  Ile  Trp  Leu  Glu
               20                       25                       30

Arg  Ala  Ala  Gly  Val  Tyr  His  Arg  Glu  Ala  Arg  Ser  Gly  Lys  Tyr  Lys
          35                        40                        45

Leu  Thr  Tyr  Ala  Glu  Ala  Lys  Ala  Val  Cys  Glu  Phe  Glu  Gly  Gly  His
     50                        55                        60

Leu  Ala  Thr  Tyr  Lys  Gln  Leu  Glu  Ala  Ala  Arg  Lys  Ile  Gly  Phe  His
65                        70                        75                        80

Val  Cys  Ala  Ala  Gly  Trp  Met  Ala  Lys  Gly  Arg  Val  Gly  Tyr  Pro  Ile
               85                        90                        95

Val  Lys  Pro  Gly  Pro  Asn  Cys  Gly  Phe  Gly  Lys  Thr  Gly  Ile  Ile  Asp
              100                       105                       110

Tyr  Gly  Ile  Arg  Leu  Asn  Arg  Ser  Glu  Arg  Trp  Asp  Ala  Tyr  Cys  Tyr
          115                       120                       125

Asn  Pro  His  Ala  Lys  Glu  Cys  Gly  Gly  Val  Phe  Thr  Asp  Pro  Lys  Arg
     130                       135                       140

Ile  Phe  Lys  Ser  Pro  Gly  Phe  Pro  Asn  Glu  Tyr  Glu  Asp  Asn  Gln  Ile
145                       150                       155                       160

Cys  Tyr  Trp  His  Ile  Arg  Leu  Lys  Tyr  Gly  Gln  Arg  Ile  His  Leu  Ser
               165                       170                       175

Phe  Leu  Asp  Phe  Asp  Leu  Glu  Asp  Asp  Pro  Gly  Cys  Leu  Ala  Asp  Tyr
              180                       185                       190

Val  Glu  Ile  Tyr  Asp  Ser  Tyr  Asp  Asp  Val  His  Gly  Phe  Val  Gly  Arg
          195                       200                       205

Tyr  Cys  Gly  Asp  Glu  Leu  Pro  Asp  Asp  Ile  Ile  Ser  Thr  Gly  Asn  Val
     210                       215                       220

Met  Thr  Leu  Lys  Phe  Leu  Ser  Asp  Ala  Ser  Val  Thr  Ala  Gly  Gly  Phe
225                       230                       235                       240

Gln  Ile  Lys  Tyr  Val  Ala  Met  Asp  Pro  Val  Ser  Lys  Ser  Ser  Gln  Gly
               245                       250                       255

Lys  Asn  Thr  Ser  Thr  Thr  Ser  Thr  Gly  Asn  Lys  Asn  Phe  Leu  Ala  Gly
              260                       265                       270
```

Arg Phe Ser His Leu
              275

(2) INFORMATION FOR SEQ ID NO:3:

(i) SEQUENCE CHARACTERISTICS:
        (A) LENGTH: 90 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

```
Gly Val Phe His Val Glu Lys Asn Gly Arg Tyr Ser Ile Ser Arg Thr
 1               5                  10                  15
Glu Ala Ala Asp Ile Cys Lys Ala Phe Asn Ser Thr Leu Pro Thr Met
            20                  25                  30
Ala Gln Met Glu Lys Ala Leu Ser Ile Gly Phe Glu Thr Cys Arg Tyr
        35                  40                  45
Gly Phe Ile Glu Gly His Val Val Ile Pro Arg Ile His Pro Asn Ser
    50                  55                  60
Ile Cys Ala Ala Asn Asn Thr Gly Val Tyr Ile Leu Thr Ser Asn Thr
65                  70                  75                  80
Ser Gln Tyr Asp Thr Tyr Cys Phe Asn Ala
                85                  90
```

(2) INFORMATION FOR SEQ ID NO:4:

(i) SEQUENCE CHARACTERISTICS:
        (A) LENGTH: 98 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

```
Gly Val Val Phe Pro Tyr Phe Pro Arg Leu Gly Arg Tyr Asn Leu Asn
 1               5                  10                  15
Phe His Glu Ala Arg Gln Ala Cys Leu Asp Gln Asp Ala Val Ile Ala
            20                  25                  30
Ser Phe Asp Gln Leu Tyr Asp Ala Trp Arg Gly Gly Leu Asp Trp Cys
        35                  40                  45
Asn Ala Gly Trp Leu Ser Asp Gly Ser Val Gln Tyr Pro Ile Thr Lys
    50                  55                  60
Pro Arg Glu Pro Cys Gly Gly Gln Asn Thr Val Pro Gly Val Arg Asn
65                  70                  75                  80
Tyr Gly Phe Trp Asp Lys Asp Lys Ser Arg Tyr Asp Val Phe Cys Phe
                85                  90                  95
Thr Ser
```

(2) INFORMATION FOR SEQ ID NO:5:

(i) SEQUENCE CHARACTERISTICS:
        (A) LENGTH: 97 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

-continued

```
Gly Val Val Phe His Tyr Arg Pro Gly Ser Thr Arg Tyr Ser Leu Thr
 1            5                    10                       15

Phe Glu Glu Ala Gln Asp Ala Cys Ile Arg Thr Gly Ala Ala Ile Ser
             20              25                  30

Ser Pro Glu Gln Leu Gln Ala Ala Tyr Ala Gly Tyr Glu Gln Cys Asp
         35              40                  45

Ala Gly Trp Leu Gln Asp Gln Thr Val Arg Tyr Pro Ile Val Ser Pro
     50              55                  60

Arg Thr Pro Cys Val Gly Asp Lys Asp Ser Ser Pro Gly Val Arg Ile
 65              70              75                           80

Tyr Gly Val Arg Pro Ser Ser Glu Thr Tyr Asp Val Tyr Cys Tyr Val
             85                      90                  95

Pro
```

( 2 ) INFORMATION FOR SEQ ID NO:6:

( i ) SEQUENCE CHARACTERISTICS:
        ( A ) LENGTH: 101 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:6:

```
Gly Gly Ser Ile Pro Ile Pro Gln Lys Leu Phe Gly Glu Val Thr Ser
 1            5                    10                       15

Pro Leu Phe Pro Lys Pro Tyr Pro Asn Asn Phe Glu Thr Thr Thr Val
             20              25                  30

Ile Thr Val Pro Thr Gly Tyr Arg Val Lys Leu Val Phe Gln Gln Phe
         35              40                  45

Asp Leu Glu Pro Ser Glu Gly Cys Phe Tyr Asp Tyr Val Lys Ile Ser
     50              55                  60

Ala Asp Lys Lys Ser Leu Gly Arg Phe Cys Gly Gln Leu Gly Ser Pro
 65              70              75                           80

Leu Gly Asn Pro Pro Gly Lys Lys Glu Phe Met Ser Gln Gly Asn Lys
             85                      90                  95

Met Leu Leu Thr Phe
            100
```

( 2 ) INFORMATION FOR SEQ ID NO:7:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:7:

```
Ala Val Leu Pro Gln Glu Glu Glu Gly Xaa Gly Gly
 1            5                    10
```

( 2 ) INFORMATION FOR SEQ ID NO:8:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide (xi) SEQUENCE DESCRIPTION: SEQ ID NO:8:

Ser Leu Pro Glu Gly
1             5

(2) INFORMATION FOR SEQ ID NO:9:

(i) SEQUENCE CHARACTERISTICS:
      (A) LENGTH: 10 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:9:

Ala Val Leu Pro Gln Glu Glu Glu Gly Ser
1             5                      10

(2) INFORMATION FOR SEQ ID NO:10:

(i) SEQUENCE CHARACTERISTICS:
      (A) LENGTH: 10 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:10:

Ser Leu Pro Gly Glu Ser Glu Glu Met Met
1             5                      10

(2) INFORMATION FOR SEQ ID NO:11:

(i) SEQUENCE CHARACTERISTICS:
      (A) LENGTH: 9 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:11:

Val Xaa Xaa Asp Pro His Phe Ile Ile
1             5